US010856908B2

(12) United States Patent
Mullaney

(10) Patent No.: US 10,856,908 B2
(45) Date of Patent: Dec. 8, 2020

(54) EXTERNAL BONE FIXATION SYSTEMS

(71) Applicant: AMDT HOLDINGS, INC., Collierville, TN (US)

(72) Inventor: Michael Mullaney, Naples, FL (US)

(73) Assignee: AMDT HOLDINGS, INC., Collierville, TN (US)

( * ) Notice: Subject to any disclaimer, the term of this patent is extended or adjusted under 35 U.S.C. 154(b) by 1 day.

(21) Appl. No.: 16/059,733

(22) Filed: Aug. 9, 2018

(65) Prior Publication Data

US 2018/0344354 A1   Dec. 6, 2018

Related U.S. Application Data

(63) Continuation of application No. PCT/US2017/017276, filed on Feb. 10, 2017.
(Continued)

(51) Int. Cl.
*A61B 17/66* (2006.01)
*A61B 17/62* (2006.01)
(Continued)

(52) U.S. Cl.
CPC ............ *A61B 17/62* (2013.01); *A61B 17/645* (2013.01); *A61B 17/6475* (2013.01);
(Continued)

(58) Field of Classification Search
CPC ......... A61B 17/60–666; A61B 17/8685; F16B 5/0275
See application file for complete search history.

(56) References Cited

U.S. PATENT DOCUMENTS 4,784,125 A * 11/1988 Monticelli ............ A61B 17/62
606/56
5,030,052 A * 7/1991 Anderson ............... E04G 23/02
411/383
(Continued)

FOREIGN PATENT DOCUMENTS

CN    204618370 U    9/2015
FR    2576774        8/1986

OTHER PUBLICATIONS

Extended European Search Report for European Application No. 17750796.9 dated Jun. 7, 2019.
(Continued)

*Primary Examiner* — Eduardo C Robert
*Assistant Examiner* — Steven J Cotroneo
(74) *Attorney, Agent, or Firm* — Heslin Rothenberg Farley & Mesiti P.C.

(57) ABSTRACT

The present application provides external bone fixation systems. The systems include one or more pairs of bone fixation platforms in the form of rings or partial rings. The platforms may be coupled to corresponding bone segments. The pair of platforms are configured to accept a plurality of struts extending therebetween. The struts are configured to attach to the platforms via joints that provide three degrees of rotation. The struts are also configured such that their longitudinal length extending between the joints/platforms can be incrementally adjusted while attached to the platforms. The struts are further configured such that their total range of length adjustment can be increased by coupling at least one add-on component to the struts in situ. The lengths of each of the plurality of struts may be adjusted to arrange the platforms, and thereby the bone segment coupled thereto, in particular relative positions and orientations.

20 Claims, 78 Drawing Sheets

Related U.S. Application Data

(60) Provisional application No. 62/362,351, filed on Jul. 14, 2016, provisional application No. 62/415,741, filed on Nov. 1, 2016.

(51) Int. Cl.
*A61B 17/64* (2006.01)
*A61B 34/20* (2016.01)
*A61B 90/00* (2016.01)

(52) U.S. Cl.
CPC .......... *A61B 17/6408* (2013.01); *A61B 17/66* (2013.01); *A61B 2034/2055* (2016.02); *A61B 2090/3983* (2016.02)

(56) References Cited

U.S. PATENT DOCUMENTS

| | | | | |
|---|---|---|---|---|
| 5,681,309 A * | 10/1997 | Ross, Jr. | ............... | A61B 17/62 606/54 |
| 5,702,389 A | 12/1997 | Taylor et al. | | |
| 5,971,894 A | 10/1999 | Taylor et al. | | |
| 5,971,984 A * | 10/1999 | Taylor | ............... | A61B 17/62 128/898 |
| 6,009,779 A * | 1/2000 | Mastroni | ............... | B25B 15/00 81/177.2 |
| 6,030,386 A * | 2/2000 | Taylor | ............... | A61B 17/62 606/54 |
| 8,057,474 B2 * | 11/2011 | Knuchel | ............... | A61B 17/6458 606/258 |
| 8,308,772 B2 * | 11/2012 | Clement | ............... | A61B 17/7037 606/267 |
| 8,574,232 B1 * | 11/2013 | Ross | ............... | A61F 5/042 606/57 |
| 8,585,740 B1 * | 11/2013 | Ross | ............... | A61B 17/66 606/258 |
| 8,858,555 B2 * | 10/2014 | Crozet | ............... | A61B 17/645 606/54 |
| 9,039,706 B2 * | 5/2015 | Murray | ............... | A61B 17/62 606/54 |
| 9,101,398 B2 * | 8/2015 | Singh | ............... | A61B 17/62 |
| 9,419,421 B1 * | 8/2016 | Valentine | ............... | H02G 3/14 |
| 10,010,350 B2 * | 7/2018 | Mannanal | ............... | A61B 17/62 |
| 2002/0010465 A1 | 1/2002 | Koo et al. | | |
| 2005/0251135 A1 | 11/2005 | Riccione et al. | | |
| 2005/0267722 A1 * | 12/2005 | Marquart | ............... | A61B 5/1071 703/11 |
| 2007/0005523 A1 | 3/2007 | McGrath | | |
| 2010/0087819 A1 * | 4/2010 | Mullaney | ............... | A61B 17/62 606/56 |
| 2011/0082458 A1 * | 4/2011 | Crozet | ............... | A61B 17/62 606/54 |
| 2012/0095462 A1 | 4/2012 | Miller | | |
| 2013/0204248 A1 | 8/2013 | Singh et al. | | |
| 2014/0276821 A1 | 9/2014 | Murray et al. | | |
| 2015/0250501 A1 | 9/2015 | Orsak et al. | | |
| 2015/0272624 A1 | 10/2015 | Singh | | |
| 2016/0022314 A1 * | 1/2016 | Bordeaux | ............... | A61B 17/6466 606/56 |

OTHER PUBLICATIONS

International Search Report and Written Opinion of the International Searching Authority issued for PCT Application PCT/US2017/017276 dated Jun. 6, 2017.

International Search Report and Written Opinion of the International Searching Authority issued in PCT Application No. PCT/US2017/020285 dated May 25, 2017.

* cited by examiner

EXTERNAL BONE FIXATION SYSTEMS

CROSS REFERENCE TO RELATED APPLICATIONS

This present application is a continuation of PCT Patent Application No. US/2017/107276, filed Feb. 10, 2017, and entitled External Bone Fixation Systems, U.S. Provisional Patent Application No. 62/362,351 filed on Jul. 14, 2016, and U.S. Provisional Patent Application No. 62/415,741 filed on Nov. 1, 2016, the contents of which are hereby expressly incorporated herein by reference in their entireties.

FIELD OF THE INVENTION

The present disclosure is generally directed to external bone fixation systems and related methods. More particularly, the present disclosure is directed to external bone fixation systems and related methods that include a plurality of length-adjustable struts rotatably coupled between a pair of platforms configured to affix to bone segments.

BACKGROUND OF THE INVENTION

External fixation devices have been used to treat bone and tissue conditions by positioning bone or tissue segments in desired relative positions based on particular clinical needs. One form of external fixation devices is a hexapod fixation device. Hexapod devices, or more formally called Stewart platforms, include six degree of freedom (6DOF) parallel manipulators or struts. Generally, these devices have the ability to manipulate an article of interest relative to a base in all three orthogonal axis translations (X, Y, Z position) and all rotations about those three orthogonal axes (roll, pitch, yaw pose).

When configured as bone or tissue fixation systems, hexapod systems typically include a pair of rings that serve as bone fixation platforms. The platforms are typically connected with six struts that extend between the platforms. The struts and platforms are commonly connected via spherical or cardan joints that allow three rotations about three orthogonal axes. While some of these struts allow for length adjustment, their minimum and/or maximum lengths may not meet the needs of a particular clinical situation. For example, minimizing the distance between the platforms to a distance less than that afforded by a particular strut requires the use of a shorter struts—which naturally limits the adjustable range (i.e., the maximum length) of the struts.

As a result, current hexapod bone fixation systems utilize a collection of struts of differing lengths (or differing length ranges) which provide "short" struts for use when the platforms need to be close together and "long" struts for use when the platforms need to be further apart. In many instances these struts must be progressively or regressively swapped for the next length strut during a bone or tissue correction process, which is both a time consuming and costly process given that the strut being replaced cannot be re-used. Further complicating such systems is that some situations require a variety of differing strut lengths. For example, a variety of differing strut lengths is commonly required when extreme initial angulations or rotations are present. The selection process of the correct combination of differing strut lengths in such a situation is a time consuming process that is typically carried out by trial and error in an operating room. Such systems and situations thereby also require an excessive amount of inventory, which is also costly and often confusing to properly utilize.

Physically changing struts, aside from being a nuisance, also limits the available dynamic range of the system when attempting to reduce a deformity in an acute fashion. In this situation, struts are usually not added until such an acute correction is accomplished leaving the reduction to be held by operation room staff while additional members of the operation room staff pick and choose which struts will fit between the platforms at the prescribed locations. This process is time consuming and requires a large inventory.

Current hexapod fixation systems also typically utilize connections between the platforms and struts that require the use of one or more fasteners that need be tightened at the time of application. As such, connecting six struts at both ends to the platforms (i.e., twelve connections), sometimes in a trial and error fashion, is a difficult and time consuming task. Complicating matters is the fact that many current hexapod fixation systems utilize loose fasteners which must be applied using instruments. These fasteners and instruments add to the collection of parts and materials which must be kept track of in an operating room setting while the fixation system is employed, such as while a reduction is trying to be maintained.

Accordingly, hexapod fixation systems and related methods that provide increased length adjustment ranges while remaining coupled to the platforms, decrease the amount of associated inventory, can be installed relatively quickly, and reduce costs are desirable.

SUMMARY OF THE INVENTION

In one aspect, the present disclosure provides an external bone fixation system, comprising a first platform, a second platform and at least six length-adjustable strut assemblies. The first platform defines an opening and is configured to couple to a first bone segment. The second platform defines an opening and is configured to couple to a second bone segment. Each of the strut assemblies include an externally threaded rod portion translatable through a strut body portion. The rod portion of each strut assembly is coupled to one of the first and second platforms via a respective joint and the strut body portion of each strut assembly is coupled to the other of the first and second platforms via a respective joint. The strut assemblies are coupled to the first and second platforms in pairs of strut assemblies spaced about the first and second platforms. The pairs of strut assemblies each include a first strut assembly coupled to the respective platform via the joint of the threaded rod portion thereof and a second strut assembly coupled to the respective platform via the joint of the strut body portion thereof.

In another aspect, the present disclosure provides an external bone fixation system including a first platform, a second platform and a plurality of length-adjustable strut assemblies. The first platform is configured to couple to a first bone segment and defining an opening. The second platform is configured to couple to a second bone segment and defining an opening. The strut assemblies extend between the first and second platform within an operable range of angulation or orientation with respect to the platforms. At least one of the rod portion and the body portion of each strut assembly is configured to attach to one of the first platform and the second platform by engaging the respective platform in a non-operable angulation or orientation with respect thereto and rotation of the strut assembly into the operable range of angulation or orientation.

In another aspect, the present disclosure provides a strut assembly for an external bone fixation system. The strut assembly includes a strut body, an externally threaded first rod portion and an externally threaded add-on rod portion. The strut body portion includes a cavity extending therethrough and internal threads. The strut body also includes a first joint at an end portion thereof configured to couple to a fixation platform. The first rod portion is translatable through the strut body portion. The first rod portion includes a second joint at an end portion thereof configured to couple to a fixation platform. The externally threaded add-on rod portion is configured to attach to the first rod portion to extend the length thereof. The length between the first and second joints is adjustable. The add-on rod portion is attachable to the first rod portion when the first and second joints are each coupled to a platform.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the external bone fixation systems and related methods described herein there is shown illustrative embodiments. These illustrative embodiments are in no way limiting in terms of the precise arrangement and operation of the disclosed external fixation systems and other similar embodiments are envisioned.

DETAILED DESCRIPTION

Figure 1:
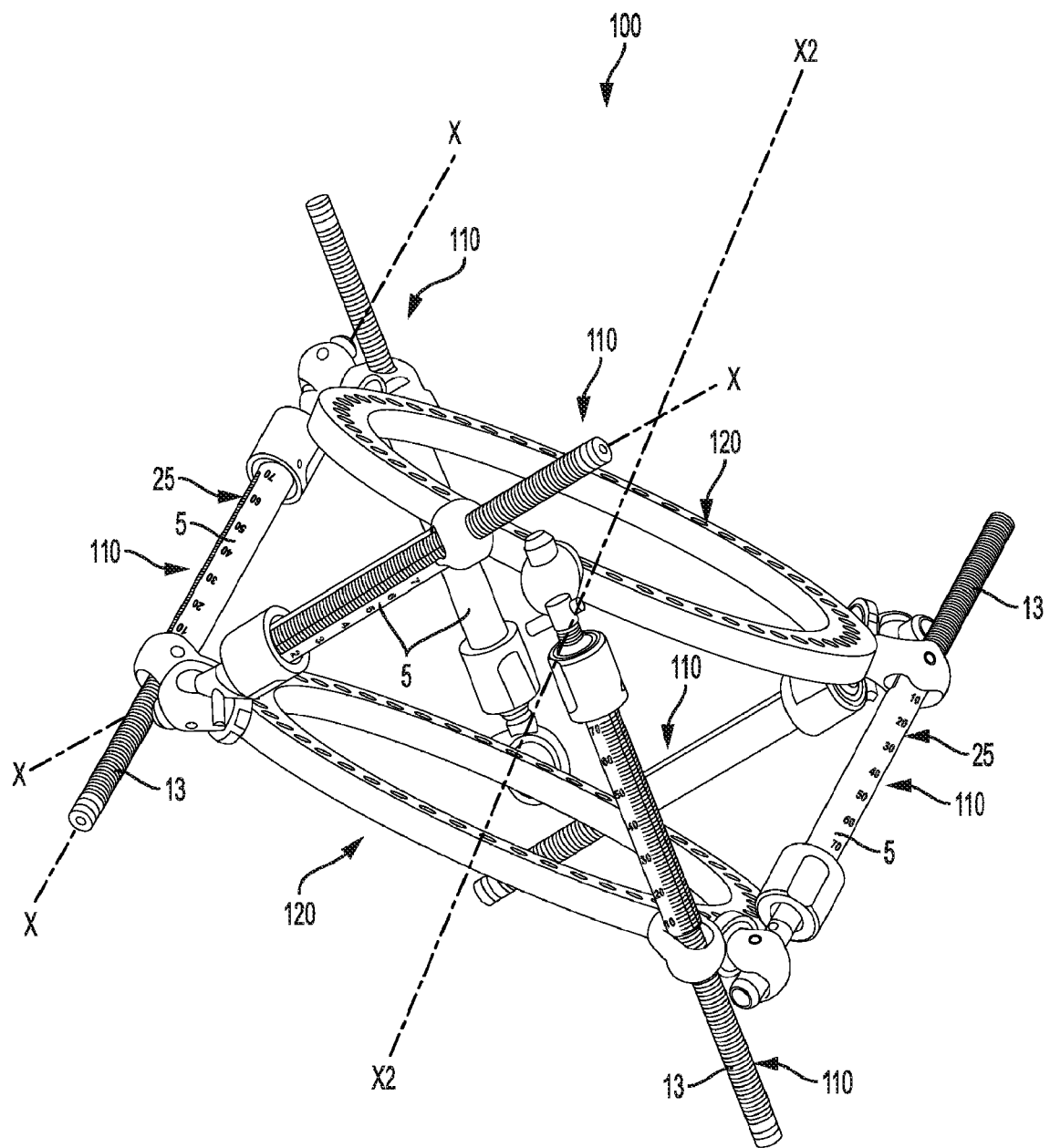
FIG. 1 is a perspective view of an external bone fixation system in a first configuration corresponding to a most compact configuration including a plurality of platforms and a plurality of interconnected strut assemblies.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure provides for six degree of freedom (6DOF) bone or tissue fixation systems and related fixation methods 100 as shown in FIGS. 1-18 which include the desirable stability and mobility characteristics of a hexapod system without time consuming strut-length choices and assembly difficulties. The fixation systems 100, as shown in FIGS. 1-18, also include struts assemblies 110 with relatively large dynamic ranges such that acute reductions in the operating room are not limited by the system 100 itself and the necessity of selecting and replacing one or more of the struts 110 during the reduction process. In some embodiments, the fixation systems and related fixation methods of the present disclosure 100 as shown in FIGS. 1-18 are particularly advantageous for the repair of fractures or deformities, such as fractures of or deformities in relatively long bones.

Figure 2:
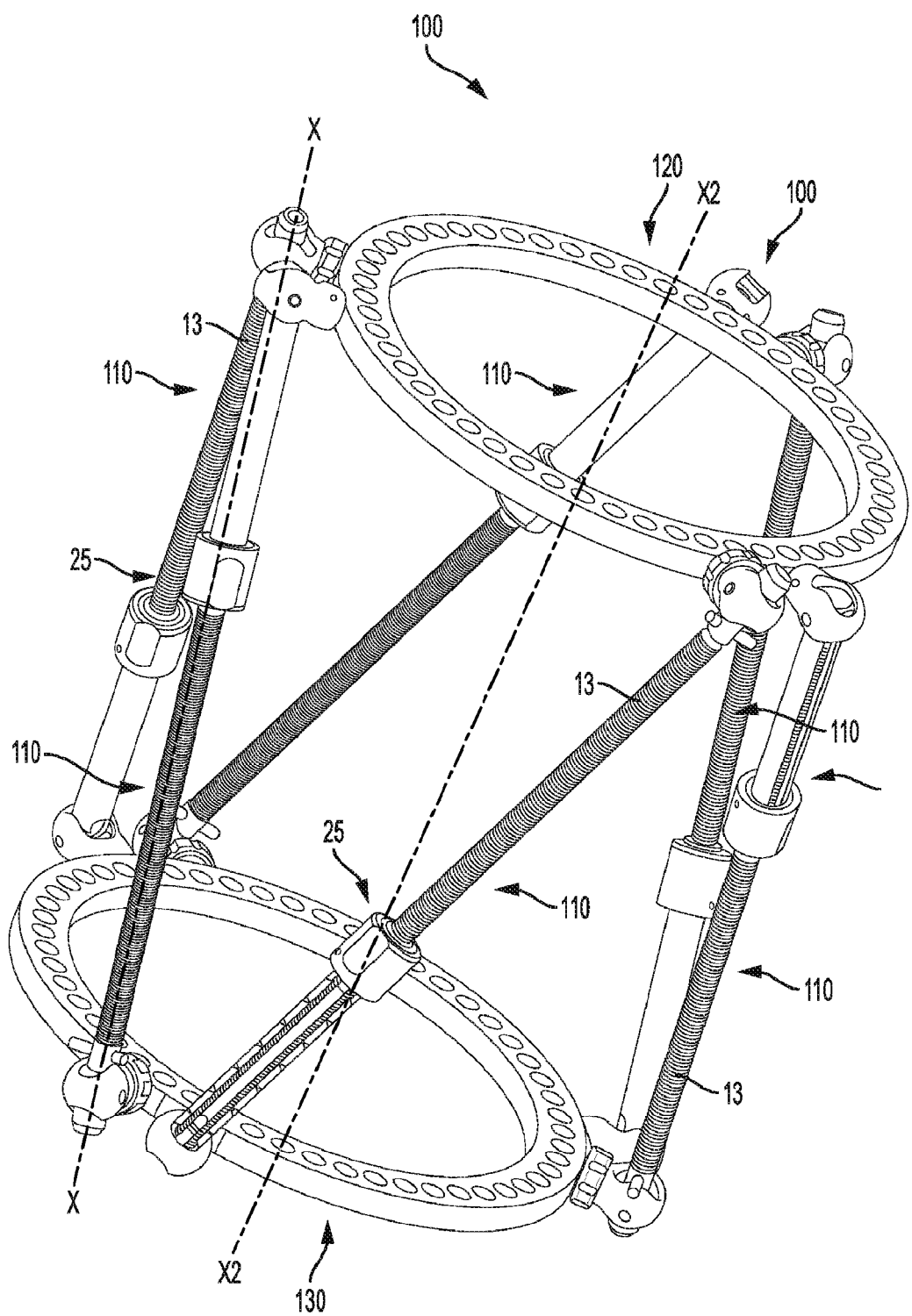
FIG. 2 is a perspective view of the external bone fixation system of FIG. 1 in a second configuration corresponding to an extended configuration or state.
Figure 3:
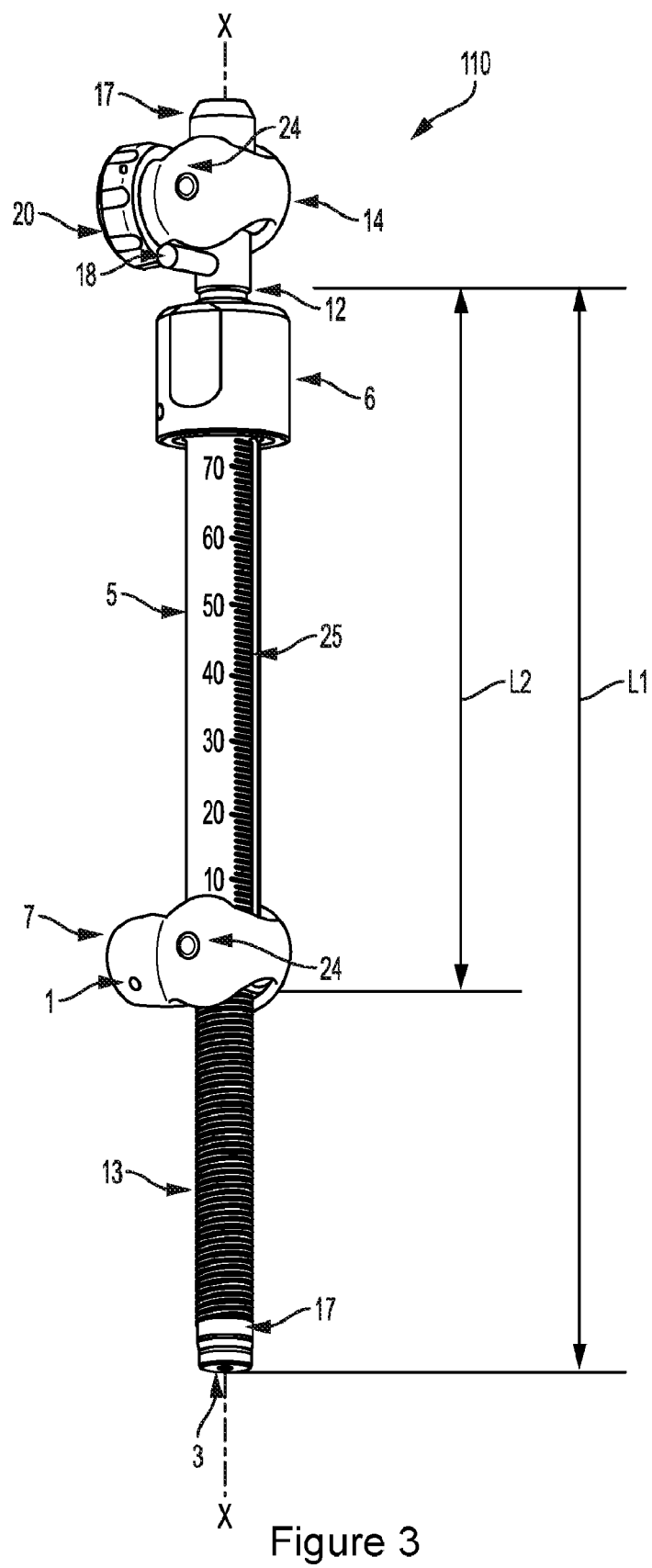
FIG. 3 is a perspective view of a strut assembly of the external bone fixation system of FIG. 1 shown in a most compact state.
Figure 4:
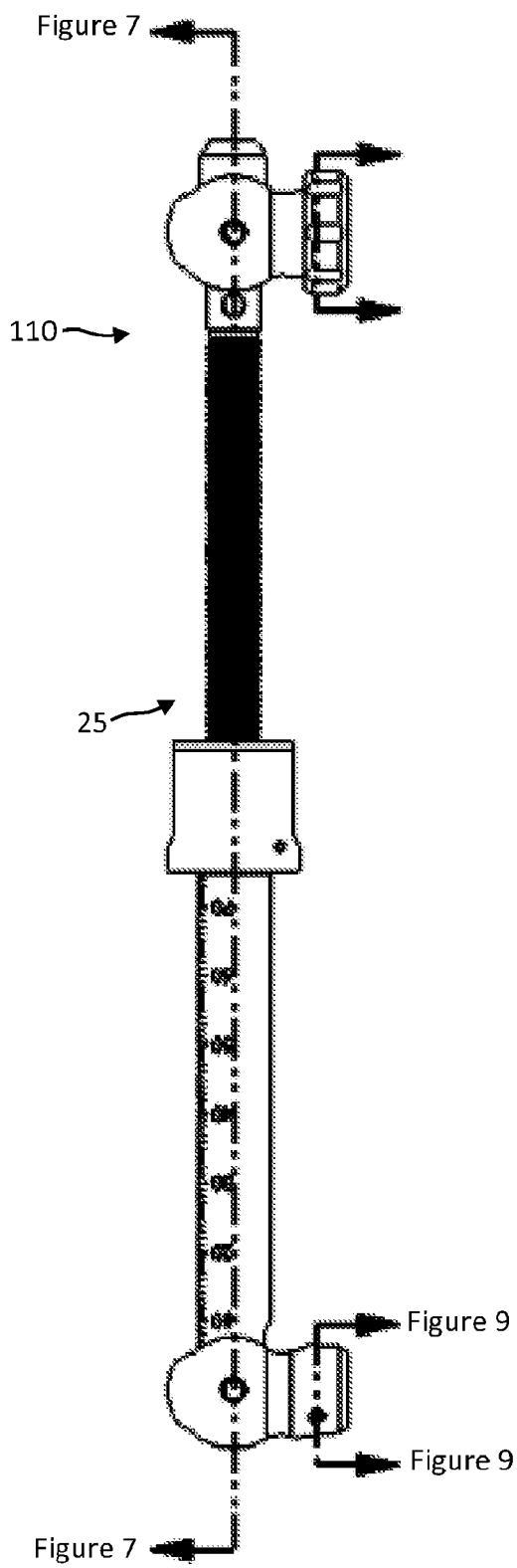
FIG. 4 is a side view of a strut assembly of the external bone fixation system of FIG. 1 shown in an extended configuration or state.
Figure 5:
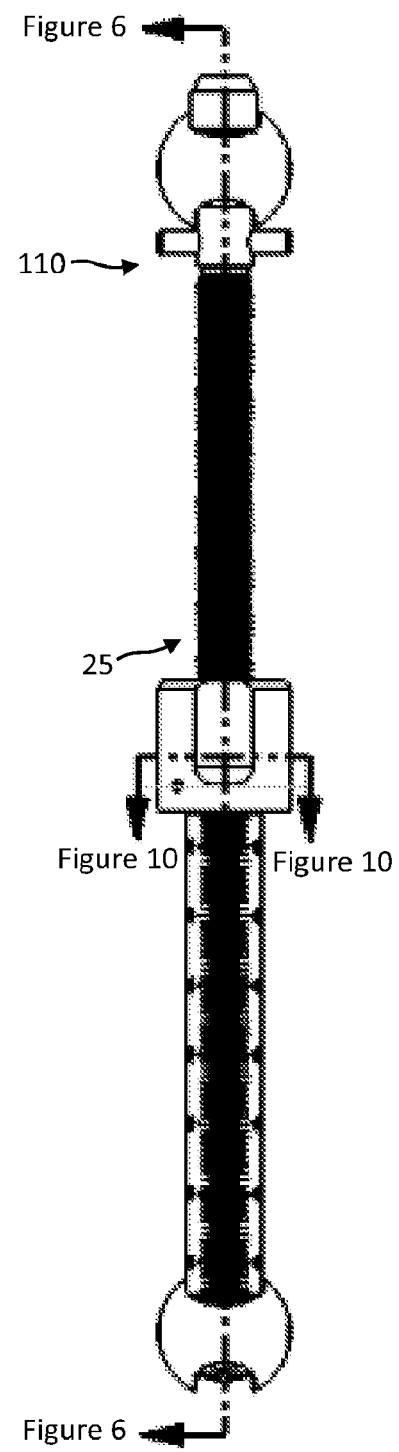
FIG. 5 is a front view of the strut assembly of FIG. 4.
Figures 6, 7:
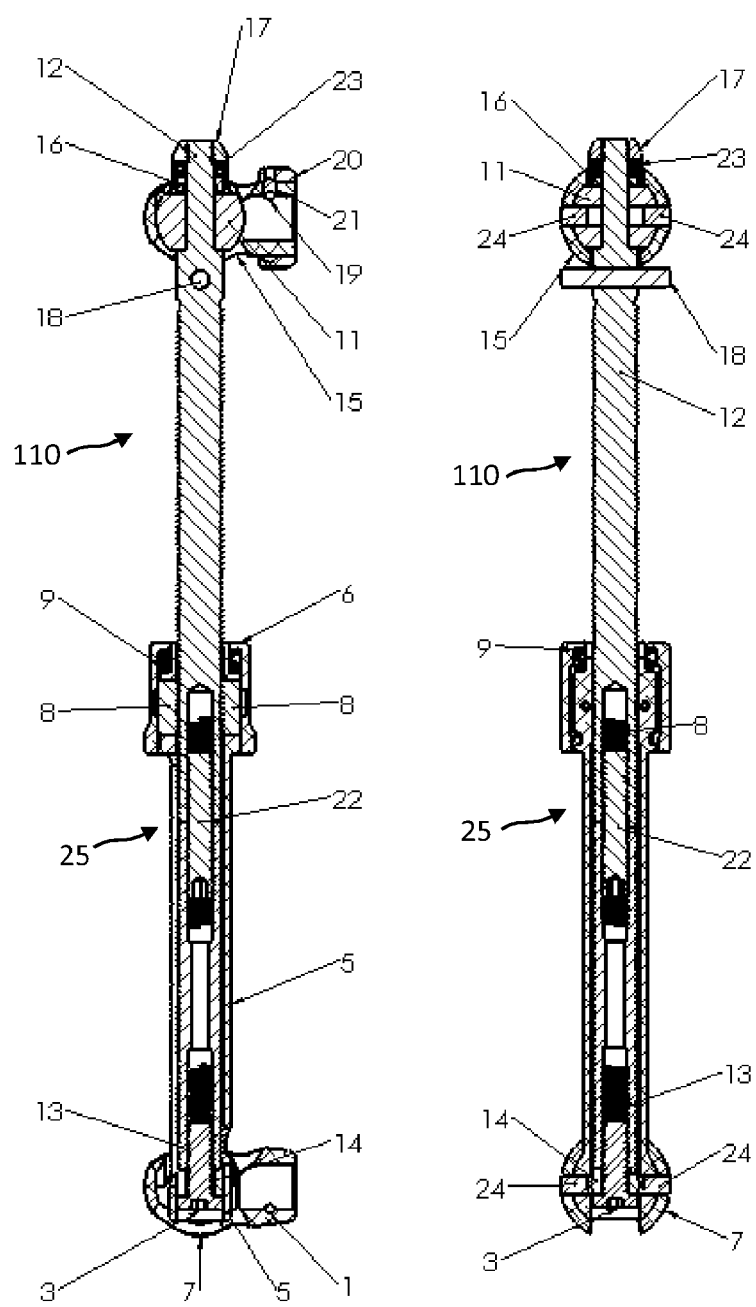
FIG. 6 is a side cross-sectional view of the strut assembly of FIG. 4 as indicated in FIG. 5.
FIG. 7 is a front cross-sectional view of the strut assembly of FIG. 4 as indicated in FIG. 4.
Figure 8:
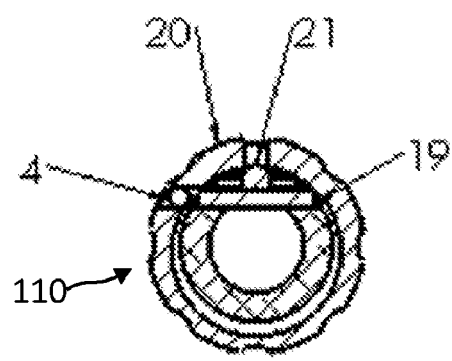
FIG. 8 is a cross-sectional view of the strut assembly of FIG. 4 as indicated in FIG. 4.
Figure 9:
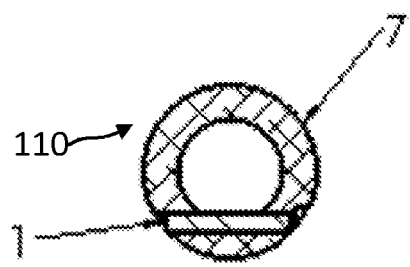
FIG. 9 is a cross-sectional view of the strut assembly of FIG. 4 as indicated in FIG. 4.
Figure 10:
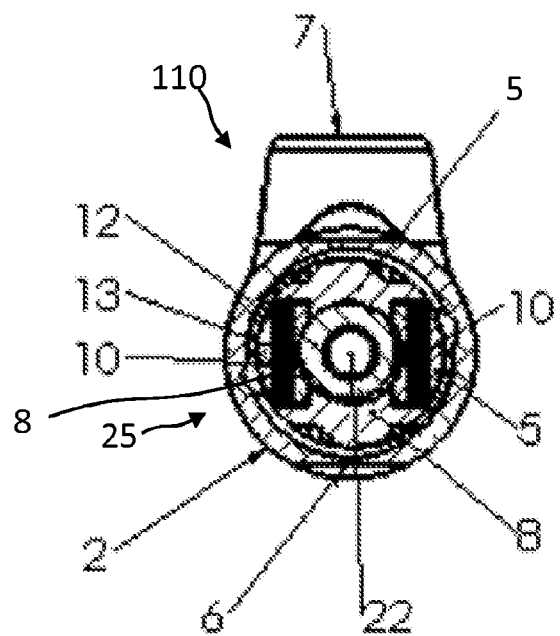
FIG. 10 is a cross-sectional view of the strut assembly of FIG. 4 as indicated in FIG. 5.

In one embodiment, the fixation systems or devices 100 include strut assemblies each formed of a threaded rod assembly 25 threadably coupled within a strut body 5. As explained further below, the threaded rod assembly 25 may include a first strut screw or rod 12 and, potentially, a second add-on strut screw or rod 13. The threaded rod assembly 25 may include external threads, as shown in FIGS. 1-7, 10, 12 and 13. As also shown in FIGS. 1-3 the threaded rod assembly 25 may include or define a longitudinal axis X-X, and may be elongate along the axis X-X. In some embodiments, the threaded rod assembly 25 may be cylindrical. The threaded rod assembly 25 may define a length L1 along the longitudinal axis X-X which includes the external threads, as shown in FIG. 3.

As shown in FIGS. 1-7 and 11, the threaded rod assembly 25 may be translatably received within the strut body 5. The strut body 5 may thereby include a non-threaded and potentially substantially smooth cavity configured to accept the strut body 5 therein/therethrough, such as along the longitudinal axis X-X. The strut body 5, and potentially the cavity thereof, may define a length L2 along the longitudinal axis X-X that is less than the length L1 of the threaded rod assembly 25, as shown in FIG. 3. The strut body 5 may be configured such that the strut body 5 is free to extend and/or translate through the strut body 5, as shown in FIGS. 1, 3-7, 16 and 17. As explained further below, one end portion of the strut body 5 may be coupled to a first platform 120, and an opposing end portion of the threaded rod assembly 25 may be coupled to a second platform 130. In this way, the strut body 5 and the threaded rod assembly 25 may translate with respect to each other along the axis X-X to provide a relatively large range of length adjustability to the strut assembly 110 and, thereby the distance and/or orientation between the first and second platforms 120, 130 as shown in FIGS. 1 and 2.

As explained further below, the first and second platforms 120, 130 may be rings or partial rings such that they extend, at least partially, about an opening and/or an axis X2-X2 (and, potentially, at least partially about bone and/or tissue in situ). The strut assemblies 110 may be coupled to the first and second platforms 120, 130 about the axis X2-X2. For example, as shown in FIGS. 1 and 2 the strut assemblies 110 may be positioned and coupled circumferentially to the first and second platforms 120, 130, and each strut assembly 110 may be attached to the first and second platforms 120, 130 at differing positions about the axis X2-X2. As such, the strut assemblies 110 may be angled with respect to the axis X2-X2.

As shown in FIGS. 1 and 2, the strut assemblies 110 may be arranged and coupled with the first and second platforms 120, 130 in such a configuration that provides clearance for the extension of the threaded rod assembly 25 from the strut body 5 (or vice versa). For example, the strut assemblies 110 may be coupled to the first and second platforms 120, 130 in pairs of adjacent and relatively closely spaced joints, and such pairs of strut assemblies 110 may be spaced a relatively closely greater distance apart about the first and second platforms 120, 130 (and thereby about the axis X2-X2). Each pair of strut assemblies 110 may include a joint coupling the threaded rod assembly 25 of one strut assembly 110 to the first or second platform 120, 130 and a joint coupling the strut body 5 of the other strut assembly 110 to the first or second platform 120, 130. The strut assemblies 110 are thereby joined to the first and second platforms 120, 130 in an alternating pattern or orientation.

The strut assemblies 110 of each pair coupled to the first and second platforms 120, 130 may extend to the other platform 120, 130 at opposing angular directions about the axis X2-X2—one strut assembly 110 may extend and couple to the other platform 120, 130 at a differing clockwise position and the other strut assembly 110 may extend and couple to the other platform 120, 130 at a differing counter clockwise position.

As discussed above, the strut assemblies 110 may be configured such that the threaded rod assembly 25 is able to extend fully through the strut body 5, such as shown in a distracted arrangement as shown in FIGS. 1 and 3. As each pair of strut assemblies 110 includes one joint coupling the threaded rod assembly 25 of a first strut assembly 110 to the respective first or second platform 120, 130 and one joint coupling the strut body 5 of a second strut assembly 110 to the respective first or second platform 120, 130, the threaded rod assembly 25 of the second strut assembly 110 is able to extend out from the strut body 5 (coupled to the respective first or second platform 120, 130) without interference from the first strut assembly 110, as shown in FIG. 1. The alternating orientation of the strut assemblies 110 of the pairs of strut assemblies 110 coupled to the first and second platform 120, 130 thereby allows the threaded rod assembly 25 to define a relatively long length L1. In this way, the system 100 is able to provide an acute reduction of the distance between the first and second platform 120, 130 (and the bone or tissue segments coupled thereto) as shown in FIG. 1, while still providing for adjustment to a relatively large distance (i.e., relatively large distraction) as shown in FIG. 2. This relatively large dynamic envelop of the adjustability of the first and second platforms 120, 130 is thereby provided without the need for the replacement of or addition to the strut assemblies 110, which can advantageously free up the surgeon to concentrate on the orthopedic condition and the reduction of the fracture or deformity.

As shown in FIGS. 3-7 and described above, the threaded rod assembly 25 (i.e., the first strut screw or rod 12 and, potentially, the second add-on strut screw or rod 13) may be provided within an open cavity of the strut body 5 and threadably engage with corresponding internal threads of the strut body 5. The strut assemblies 110 thereby from a prismatic joint (via the threaded rod assembly 25 and the strut body 5). In some embodiments, the strut body 5 of the strut assemblies 110 may be threadably engaged with the threaded rod assembly 25 via at least one threaded key 8, as shown in FIGS. 6, 7, 10 and 11. The at least one key 8 may include or form internal thread that corresponds to the external thread of the threaded rod assembly 25. The strut assemblies 110 may be configured such that the at least one key 8 (such as two opposing keys 8, 8) is able to be manually moved in and out in a radial fashion (e.g., with respect to the axis X-X) to engage and disengage the threaded rod assembly 25.

Figure 11:
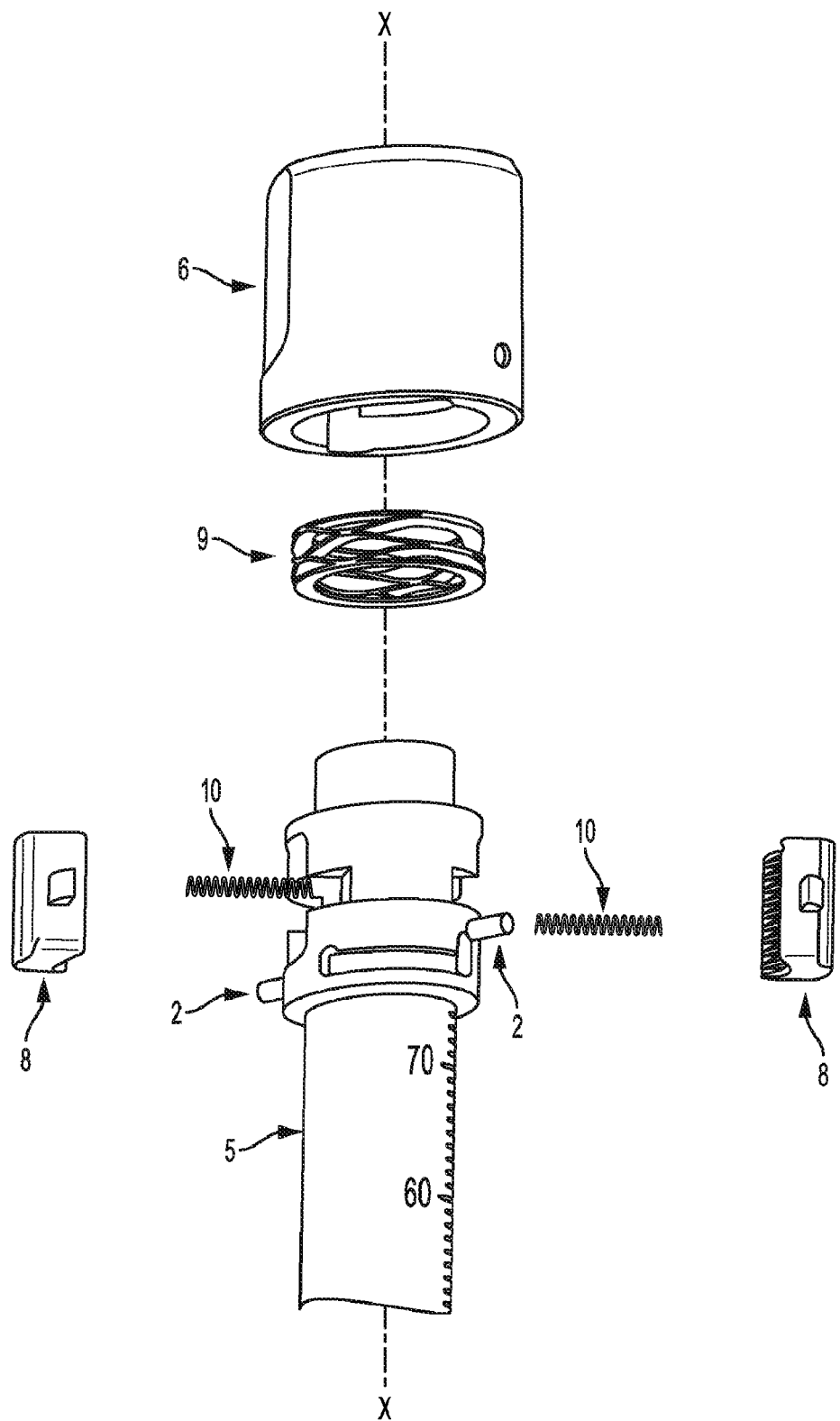
FIG. 11 is an exploded view of a release mechanism of a strut body of a strut assembly of the external bone fixation system of FIG. 1.

As shown in FIG. 11, the actuation of at least one threaded key 8 may be accomplished via rotation (e.g., manual rotation, potentially about the axis X-X) of an outer sleeve 6. The at least one threaded key 8 maybe provided within at least one corresponding opening in the strut body 5, and the outer sleeve 6 may be provided about the at least one threaded key 8, the strut body 5 and the threaded rod assembly 25 via an eccentric bore. The eccentric bore may include a camming surface such that when the sleeve 6 is rotated (e.g., about the axis X-X), the camming surface that either allows the at least one threaded key 8 to move away from and out of engagement with the threaded rod assembly 25 via a corresponding resilient member 10 or forces the at least one threaded key 8 into engagement with the threaded rod assembly 25 (i.e., the first strut screw 12 and/or the second add-on strut screw 13). As also shown in FIG. 11, the strut assemblies 110 may also include at least one radial pin 2 provided with a corresponding slot and the sleeve 6 which thereby controls the positioning of the sleeve 6 relative to the strut body 5. The at least one slot may include at least one axially-extending indentation corresponding to the position of the at least one pin 2 (and thereby the sleeve 6 itself) in which the at least one threaded key 8 is forced into engagement with the threaded rod assembly 25 via the sleeve 6 and/or the position of the at least one pin 2 (and thereby the sleeve 6 itself) in which the at least one threaded key 8 is forced out of engagement with the threaded rod assembly 25 via the at least one spring 8. As shown in FIG. 11, the strut assemblies 110 may include a resilient member 9 configured to axially bias the sleeve 6 such that the at least one pin 2 is biased into the at least one axially-extending indentation of the at least one slot.

Rotation of the threaded rod assembly 25 relative to the strut body 5, or rotation of the strut body 5 relative to the threaded rod assembly 25, while the at least one threaded key 8 in engagement with the threaded rod assembly 25 thereby results in a forced translation of the strut body 5 relative to the threaded rod assembly 25 (or vice versa), thus lengthening or shortening the strut assembly 110. While the at least one threaded key 8 is disengaged from the threaded rod assembly 25, the threaded rod assembly 25 is free to move (axially along the axis X-X and rotationally about the axis X-X) within the strut body 5 such that the length of strut assembly 110 can be freely and quickly adjusted.

While the at least one threaded key 8 and outer sleeve 6 of the strut body 5 allows for selective length adjustment of the struts 110 (i.e., the axial X-X length between the joint of the threaded rod assembly 25 and the joint of the strut body 5, and thereby the distance and orientation between the first and second platforms 120, 130), the system 100 may also provide for adjustment of the length (e.g., along the axis X-X) of the threaded rod assemblies 25 (and/or the strut bodies 5), and thereby the total adjustable range of the system 100. In some embodiments, the system 100 may provide for adjustment of the total potential length of the struts 110 (and/or the strut bodies 5) without detaching/disconnecting the struts 110 from the platforms 120, 130, or otherwise interfering with the functioning of the struts 110 in situ.

Figure 12:
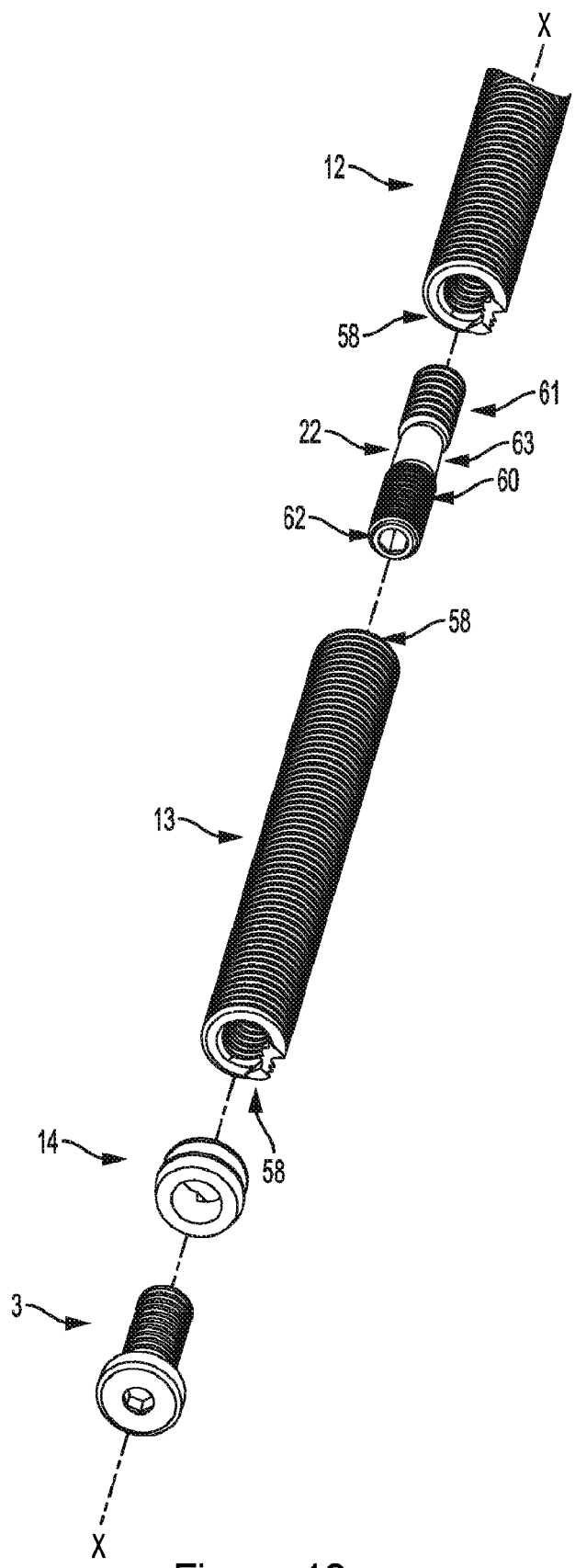
FIG. 12 is an exploded view of a pre-installed rod portion, a connection element and an add-on rod portion.
Figure 13:
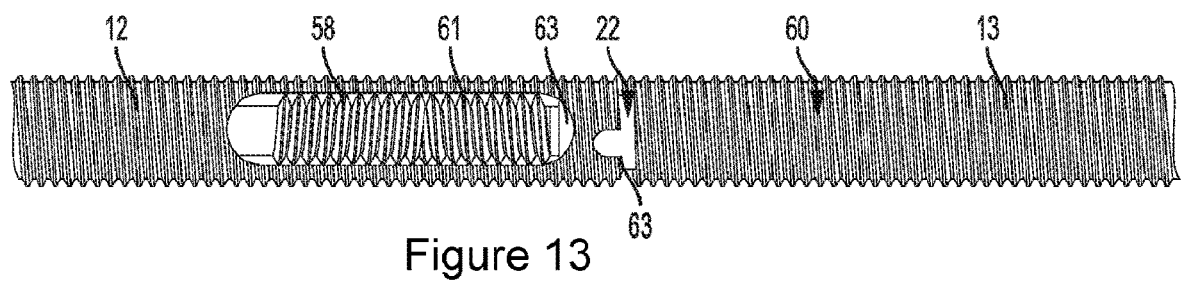
FIGS. 13-17 illustrate the connection element progressively coupling the pre-installed rod portion and the add-on rod portion of FIG. 12.

As shown in FIGS. 12 and 13, in some embodiments the system 100 may provide for selective lengthening of the threaded rod assemblies 25 without detaching/disconnecting the struts 110 from the platforms 120, 130 or otherwise interfering with the functioning of the struts 110 in situ. For example, the first strut screw 12 of the threaded rod assemblies 25 shown in FIGS. 1-11 has been lengthened by the second add-on strut screw or rod 13, as shown in FIG. 11. The threaded rod assemblies 25 may be lengthened through the use of at least one add-on threaded rod 13 that includes external threads substantially the same as the external threads of the pre-existing component(s) of the threaded rod assemblies 25 (the first strut screw 12), and may otherwise be substantially similar to the pre-existing component(s) of the threaded rod assemblies 25. For example, the at least one add-on threaded rod 13 may include the same thread pitch as the external threads of the first strut screw 12 of the threaded rod assemblies 25. The at least one add-on threaded rod 13 (and/or the pre-existing component of the threaded rod assemblies 25 forming the free end thereof—such as the first strut screw 12) may include an end configuration that ensures the clocking of the respective thread pitches such that the composite pitch remains continuous across the joined rods.

The threaded rod assemblies 25 may be lengthened via the add-on threaded rod 13 via several methodologies. In one example (not shown), the threaded rods of the threaded rod assemblies 25 may include a cap screw arranged concentrically and placed within a central channel of the add-on threaded rod 13. The add-on threaded rod 13 can be configured such that the cap screw extends out the end of the add-on threaded rod 13, but the head of the cap screw is maintained or captured within the cavity. The existing first threaded rod 12 may include a concentric taped hole to threadably couple with the exposed portion of the cap screw. To accept an additional add-on threaded rod 13 to further lengthen the threaded rod assemblies 25, the pre-installed add-on threaded rod 13 may be configured to accept a threaded insert behind the captured cap screw within the cavity. The threaded insert may include the concentric taped hole for accepting the cap screw of the next add-on threaded rod 13. In such a manner, any number of add-on threaded rods 13 may be added to the threaded rod assemblies 25 in situ.

As another example (not shown), a threaded turnbuckle may be utilized as a connecting element between the in situ or pre-installed threaded rod (e.g., the first threaded rod 12 of a previously installed add-on threaded rod 13) and an add-on threaded rod 13. The threaded turnbuckle be configured to threadably engage with internal threads of central channels of the pre-installed threaded rod, such as the first threaded rod 12, and the add-on threaded rod 13. The turnbuckle may include a first portion with right hand sense external threads and a second portion with left hand sense external threads. The turnbuckle may also include a socket or another suitable driving feature incorporated into one end configured for providing a means of torque transmission to the turnbuckle. In such an embodiment, the internal threads of the in situ or pre-installed threaded rod can include a thread pitch whose sense was the same as the one on the opposite end of the driving feature of the turnbuckle, with the add-on threaded rod 13 having the same thread sense as the end of the turnbuckle having the driving feature. A drive element can be inserted down the central channel in the add-on threaded rod 13 and engaged with the driving feature of the turnbuckle. The add-on threaded rod 13, while on the shaft of the driving element and the driving feature of the turnbuckle engaged with the drive element, can be placed coaxial to the in situ or pre-installed threaded rod and the turnbuckle torqued to thread into both the in situ or pre-installed threaded rod and the add-on threaded rod 13 at the same time. Thread clocking of the external threads of the in situ or pre-installed threaded rod and the add-on threaded rod 13 may be achieved by inter digitation features at the mating ends of the in situ or pre-installed threaded rod and the add-on threaded rod 13.

As another example, the system 100 may include a turnbuckle connecting element 22 that provides or allows for some means of pre-assembly such that the add-on threaded rod 13 and the connecting element 22 does not need to be separately handled during installation, as shown in FIGS. 11 and 12. Similar to the turnbuckle described above, the connecting element 22 may be configured to threadably engage with internal threads 58 of central channels of the pre-installed threaded rod, such as the first threaded rod 12, and the add-on threaded rod 13. The connecting element 22 may include a first portion 60 with external threads of a first pitch and a second portion 61 with external threads of a second pitch that is different than the first pitch. For example, the first pitch may be fine thread pitch and the second pitch may be a coarse thread pitch (or vice versa). While the pitch of the external threads of the first and second portions 60, 61 may differ, the sense of the threads may be same. As such, the internal threads 58 of the pre-installed threaded rod 12 may include the first pitch or the second pitch (and the corresponding thread sense) at least at a first end thereof, and the internal threads 58 of the add-on threaded rod 13 may include the other of the first pitch or the second pitch (and the corresponding thread sense) at least at a first end thereof.

The internal threads of the second end of the add-on threaded rod 13 opposing the first end thereof may include the same thread pitch as the first end of the other of the first pitch or the second pitch. The second end of the add-on threaded rod 13 may thereby allow for an additional add-on threaded rod 13 to be installed to further lengthen the threaded rod assemblies 25, and thereby the further increase the range of the threaded rod assemblies 25 in situ.

In some embodiments, the internal threads 58 of the pre-installed threaded rod 12 may include a coarse thread pitch, and the internal threads 58 of the add-on threaded rod 13 may include a fine thread pitch (or vice versa). In such embodiments, if the connecting element 22 is torqued a first rotational direction and correspondingly threadably engaged with the internal threads 58 of the pre-installed threaded rod 12 and the add-on threaded rod 13, the connecting element 22 would progress out of the add-on rod 13 at a given rate as it rotated, while it would progress into the pre-installed threaded rod 12 at a relatively faster rate—thus differentially bringing the add-on threaded rod 13 into contact with the pre-installed threaded rod 12. The connecting element 22 may include a socket or another suitable driving feature 62 incorporated into one end configured for providing such torque transmission to the connecting element 22 (via through the channel of the pre-installed threaded rod 12, for example).

In this way, the connecting element 22 may be utilized to couple the add-on threaded rod 13 to the pre-installed threaded rod 12 without disconnecting or otherwise interfering with the pre-installed threaded rod 12 (i.e., can be installed in situ). In some embodiments, the connecting element 22 may be threaded into engagement with the add-on threaded rod 13, and the add-on threaded rod 13 may include finer pitched internal threads than the pre-installed threaded rod 12 (or vice versa). As shown in FIG. 12, the connecting element 22 may include a non-threaded region 63 between the first and second portions 60, 61. The non-threaded region 63 may allow for the finer pitch threaded portion 60 or 61 of the connecting element 22 to initially be partially over-threaded into whichever of the add-on threaded rod 13 and the pre-installed threaded rod 12 includes the finer pitched internal threads.

For example, FIGS. 13-17 being utilized to bring together and couple the first pre-installed threaded rod 12 and the second or add-on threaded rod 13. As noted above, although two threaded rods of an external bone fixation system are being utilized to illustrate one exemplary use of the connecting element 22, the connecting element 22 may be utilized to bring together (or space apart) and couple any two members or portions (whether part of an external bone fixation system or part of another orthopedic or non-orthopedic mechanism or system). Further, although the connecting element 22 is depicted and described as having external threads 60, 61 and the first and second rod 12, 13 as having mating internal threads, the connecting element 22 may have internal threads and the members may have external threads.

Figure 14:
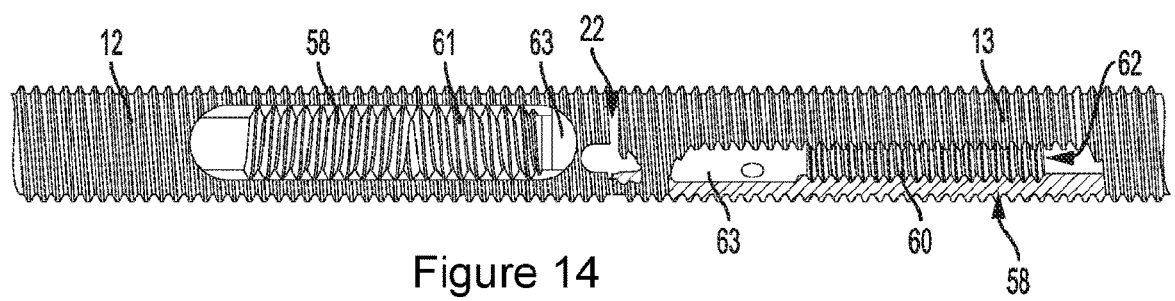
Figure 15:
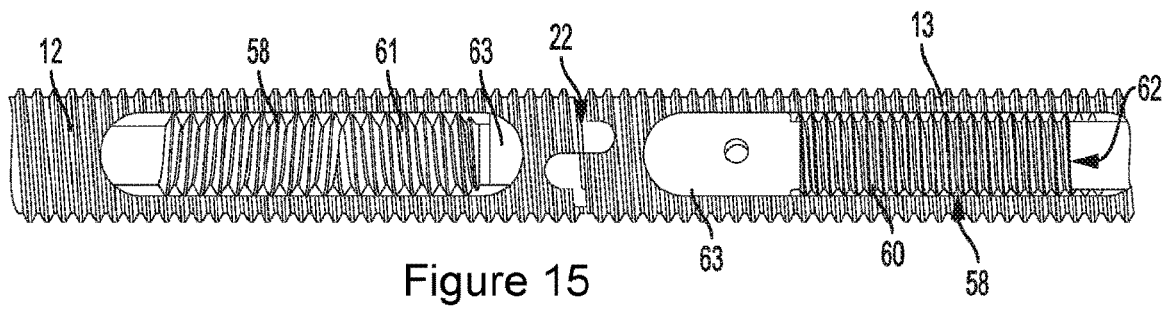
Figure 16:
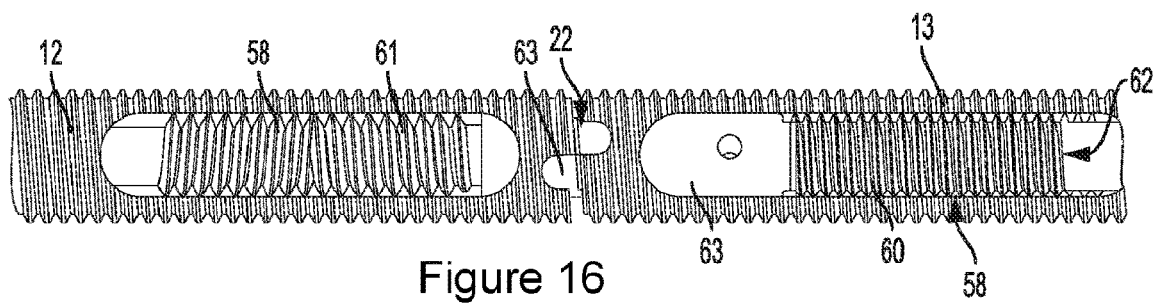
Figure 17:
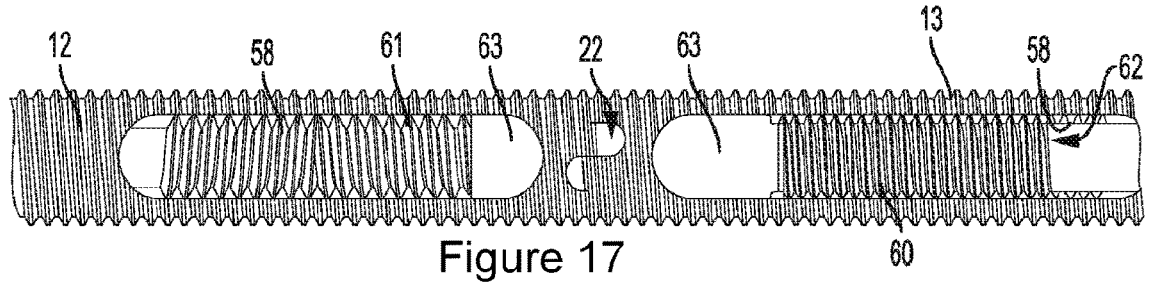

As shown in FIGS. 13 and 14, initially the second rod or member 13 and the connecting element 22 may be threadably coupled via relatively fine pitch threads and rotated or torqued together (e.g., via a tool) to threadably engage the first rod or member 12 via relatively course pitch threads. In such an embodiment, the non-threaded portion 63 of the connecting element 22 may extend between the first and second rods or members 12, 13. As shown in FIG. 14, the second rod or member 13 and the connecting element 22 may be rotated together as a unit until the first and second rods or members 12, 13 meet such that relatively rotation between the first and second rods or members 12, 13 is prevented. As shown in FIGS. 15 and 16, the connecting element 22 may be further rotated therefrom such that the connecting element 22 travels axially through the first and second rods or members 12, 13. However, due to the finer pitch of the threaded connection between the connecting element 22 and the second rod or member 13 than the threaded connection between the connecting element 22 and the first rod or member 12, the connecting element 22 may travel slower or for a shorter distance as it is rotated through the second rod or member 13 than the first rod or member 12, as shown in FIGS. 16 and 17. In this way, the connecting element 22 may draw the first and second rods or members 12, 13 together, such as to an arrangement wherein the external threads of the first and second rods or members 12, 13 are aligned or are continuous. It is noted that the combination of the relatively fine pitch threads and the relatively fine pitch threads of the connecting element 22 and the second rod member 12 and the first rod or member 12, respectively, provides for extremely high axial accuracy or adjustment between the first and second rods or members 12, 13 that may not be able to achieved via a single thread pitch due to physical restraints (i.e., a thread pitch equating to the difference in thread pitch between the fine and course thread pitches may not be realistically physically achievable).

The connecting element 22 may be provided or otherwise pre-installed with the add-on threaded rod 13 before being coupled with the pre-installed threaded rod 12. To make the most efficient use of the engaged threads of the connecting element 22 within the add-on threaded rod 13, the add-on threaded rod 13 and/or the connecting element 22 may be configured such that the add-on threaded rod 13 and the connecting element 22 are rotated together as the connecting element 22 is threaded into the pre-installed threaded rod 12.

Figure 18:
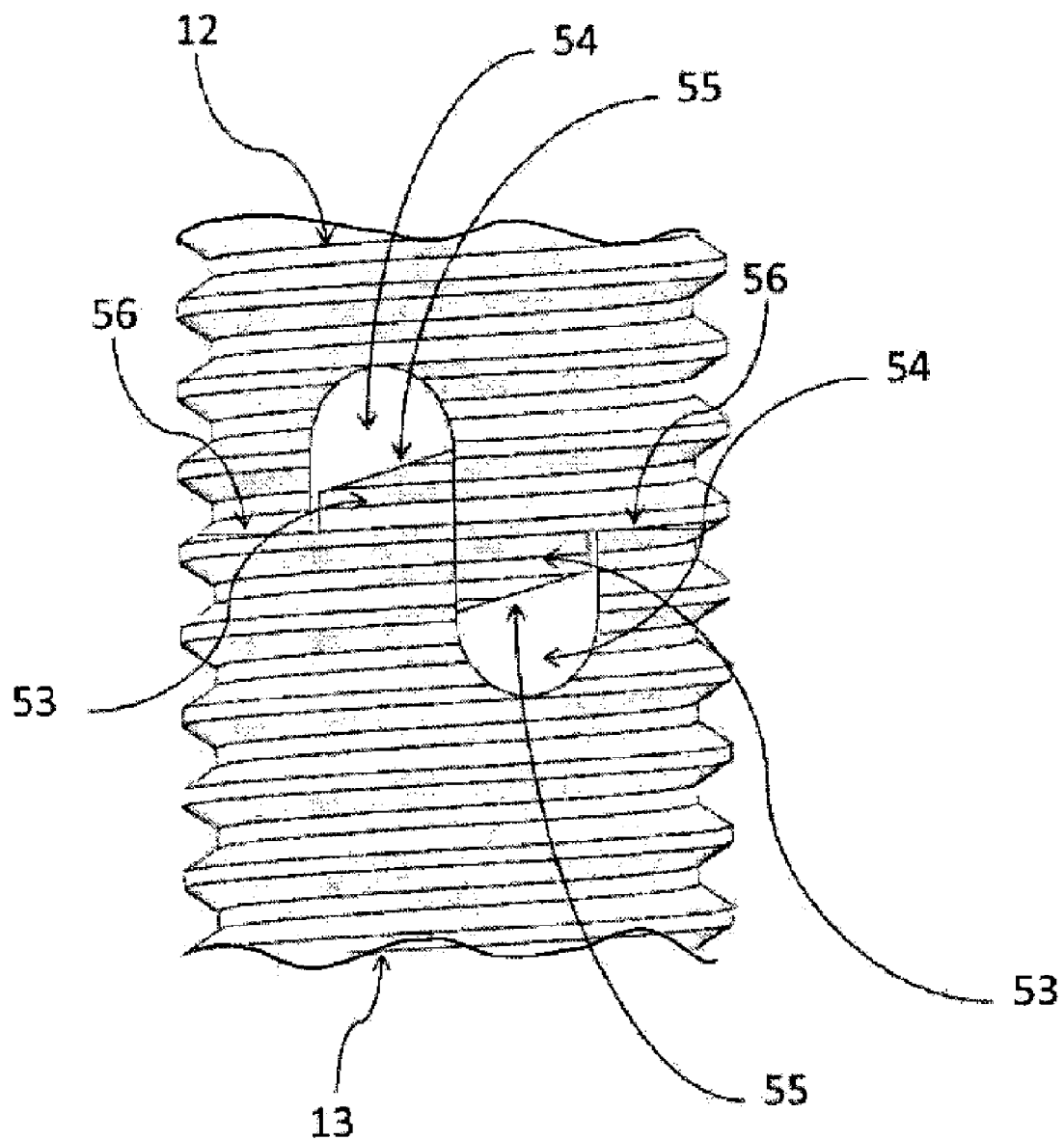
FIG. 18 is a detailed view of the timing geometry for the pre-installed rod portion and the add-on rod portion of FIG. 12.

As shown in FIG. 18, at least the free end of the pre-installed threaded rod 12 and the ends of the add-on threaded rod 13 may include a keying element 53 that ensures the correct timing between the external threads the pre-installed threaded rod 12 and the ends of the add-on threaded rod 13. In use, the first portion 60 of the connecting element 22 may be pre-installed within the channel of the add-on threaded rod 13, and the second portion 61 of the connecting element 22 may thereby extend from the add-on threaded rod 13. The add-on threaded rod 13 and the connecting element 22 may be torqued (e.g., rotated together as a unit) such that the second portion 61 of the connecting element 22 threadably engages the internal threads of the cavity 28 of the pre-installed threaded rod 12, and thereby travel axially into the pre-installed threaded rod 12 and draw the add-on threaded rod 13 and the pre-installed threaded rod 12 together. The keying elements 53 of the add-on threaded rod 13 and the pre-installed threaded rod 12 may be configured such that when mating faces thereof are within an optimal distance of one another, the mating faces of the keying elements 53 contact one another and prevent relative rotation between the add-on threaded rod 13 and the pre-installed threaded rod 12, as shown in FIG. 18.

As also shown in FIG. 18, in such an embodiment the keying elements 53 of the add-on threaded rod 13 and the pre-installed threaded rod 12 may include recesses 54 corresponding to the mating faces that allow for relative axial translation between the add-on threaded rod 13 and the pre-installed threaded rod 12. In such a state, the driving feature 62 of the connecting element 22 may be engaged via the channel of the add-on threaded rod 13 and rotated such that the connecting element 22 threadably translates through the cavities of the add-on threaded rod 13 and the pre-installed threaded rod 12 at different rates to thereby axial translate the add-on threaded rod 13 and the pre-installed threaded rod 12 towards one another. The connecting element 22 may be torqued until mating end faces 56 of the add-on threaded rod 13 and the pre-installed threaded rod 12 contact each other, as shown in FIG. 18. The add-on threaded rod 13 and the pre-installed threaded rod 12 may be configured such that when the mating end faces 56 of the key elements 53 of the add-on threaded rod 13 and the pre-installed threaded rod 12 are engaged, the add-on threaded rod 13 and the pre-installed threaded rod 12 are securely or rigidly coupled and the pitch of the external threads thereof are properly clocked, as shown in FIG. 18.

The free end of the pre-installed threaded rod 12 or the free end of add-on threaded rod 13, if installed, may include a guide bushing 14 configured to mate with the keying elements 53, mating end faces 56 and/or recesses thereof, as shown in FIGS. 12-17. The guide bushing 14 may act to provide a relatively smooth surface for contact with the interior of the cavity of the strut body 5, and thereby protect the external threads thereof. As also shown in FIG. 12, a cap screw 3 may be utilized to secure the guide bushing 14 to the pre-installed threaded rod 12 or the free end of add-on threaded rod 13 if installed.

Although the connecting elements 22 are described and utilized above with respect to a first pre-installed threaded rod 12 and a second add-on threaded rod 13 of a strut assembly, it is specifically and particularly contemplated herein that the connecting elements 22 may be utilized with any other first and second members. In some embodiments, the first and second members coupled and brought together via a connecting element 22 may not be associated with a strut assembly, nor a 6 DOF bone or tissue fixation system. Stated differently, the first and second members coupled and brought together via a connecting element 22 may be any first and second members configured to couple via the connecting element 22. For example, the connecting element 22, with first and second thread portions of differing pitches separated by a non-threaded portion, may be internally threaded or externally threaded for engagement with correspondingly threaded first and second members. It is also noted that the double threaded nature of the connecting element 22, of differing pitches, provides a relatively high level of precision of axial movement between the first and second members (e.g., via the combination of the thread pitches), produces an improved mechanical advantage over other mechanisms for coupling and bringing together first and second members, produces a relatively high amount of torque, the first and second members stay tightly coupled, and the construct remains substantially unaffected by vibration.

As shown in FIGS. 3-7 and 19, the pre-installed threaded rod 12 of the threaded rod assemblies 25 of the struts 110 may include a cross pin 18 adjacent the strut body 5 that can be manually engaged and utilized to apply a torque to the threaded rod assemblies 25. In this way, assuming the strut body 5 is threadably engaged with the external threads of the threaded rod assemblies 25, the cross pin 18 can be utilized in situ to adjust the length of the struts 110, and thereby the distance and orientation between the first and second platforms 120, 130 (and, thereby, the bone or tissue segments coupled to the first and second platforms 120, 130).

Figure 19:
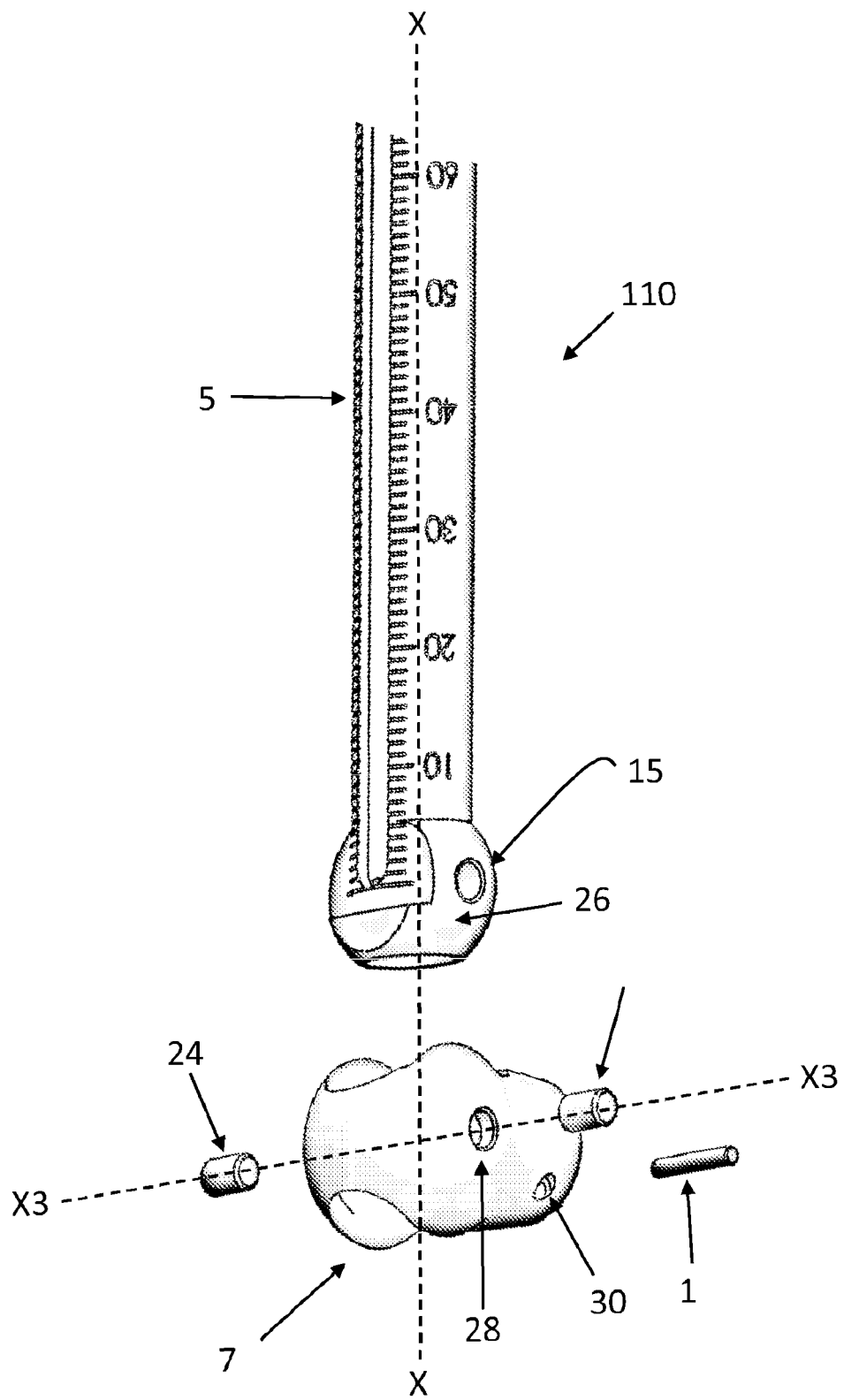
FIG. 19 is an exploded view of a joint mechanism of a strut body of a strut assembly of the external bone fixation system of FIG. 1.
Figure 20:
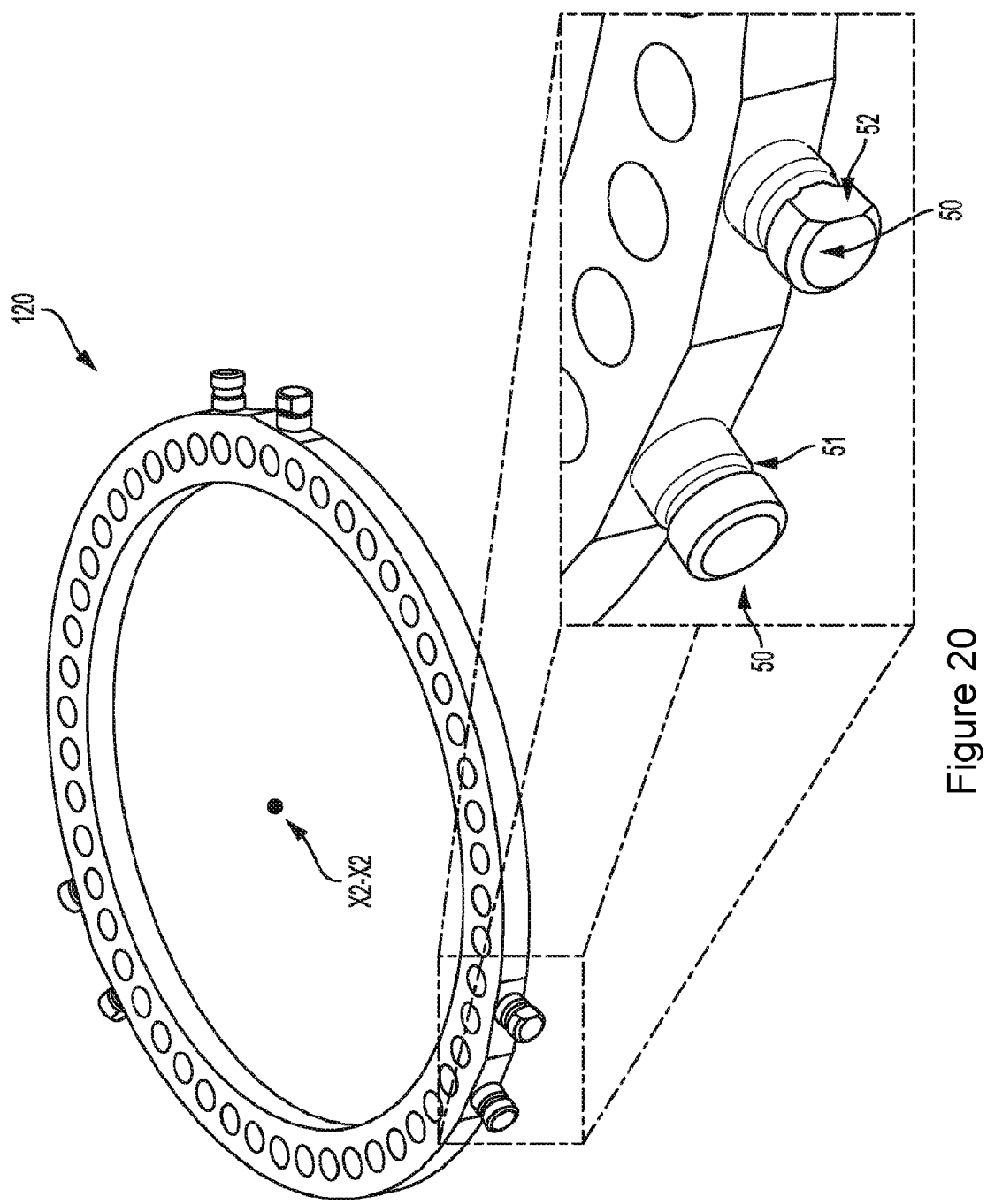
FIG. 20 illustrates perspective views of a platform of a strut assembly of the external bone fixation system of FIG. 1.
Figure 21:
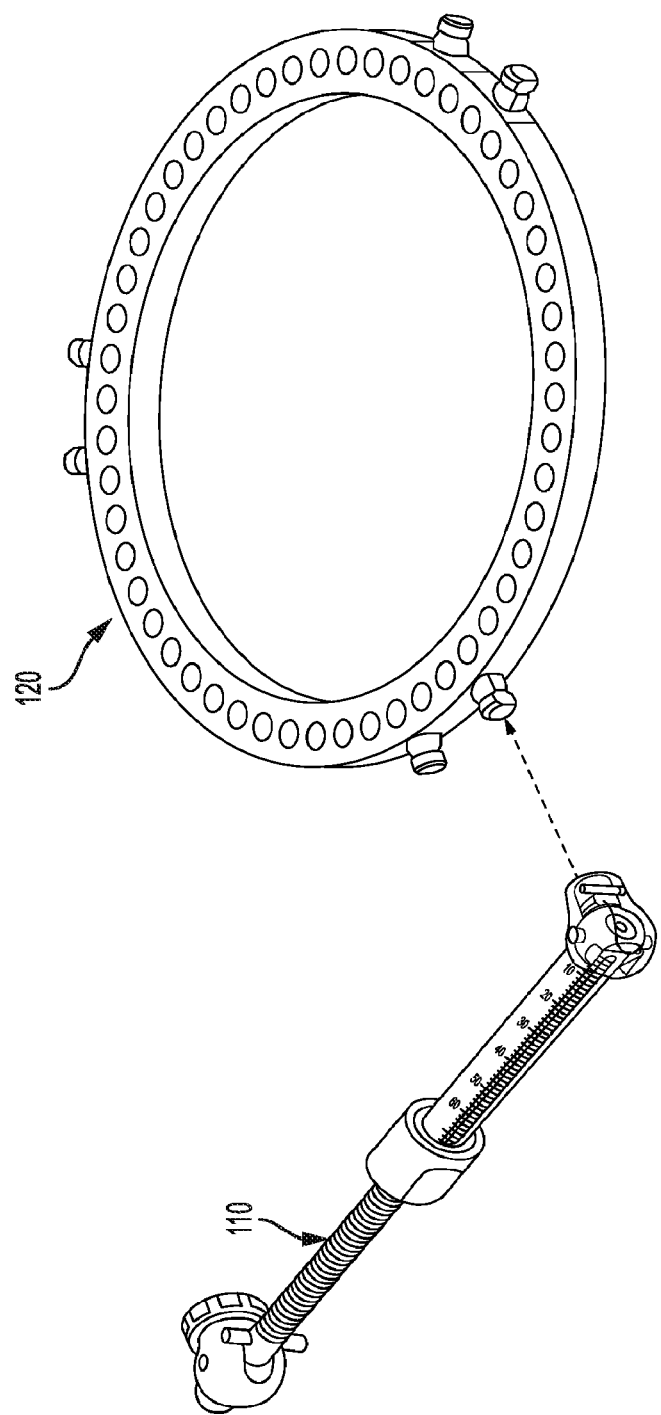
FIG. 21 is a perspective view of a strut assembly aligned with a stud of a platform in a non-operable orientation.
Figure 22:
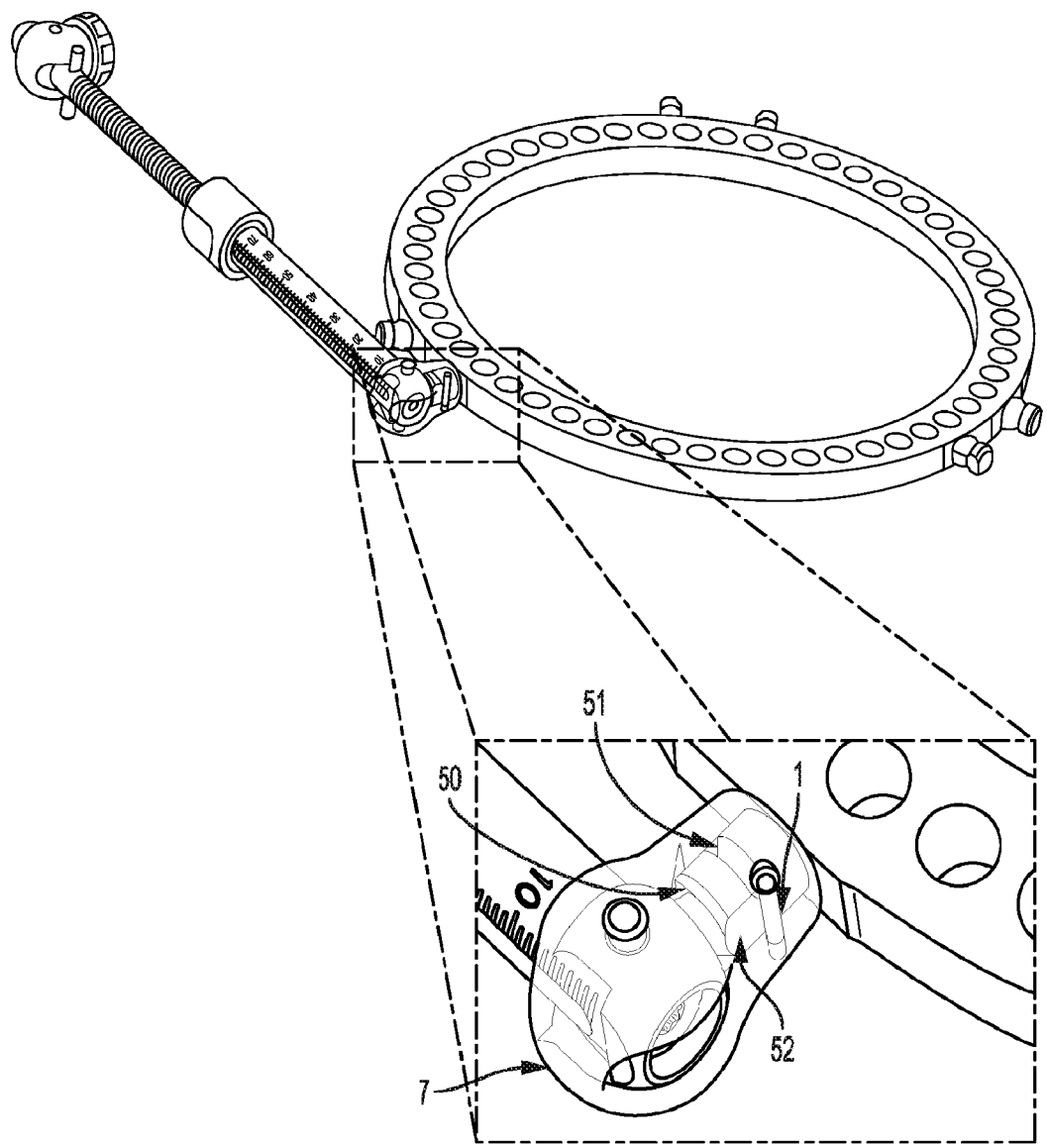
FIG. 22 is a perspective view of the strut assembly engaged with the strut of the platform in the non-operable orientation of FIG. 21.
Figure 23:
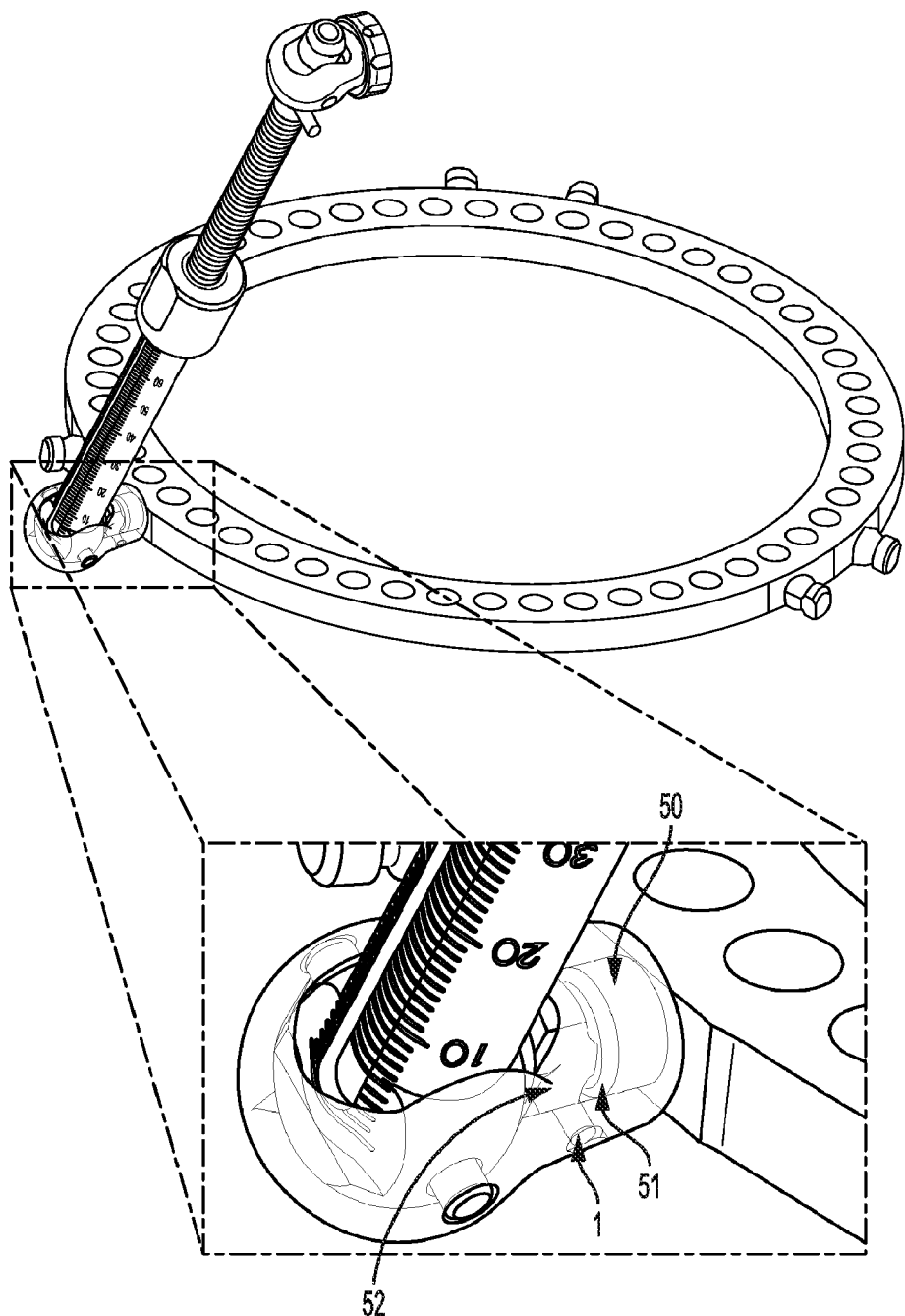
FIG. 23 is perspective view of the strut assembly coupled to the strut of the platform of FIG. 21 by rotation of the strut in to an operable orientation.
Figure 24:
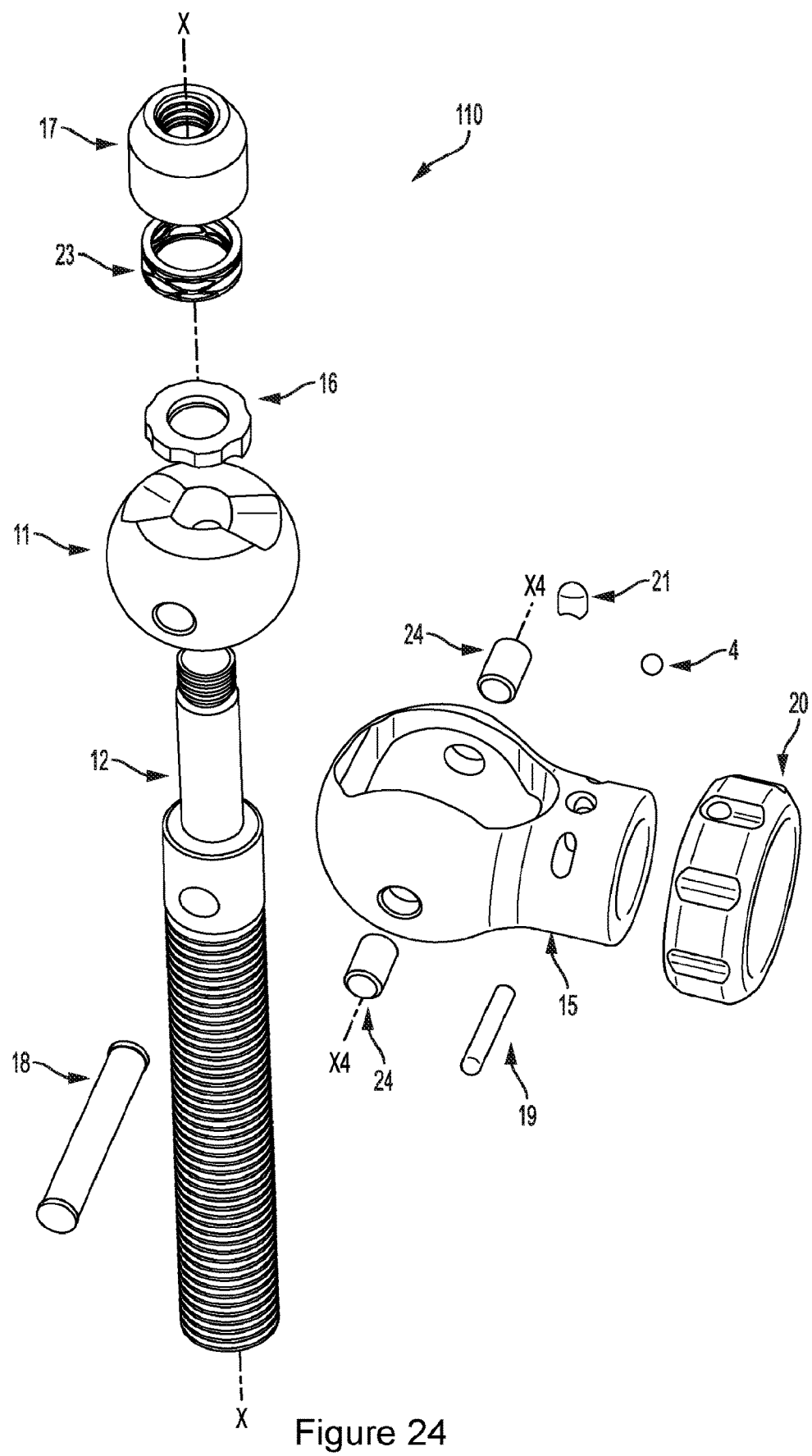
FIG. 24 is an exploded view of a joint mechanism of a threaded rod portion of a strut assembly of the external bone fixation system of FIG. 1.
Figure 25:
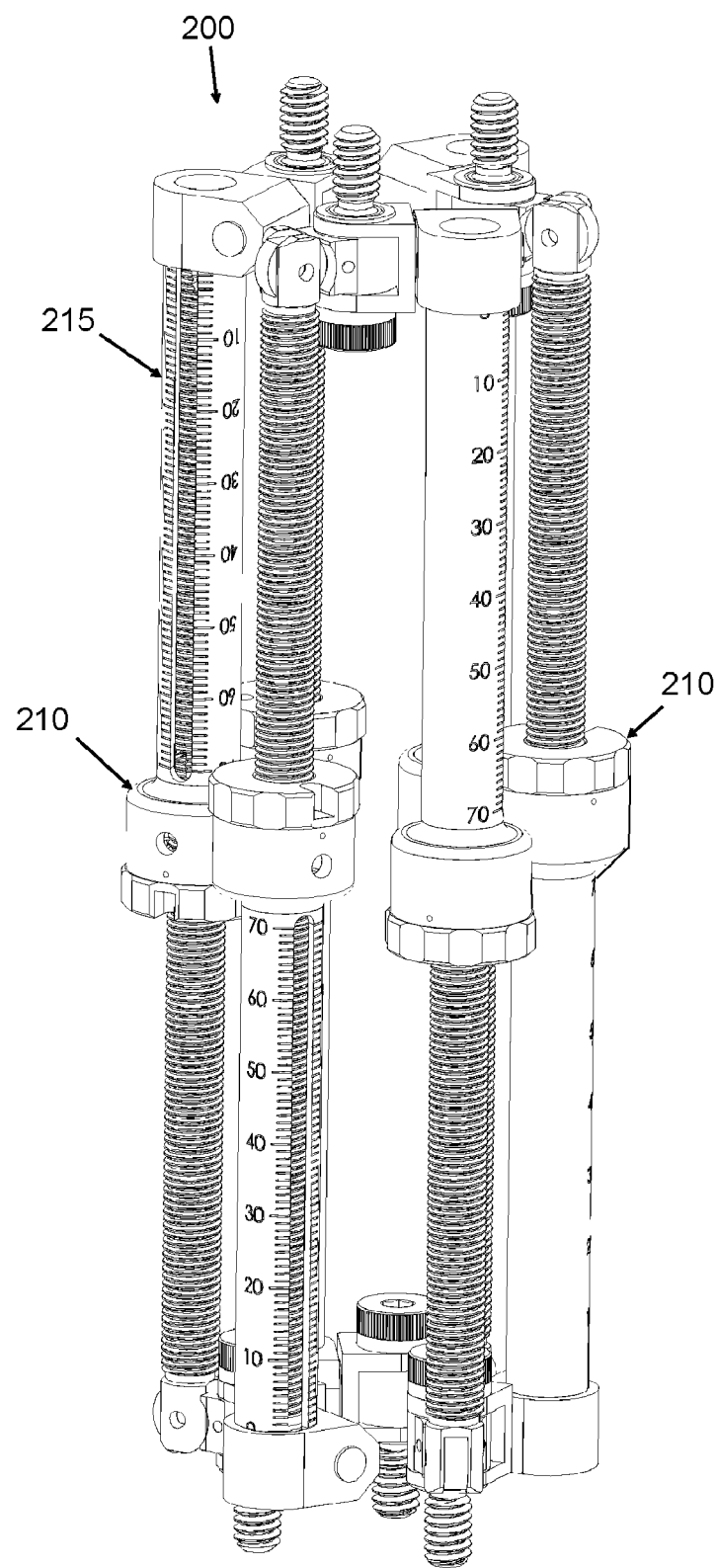
FIG. 25 is a perspective view of exemplary interconnected strut assemblies of another exemplary external bone fixation system in a first configuration according to the present disclosure.
Figure 26:
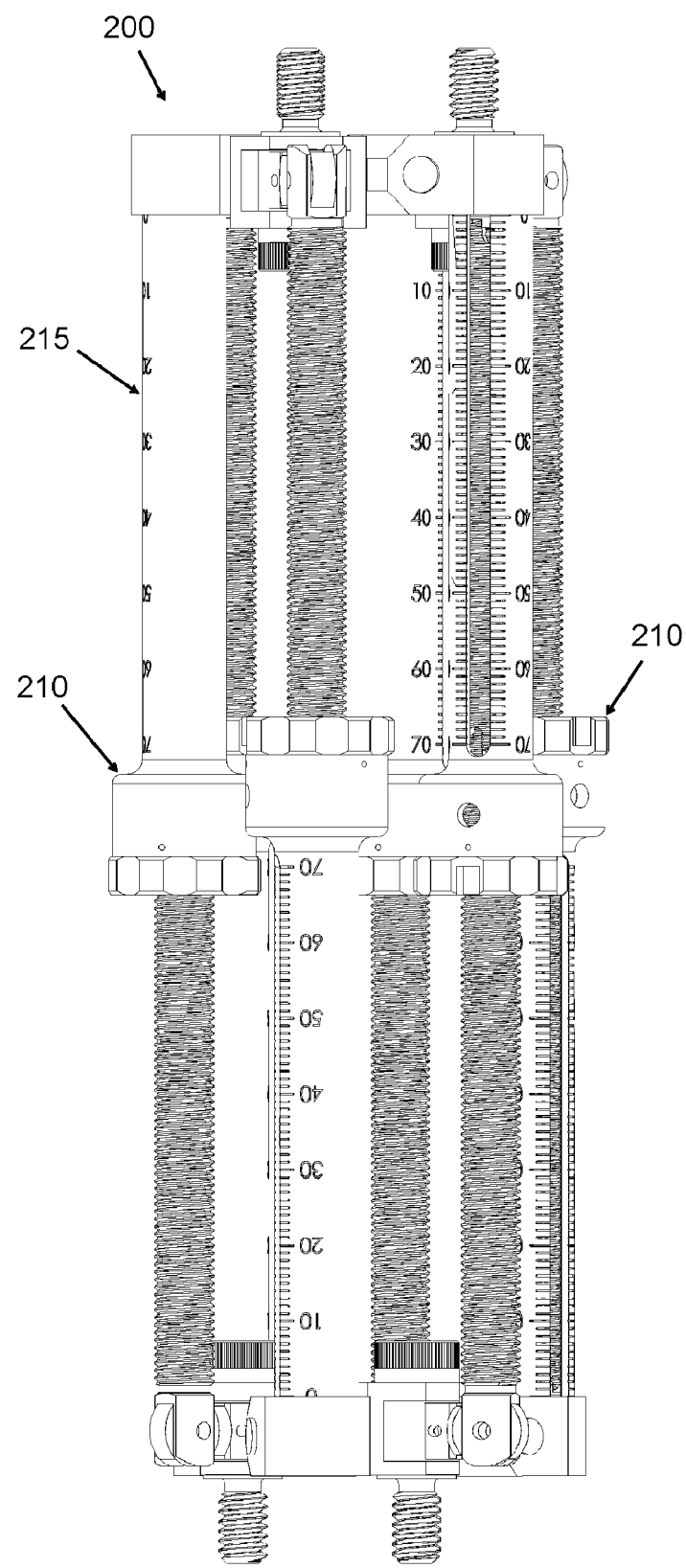
FIG. 26 is a side view of the interconnected strut assemblies of FIG. 25.
Figure 27:
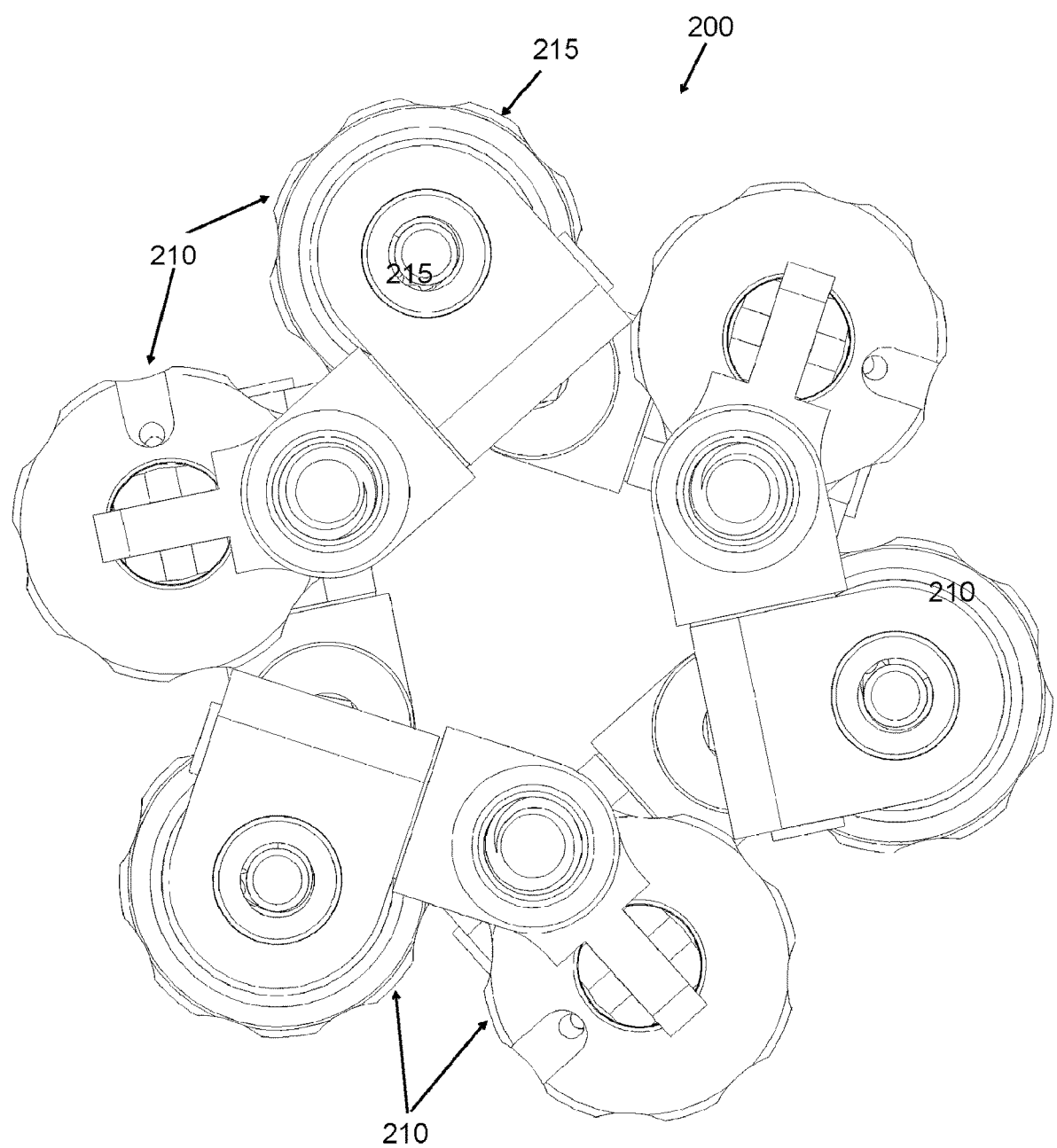
FIG. 27 is a top view of the interconnected strut assemblies of FIG. 25.
Figure 28:
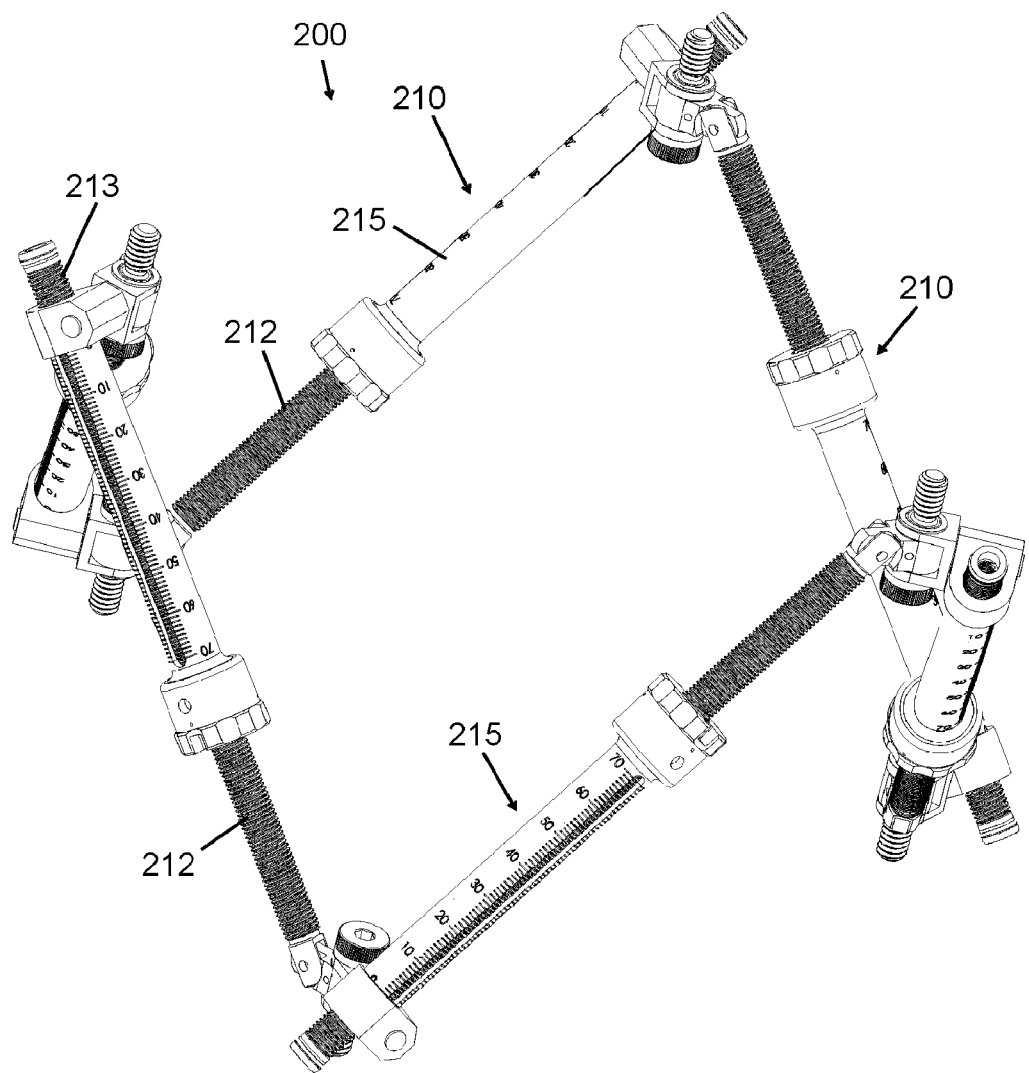
FIG. 28 is a perspective view of the interconnected strut assemblies of FIG. 25 in a second configuration.
Figure 29:
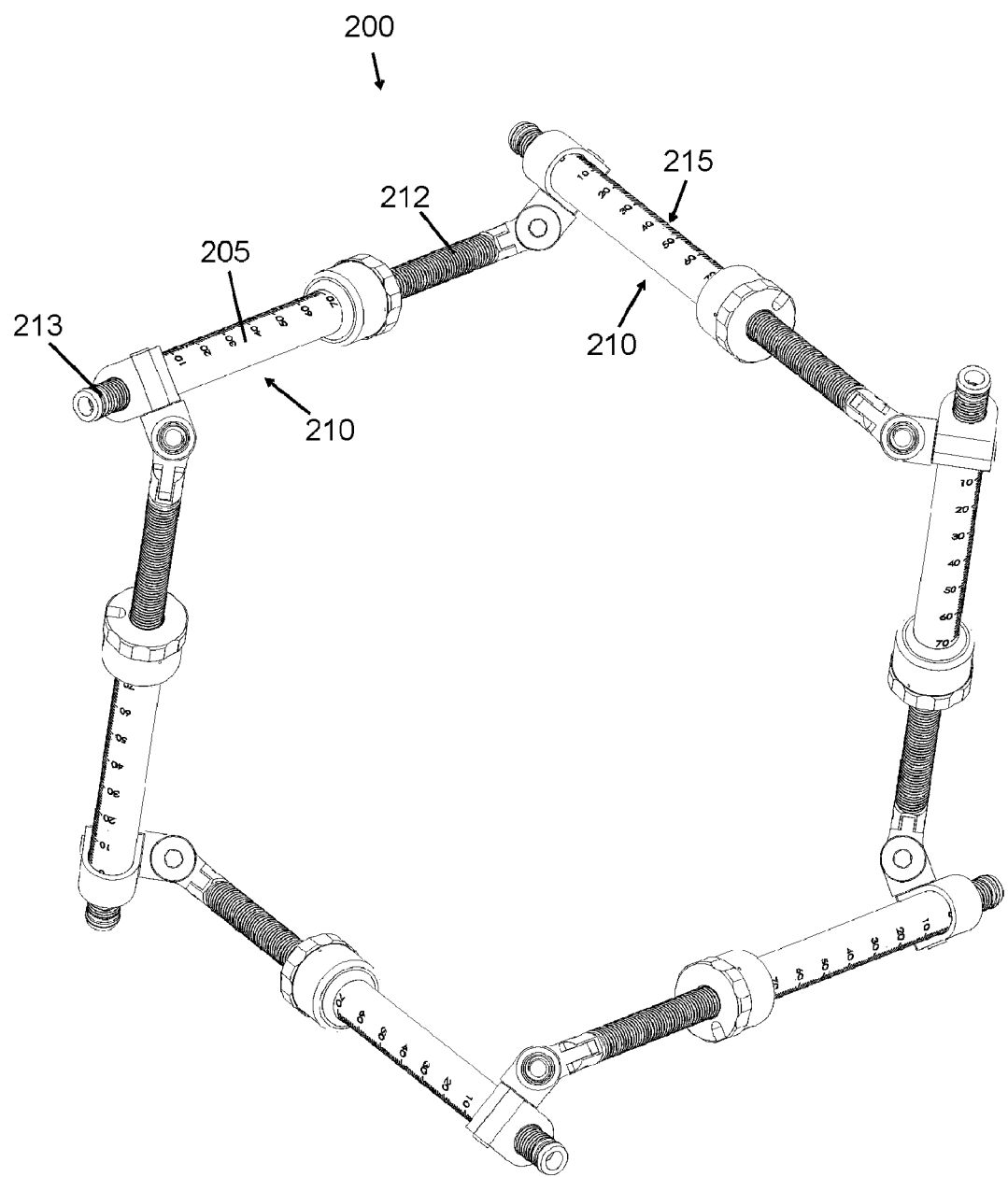
FIG. 29 is a top view of the interconnected strut assemblies of FIG. 25 in the second configuration.
Figure 30:
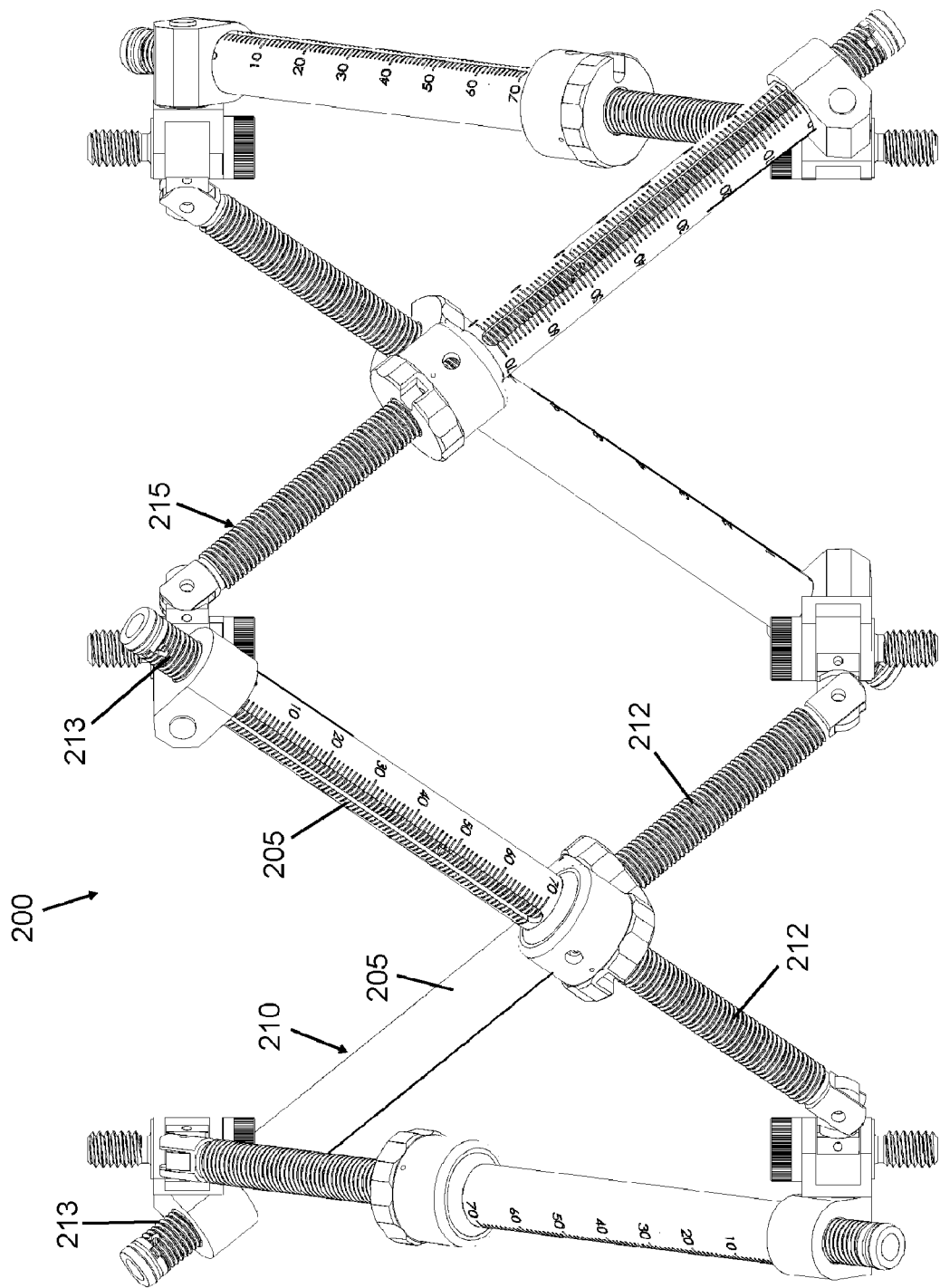
FIG. 30 is a side view of the interconnected strut assemblies of FIG. 25 in the second configuration.
Figure 31:
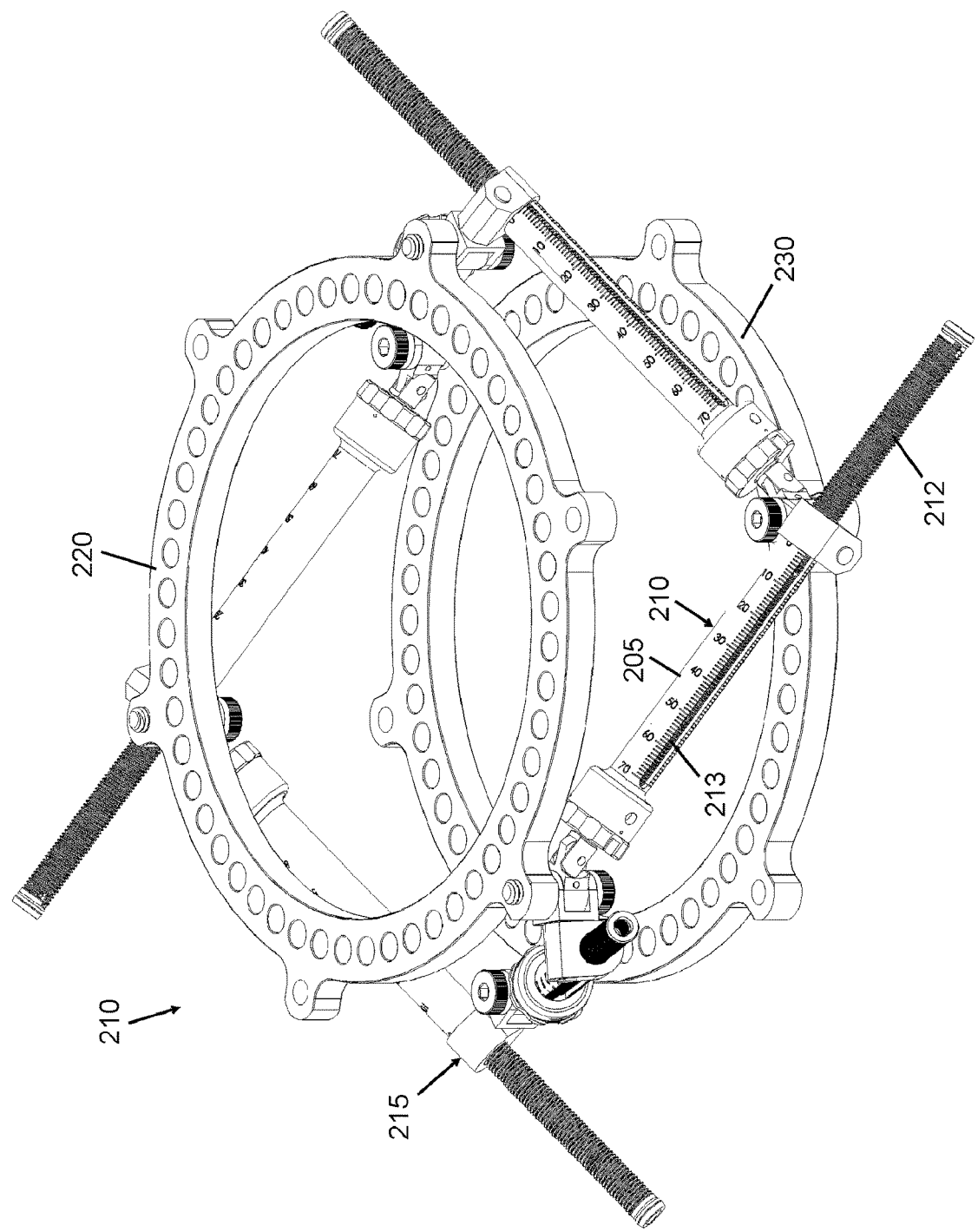
FIG. 31 is a perspective view of the interconnected strut assemblies of FIG. 25 in a collapsed third configuration and coupled to platforms of the external bone fixation system.
Figure 32:
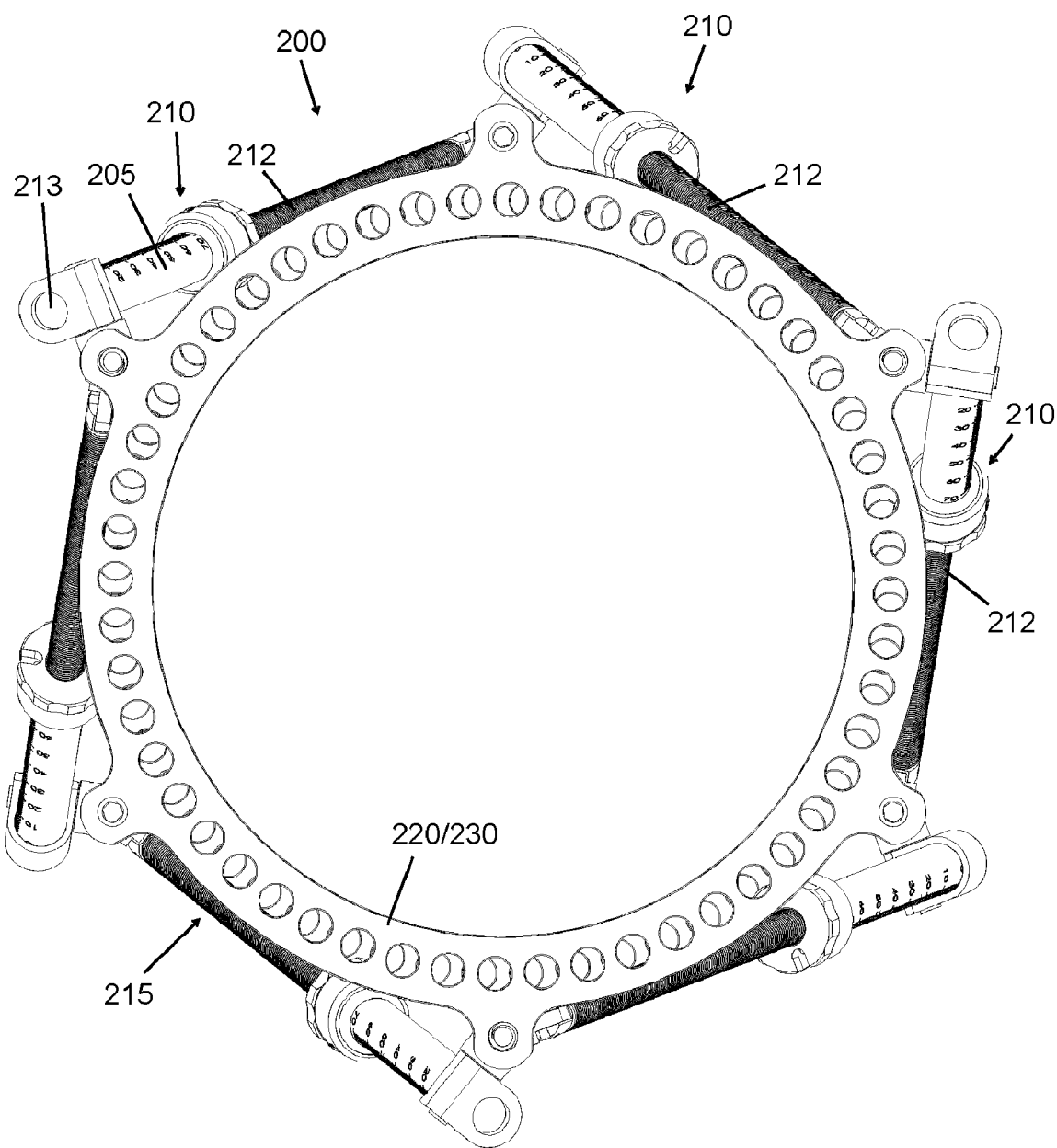
FIG. 32 is a top view of the external bone fixation system of FIG. 31.
Figure 33:
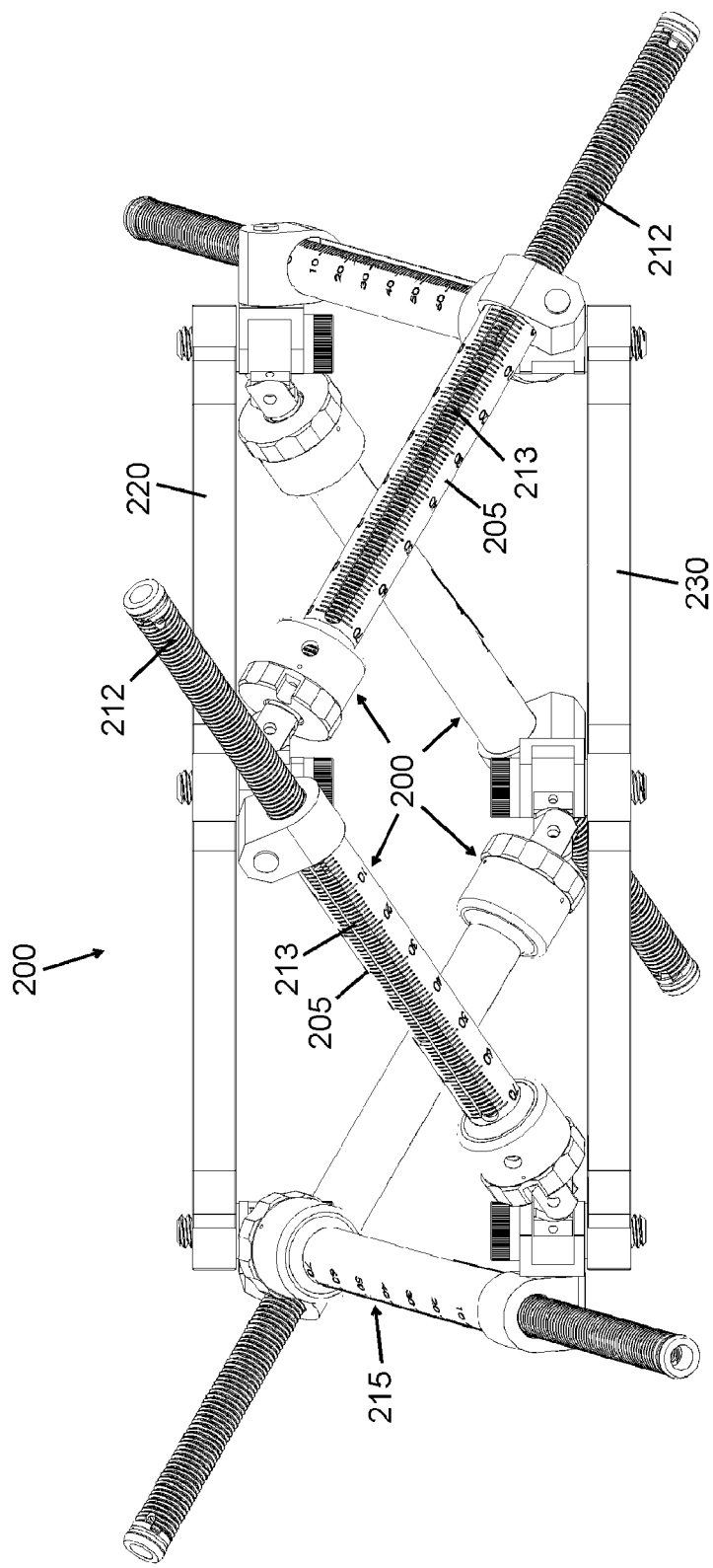
FIG. 33 is a side view of the external bone fixation system of FIG. 31.
Figure 34:
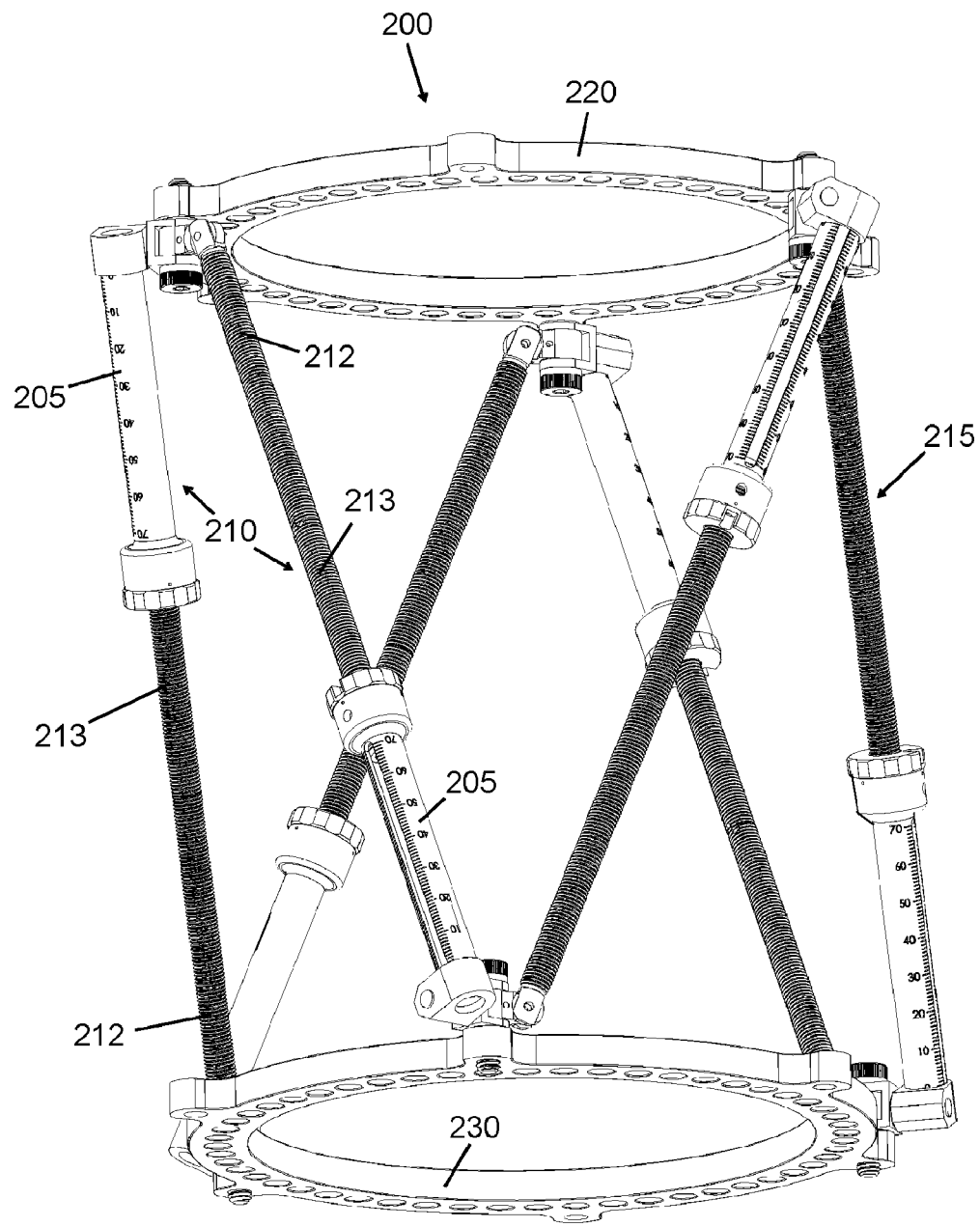
FIG. 34 is a bottom perspective view of the external bone fixation system of FIG. 31 in an extended configuration of the interconnected strut assemblies.
Figure 35:
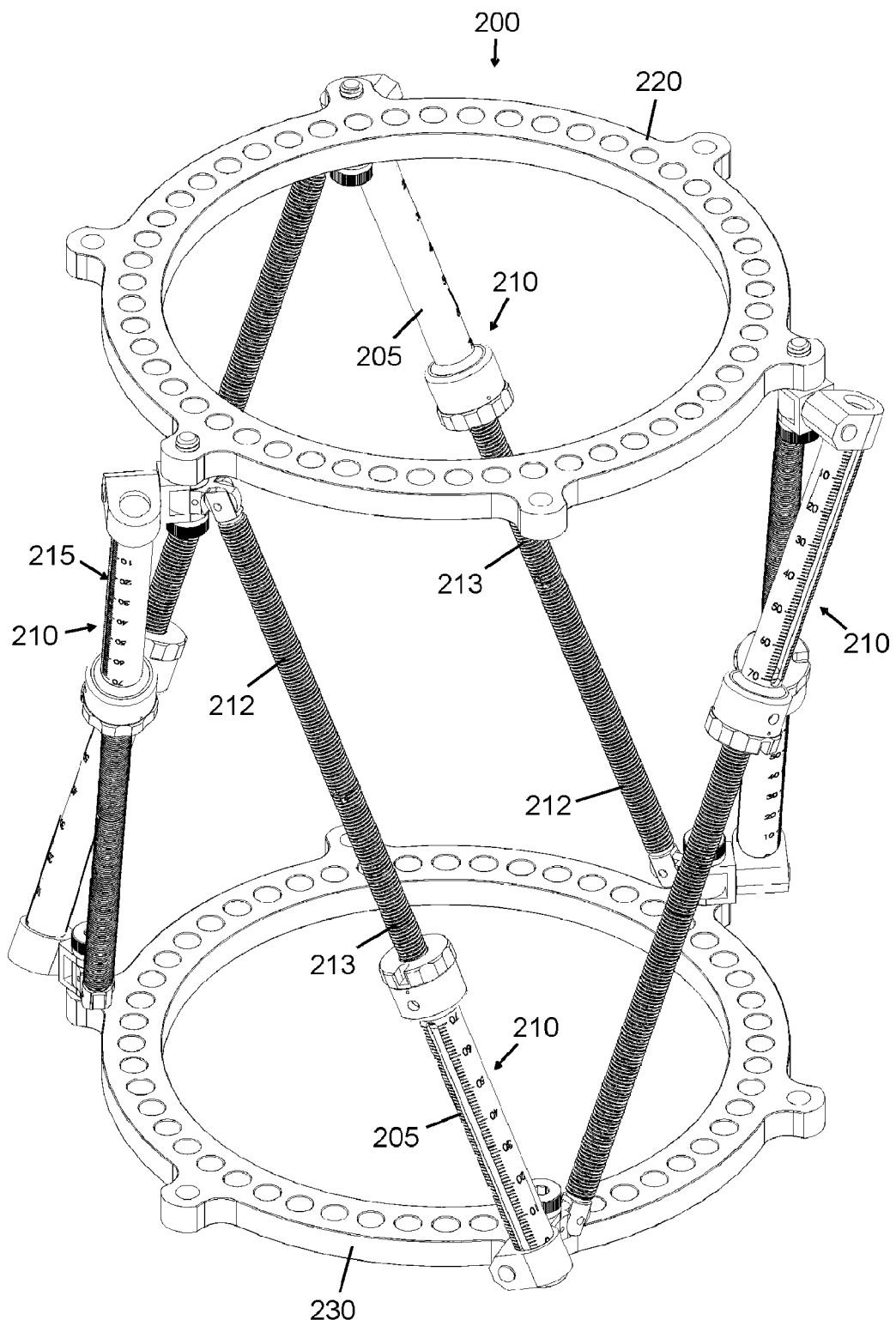
FIG. 35 is an elevational perspective view of the external bone fixation system of FIG. 33.
Figure 36:
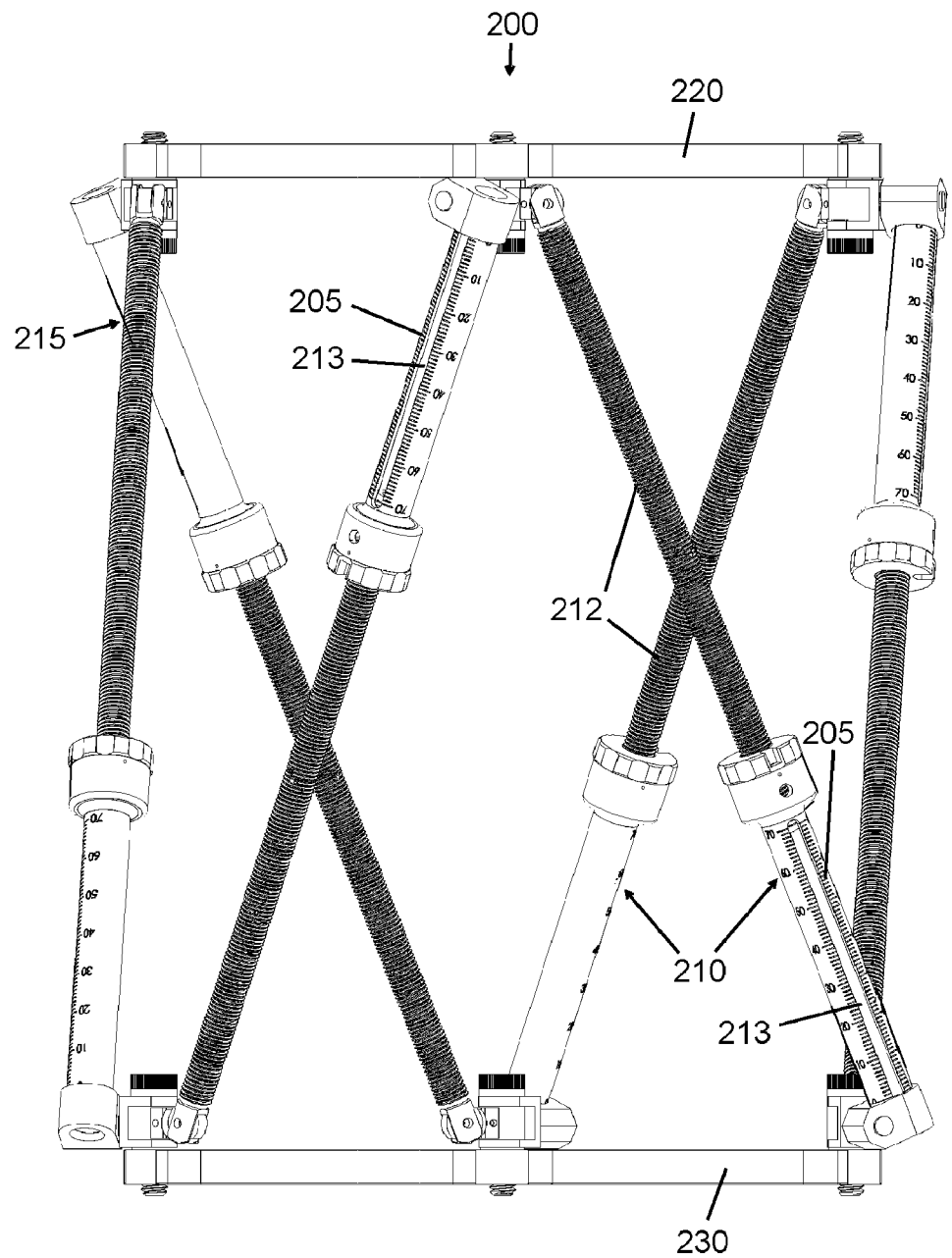
FIG. 36 is a side view of the external bone fixation system of FIG. 33.
Figure 37:
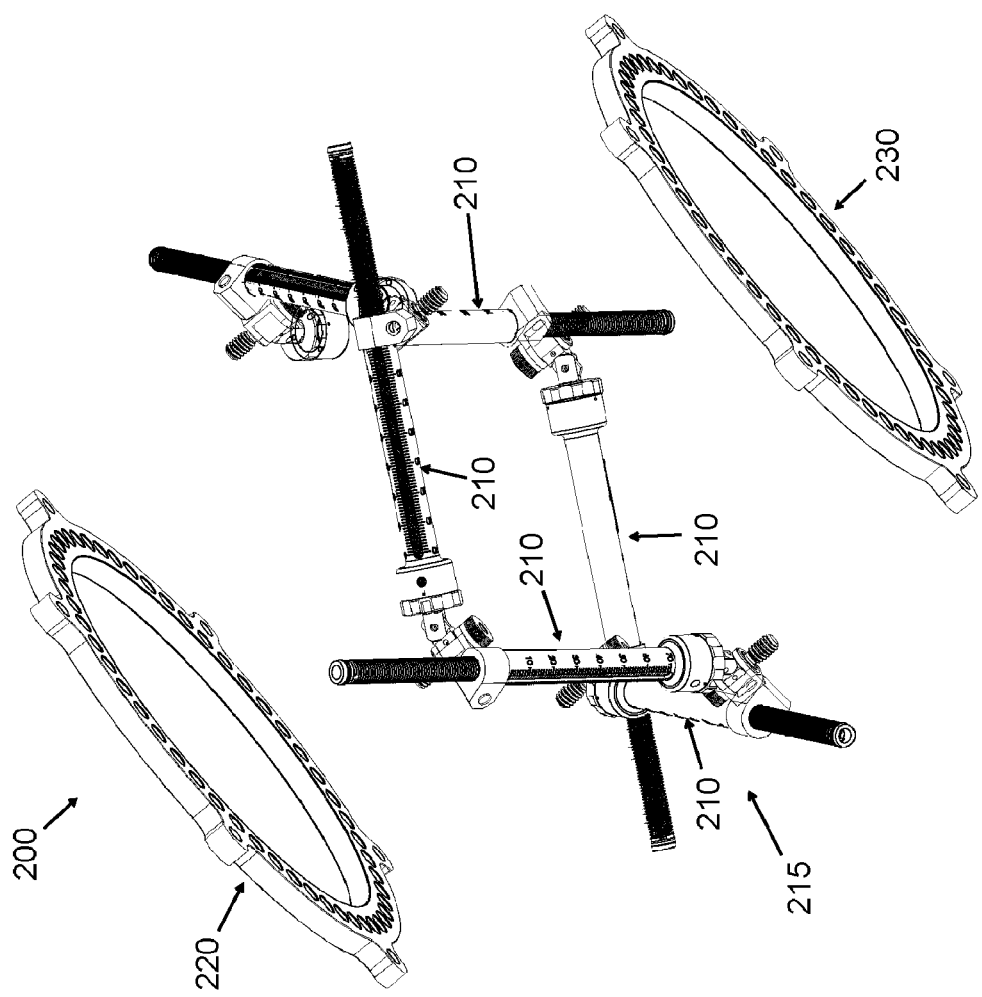
FIG. 37 is a perspective view of the interconnected strut assemblies of FIG. 25 in the third configuration and the platforms of the external bone fixation system.
Figure 38:
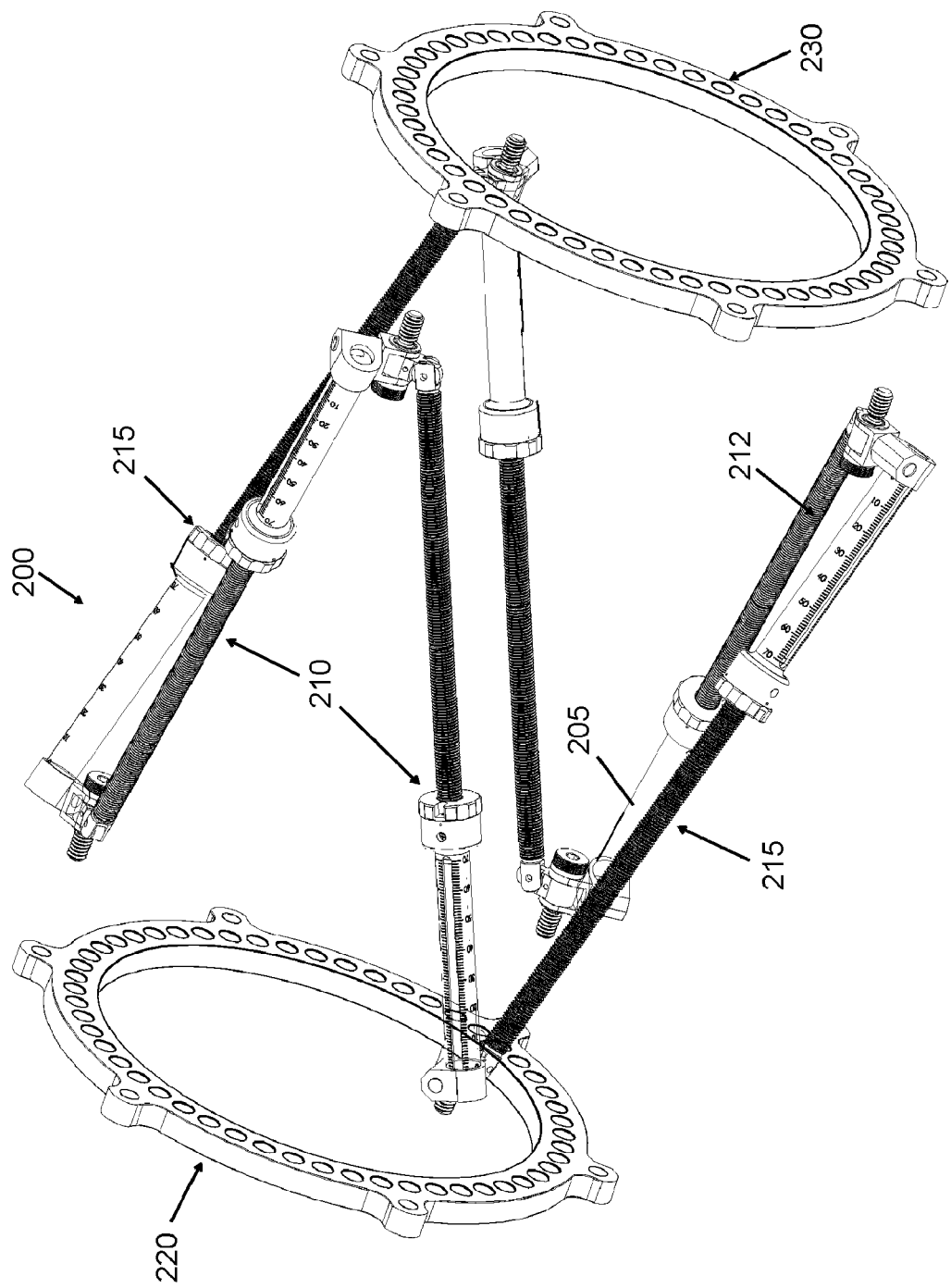
FIG. 38 is a perspective view of the interconnected strut assemblies of FIG. 25 in the extended configuration and the platforms of the external bone fixation system.
Figure 39:
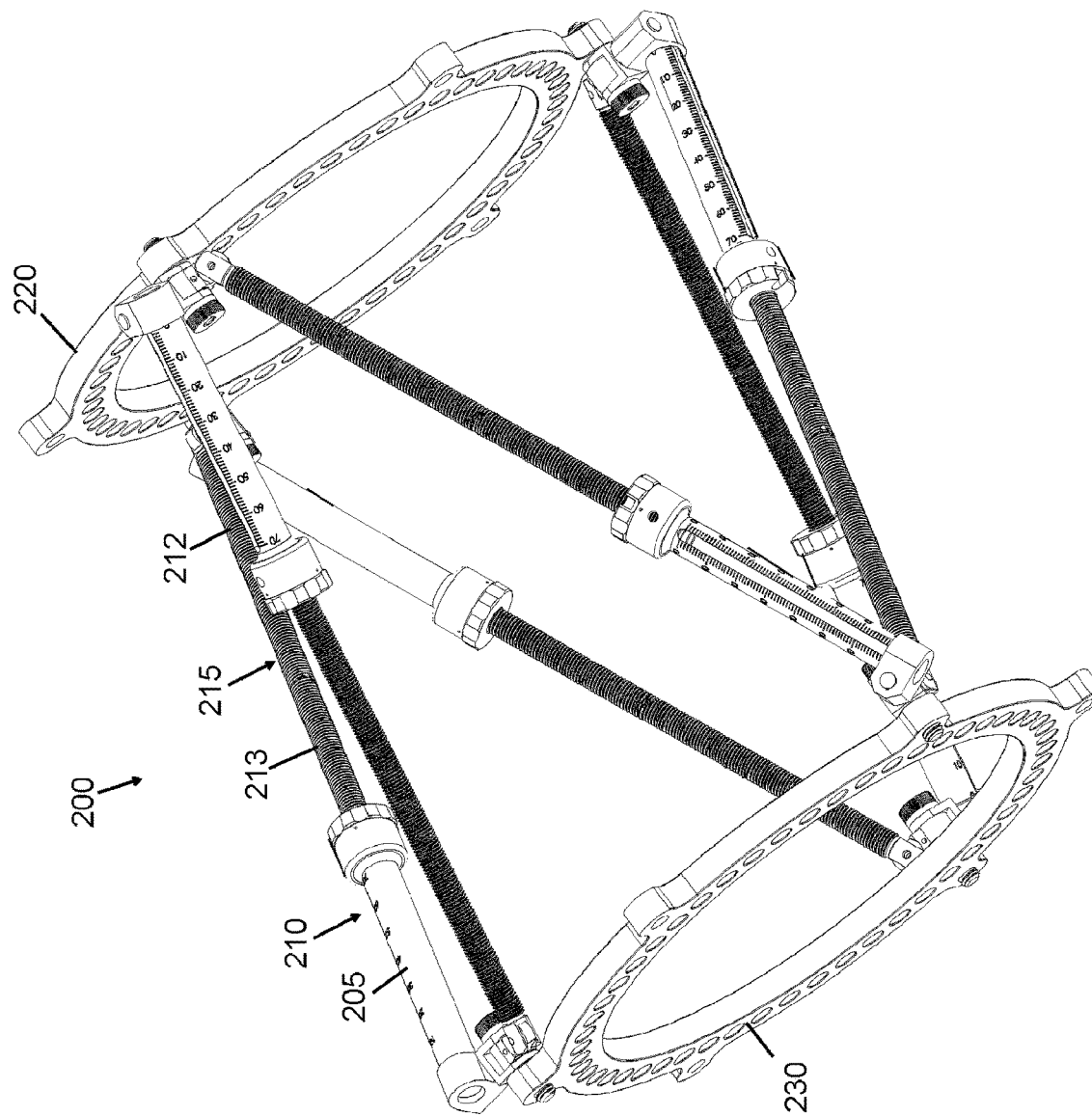
FIG. 39 is a perspective view of the interconnected strut assemblies of FIG. 25 in the extended configuration and connected the platforms of the external bone fixation system.
Figure 41:
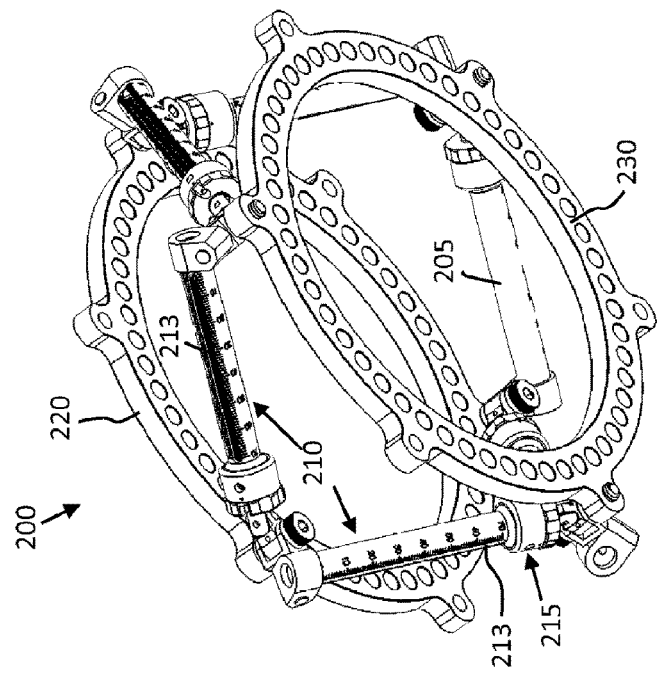
FIG. 41 illustrates bottom perspective and side view of the interconnected strut assemblies of FIG. 25 in the collapsed third configuration with add-on rods installed and connected the platforms of the external bone fixation system.
Figure 41:
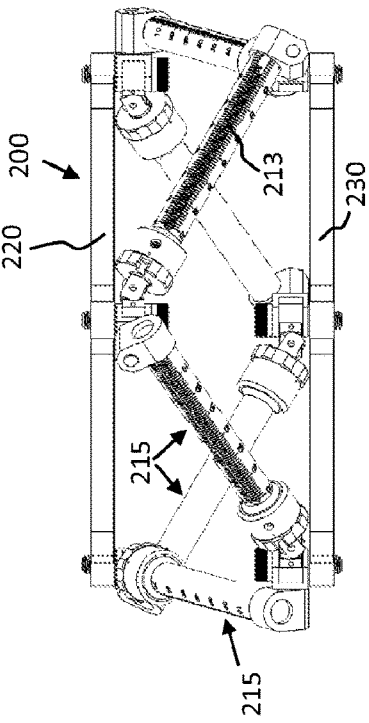
Figure 40:
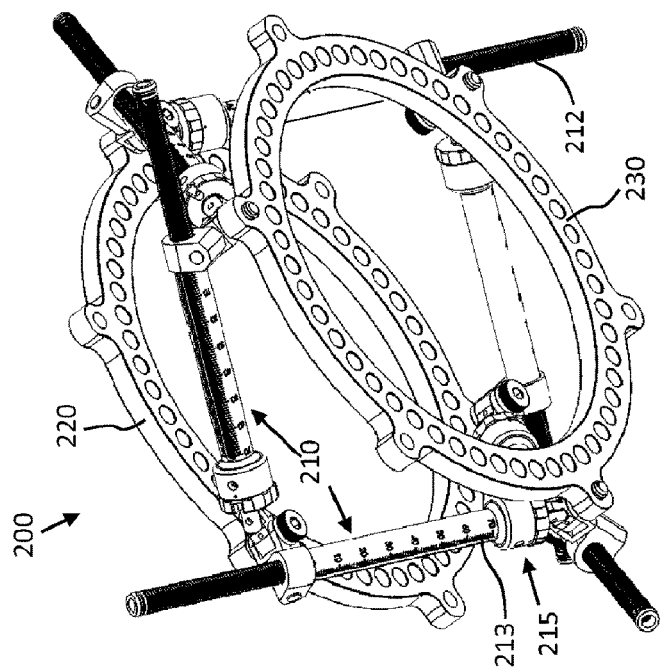
FIG. 40 illustrates bottom perspective and side view of the interconnected strut assemblies of FIG. 25 in the collapsed third configuration and connected the platforms of the external bone fixation system.
Figure 40:
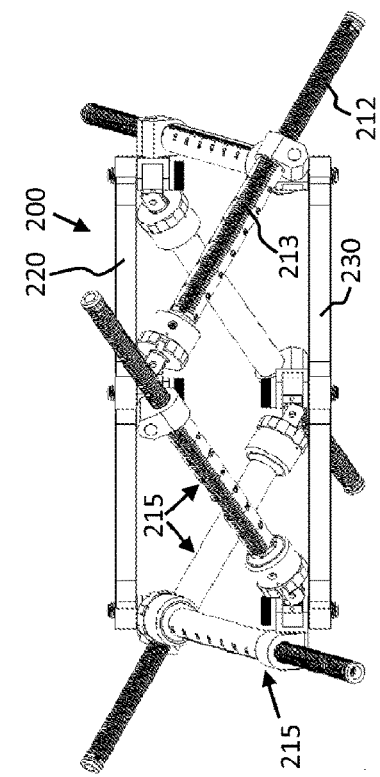
Figure 42:
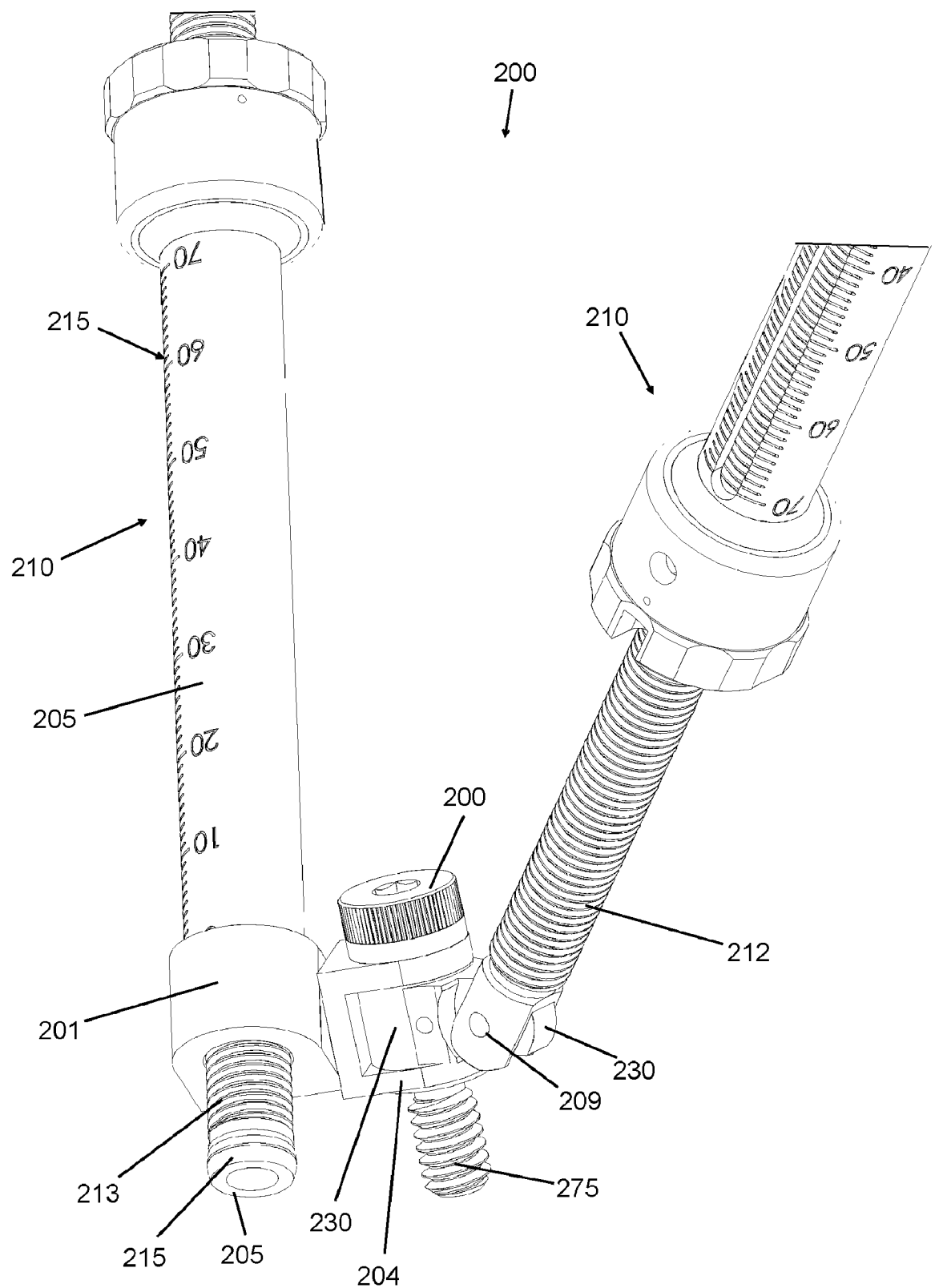
FIG. 42 is a top perspective view of a strut-platform connection mechanism coupling a pair of strut assemblies of the external bone fixation system of FIG. 25.
Figure 43:
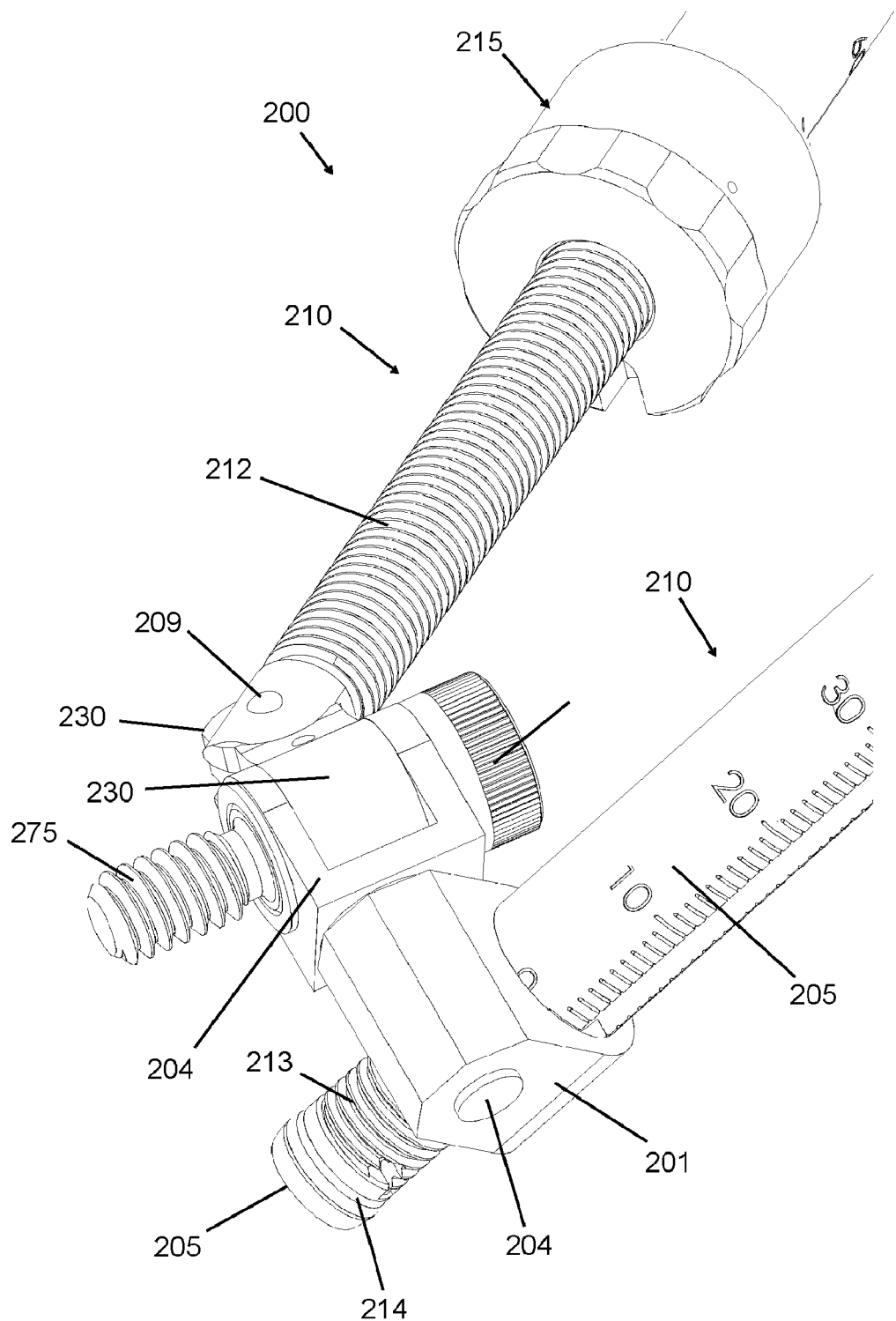
FIG. 43 is a bottom perspective view of the strut-platform connection mechanism of FIG. 42.
Figure 44:
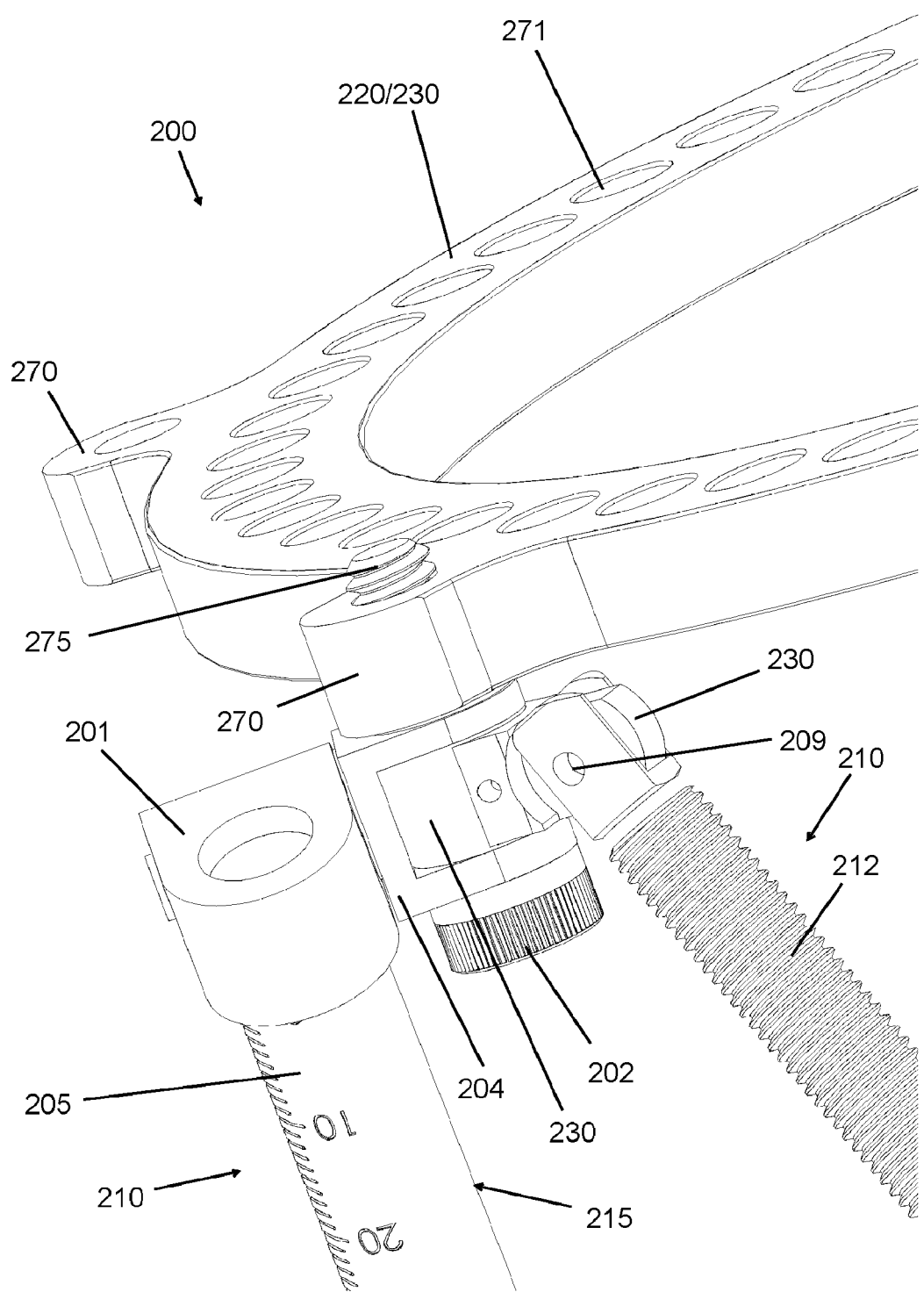
FIG. 44 is a top perspective view of the strut-platform connection mechanism of FIG. 42 coupling the pair of strut assemblies to a platform.
Figure 45:
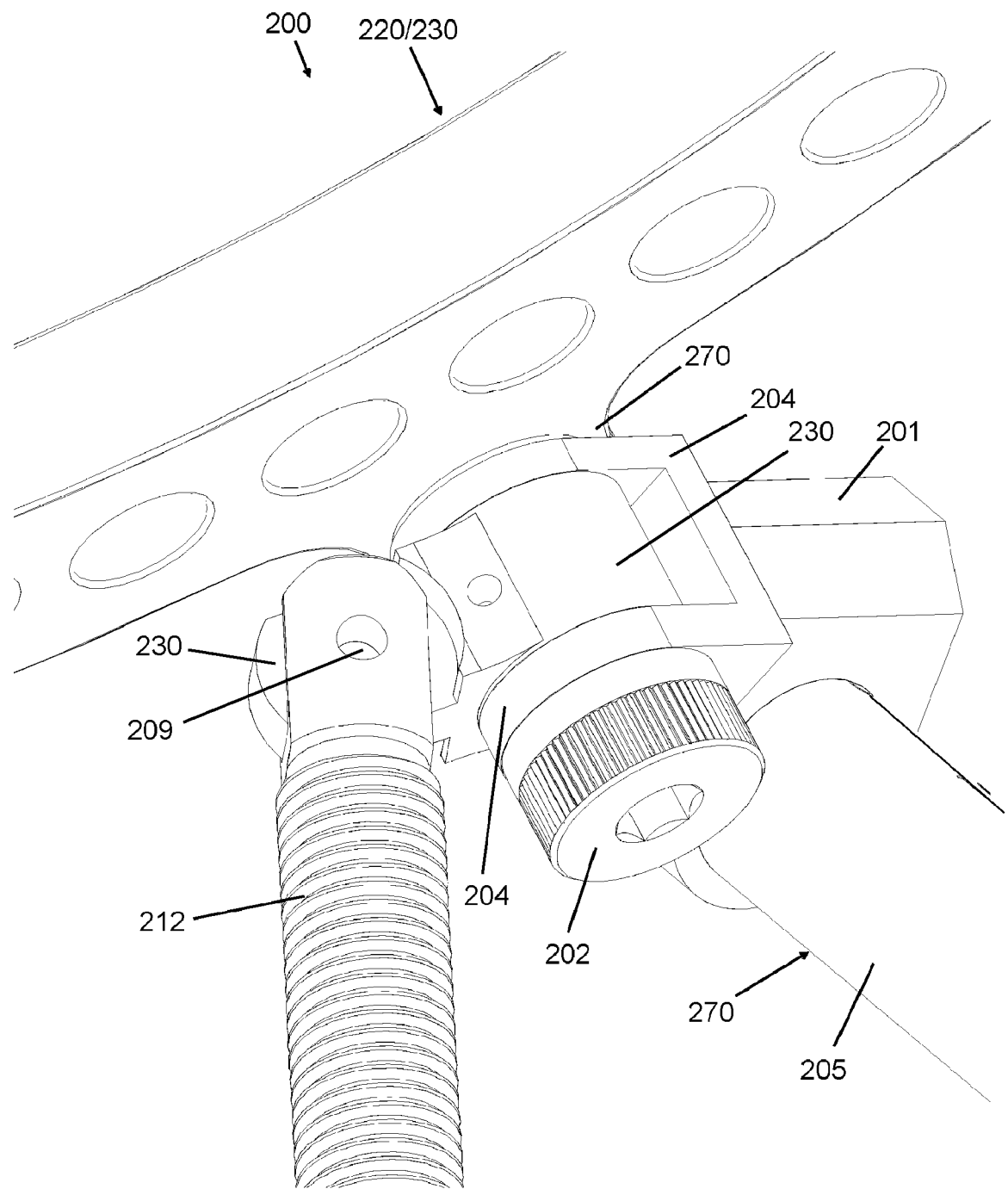
FIG. 45 is a bottom perspective view of the strut-platform connection mechanism of FIG. 42 coupling the pair of strut assemblies to a platform.
Figure 46:
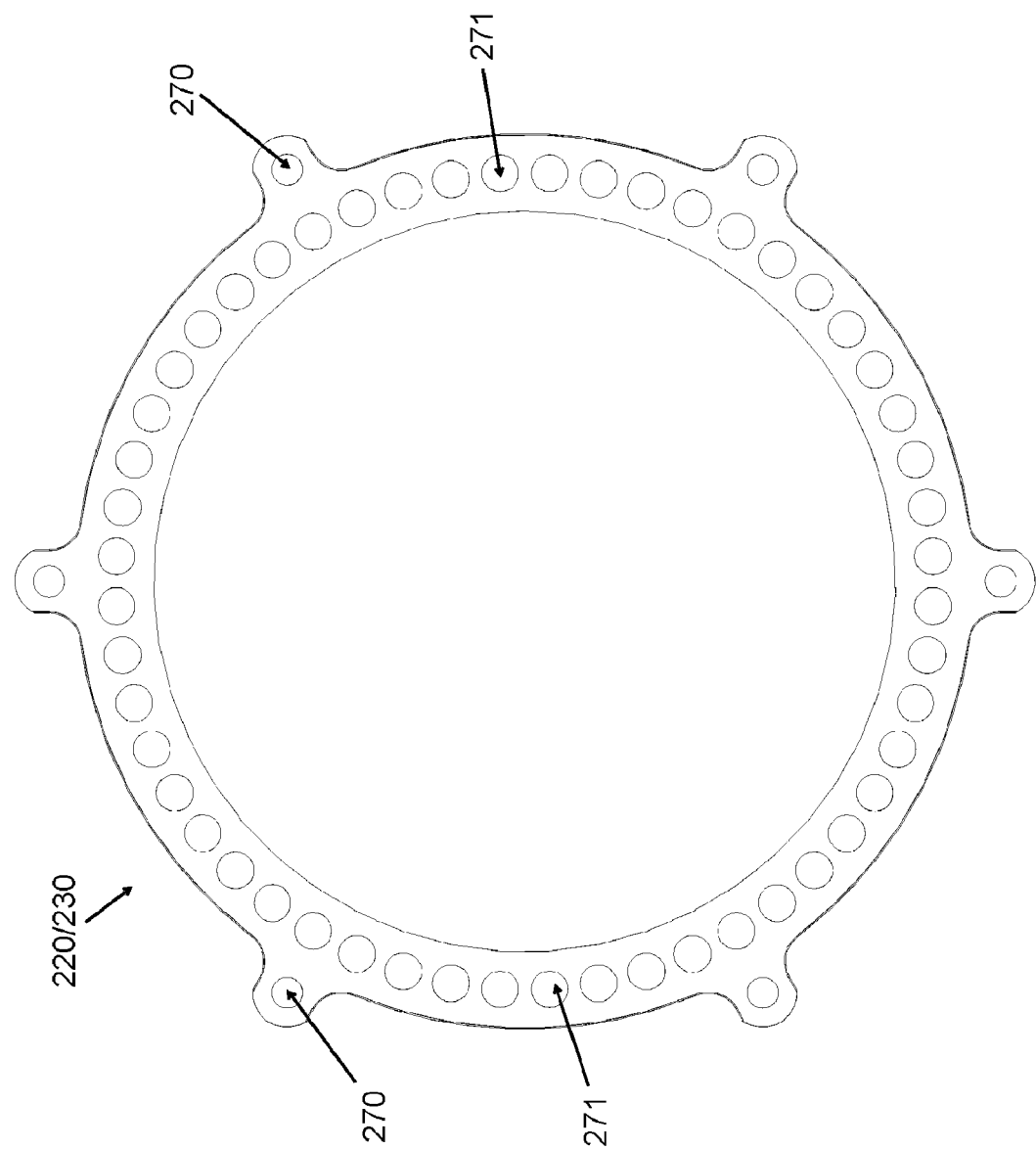
FIG. 46 is a top view of a platform of the external bone fixation system of FIG. 25.

As noted above, the strut bodies 5 of the strut assemblies 110 may include a joint to the first or second platforms 120, 130 that provides for rotation of strut bodies 5. As shown in FIGS. 14-18, the strut bodies 5 may include a spherical projection 15 formed or coupled to an end or end portion thereof. As shown in FIG. 19, the spherical projection 15 may include one or more apertures 26. The joints of the strut bodies 5 of the strut assemblies 110 may include a first barrel knuckle 7 that includes a spherical inner cavity that is configured to accept and mate with the spherical projection 15 of the strut bodies 5, as shown in FIG. 19. The barrel knuckle 7 may include one or more apertures 28 extending therethrough. The joints of the strut bodies 5 may further include at least one pin 24 that is configured to extend through a corresponding aperture 28 of the barrel knuckle 7 and a corresponding aperture 26 of the spherical projection 15. In this way, the at least one pin 24 may limit rotation of the spherical projection 15 of the strut body 5 within the barrel knuckle 7 about one axis X3-X3, as shown in FIG. 19—thereby forming a cardan joint.

As shown in FIGS. 14-18, the barrel knuckle 7 may also be configured to removably and rotationally mate or attach with the first and second platforms 120, 130. As shown in FIGS. 15-18, the first and second platforms 120, 130 may include studs 50 extending therefrom that define free ends. The studs 50 may be arranged in closely-spaced pairs and provided about the circumference of the first and second platforms 120, 130. In some embodiments, the studs 50 may extend radially, such as perpendicular to the axis X2-X2 and/or along a plane defined by the respective platform 120, 130. As shown in FIG. 15, the studs 50 may be substantially cylindrical but include a flat portion 52. The flat portion 52 may be a planar chord joining two portions of the cylindrical outer surface of the studs 50. Each of the studs 50 may also include a recess or groove 52 extending at least substantially circumferentially about the outer surface between the free ends thereof and the respective first or second platform 120, 130. The circumferential groove 52 may thereby form a head portion of the studs 50 with a substantially cylindrical outer surface and the flat portion 52.

As shown in FIGS. 16-18, the barrel knuckle 7 may include an opening or cavity that is shaped and sized to receive a stud 50 of the first or second platform therein. As also shown in FIGS. 16-18, the barrel knuckle 7 may include a dowel pin or other feature 1 that extends across a portion of the opening or cavity of the barrel knuckle 7. The opening or cavity of the barrel knuckle 7 and the dowel pin 1 may form the same shape and configuration as the studs 50, such as the cylindrical outer surface and flat portion 52 of the studs 50 described above.

In this way, a strut 110 may be oriented such that the barrel knuckle 7 and pin 1 can be aligned with and slid over the cylindrical outer surface and flat portion 52 of a stud 50, respectively, as shown in FIGS. 16 and 17. As shown in FIG. 17, the pin 1 may be aligned with the groove 52 of the stud 50, and the then the strut 110 may be rotated such that the pin 1 is no longer aligned with the flat portion 52 and thus trapped within the groove 52 behind the head portion of the stud 50. The rotation of the strut 110 may be such that joint of the threaded rod assemblies 25 is aligned with, or at least positioned closer to, a corresponding stud 50 of the other of the first and second platforms 120, 130. The joint thereby allows for at least some degree of relative rotation between the strut 110 and the respective platform 120, 130. In this way, the joint provides two mutually perpendicular revolute axis of rotation between the strut 110 and the respective platform 120, 130.

In this way, the joints of the strut bodies 5 may be a revolute joint made from features native to the platforms 120, 130 and others native to the strut assembly 110. The joint also does not provide for a full 360 degrees of rotation, but the flat portion 52 of the studs 50 may be oriented such that a range of relative rotation between the stud 50 and the strut 110 is provided, such as the amount or range of relative rotation required or encountered during the normal course of action of the system 100. The joint thereby utilizes an over rotation of the strut assemblies 110 beyond their normal or expected operable range to assemble the joints. Since the strut assemblies 110 must be attached at both ends, one end to the first platform 120 and the other end to the second platform 130, this joint configuration is sufficient for the first connection to one of the first or second platforms 120 since the remainder of the strut assembly 100 is free to swing outside of the operable range during the attachment process.

As shown in FIG. 19, as the studs 50 are substantially identical to each other, the joint of the threaded rod assemblies 25 may mimic the "out of operable rotational range" feature of the joint of the strut body 5 (or be an operationally equivalent joint). The end portion of the pre-installed threaded rod 12 of the threaded rod assemblies 25 may include or form a strut screw 12 with a spherical knuckle 11 fixed thereon. The end portion of the strut screw 12 may be threaded, and a detent ring 16 and wave spring 23 may be trapped between an end cap 17 threaded on to the external threads and the spherical knuckle 11. The end cap 17 and the detent ring 16 may be rotationally coupled or fixed one another. The spherical knuckle 11 may include a series of detents adjacent the detent ring 16, and the wave spring 23 may force the detent ring 16 detents. The spherical knuckle 11 may also include at least one aperture for the acceptance of at least one pin 24 therethrough. The at least one pin 24 may rotationally fix the spherical knuckle 11 with a cavity of a screw knuckle 15, as shown in FIG. 19. As explained further below, the screw knuckle 15 may be coupled to a stud 50 of one of the first and second platforms 120, 130. As such, rotation of the threaded rod assembly 25 (e.g., via the cross pin 18) may thereby rotate the detent ring 16 with respect to the screw knuckle 15 to provide a visual and/or tactical indication of the rotational movement and/or position of the threaded rod assemblies 25.

The screw knuckle 15 of the joints of the threaded rod assemblies 25 of the strut assemblies 110 may include a spherical inner cavity that is configured to accept and mate with the spherical knuckle 11 of the threaded rod assemblies 25, as shown in FIG. 19. As noted above, the at least one pin 24 may extend into the screw knuckle 15 and the screw knuckle 15, which may limit rotation of the spherical knuckle 11 of the threaded rod assemblies 25 within the screw knuckle 15 about one axis X4-X4, as shown in FIG. 19—thereby forming a cardan joint.

As also shown in FIG. 19, the screw knuckle 15 of the joints of the threaded rod assemblies 25 of the strut assemblies 110 may include an opening or cavity that is shaped and sized to receive a stud 50 of the first or second platform 120, 130 therein. As also shown in FIG. 19, the screw knuckle 15 may include a pin or other feature 19. The pin 19 may be provided within a groove or slot that allows the pin 19 to move between a position such that the pin 19 extends across a portion of the opening or cavity of the screw knuckle 15 and a position such that the pin 19 does not extend across a portion of the opening or cavity of the screw knuckle 15.

The joints of the threaded rod assemblies 25 of the strut assemblies 110 further includes a knob 20, push pin 21 and a ball 4, as shown in FIG. 19. The knob 20 may include an inner surface that forms a cam effective to translate the push pin 21 into and through the screw knuckle 15 and into the pin 19. In this way, a strut 110 that is connected to one of the first and second platforms 120, 130 via the joint of the strut body 5 may be oriented such that the screw knuckle 15 of the joint of the threaded rod assembly 25 is aligned with and slid over the cylindrical outer surface and flat portion 52 of a stud 50. The pin 19 may be aligned with the groove 52 of the stud 50, and then the knob 20 may rotated such that the cam of the knob 20 pushes the push pin 21 into the pin 19 such that the pin 19 extends across a portion of the opening or cavity of the screw knuckle 15 and within the groove 52 behind the head portion of the stud 50. The ball 4 may be positioned adjacent the push pin 21 and prevent further rotation of the knob 20 from such a "locked" position. In this way, the joints of the threaded rod assemblies 25 may be revolute joints made from features native to the platforms 120, 130 and others native to the strut assembly 110.

FIGS. 20-59 is illustrate another 6 DOF bone or tissue fixation systems and related fixation methods 200 include the desirable stability and mobility characteristics of a hexapod system without time consuming strut-length choices and assembly difficulties. The 6 DOF bone or tissue fixation systems and related fixation methods 200 of FIGS. 20-59 are similar to the 6 DOF bone or tissue fixation systems and related fixation methods 100 of FIGS. 1-19, and therefore like reference numerals preceded with "2" are used to indicate like aspects or functions, and the description above directed to aspects or functions thereof (and the alternative embodiments thereof) equally applies to the systems and methods 200. As shown in FIGS. 20-44B, the system 200 differs from the system 100 in that the individual strut assemblies 210 (six strut assemblies 210) are coupled to each other as a single unit 315 both prior to (see FIGS. 20-31) and after attaching to the first and second platforms 220, 230 (see FIGS. 32-44B). As explained further below, the ends of the strut assemblies 210 include movable joints or couplings that allow some relative movement between the pairs of strut assemblies 210, but prevent the strut assemblies 210 from becoming disconnected from each other. In this way, the six strut assemblies 210 form a single construct, unit or structure 215 "out of the box," as shown in FIGS. 20-31. The singular construct 215 of the six, individual but movably coupled strut assemblies 210, as shown in FIGS. 20-31, allows for quick and easy manipulation and attachment to the first and second platforms 220, 230 as shown in FIGS. 32-44B. For example, rather than obtaining, assembling and/or adjusting the six strut assemblies 201 individually, and then attaching them individually to each other and then to the first and second platforms 220, 230, the singular construct 215 of the six movably coupled strut assemblies 210 can be obtained and adjusted as a single unit as shown in FIGS. 20-31, and quickly and easily coupled to the first and second platforms 220, 230 as shown in FIGS. 32-44B.

As shown in FIGS. 45-48, 50, 58 and 59, the singular construct 215 of the six strut assemblies 210 may be formed by movable joints or coupling mechanisms that couple opposing ends of adjacent strut assemblies 210. Such movable joints may be any joint that allows for movement with respect to the first or second platforms 220, 230 to which it is attached and relative movement of the joined adjacent strut assemblies 210 to allow or provide for the movement and/or angulation between the first or second platforms 220, 230 as shown in FIGS. 41-44B. The exemplary movable joint shown in FIGS. 45-48, 50, 58 and 59 includes a base knuckle 201 rigidly affixed to a strut barrel 205 via a post of a knuckle pivot 204. The post of the knuckle pivot 204 may seat within a corresponding aperture in the base knuckle 201 and extend into an indentation in the strut barrel 205. In this way, the knuckle pivot 204 may be rotationally coupled to the base knuckle 201 about an axis that extends perpendicular to the strut barrel 205. As also shown in FIGS. 45-48, 50, 58 and 59, the first or primary strut screw 212 is pivotably coupled to a pivot yoke 230A via a spring pin 213. The first strut screw 212, pivot yoke 230A and spring pin 213 are configured such that the first strut screw 212 and pivot yoke 230A are pivotably coupled about an axis (the spring pin 213) that extends perpendicular to the screw 212.

As shown in FIGS. 45-48, 50, 58 and 59, the pivot yoke 230A and the knuckle pivot 204 may rotatably couple to each other via a shoulder screw 202 that extends through apertures in shoulders of the knuckle pivot 204 that are substantially aligned and spaced along the long axis of the strut barrel 205. The pivot yoke 230A may be positioned between the shoulders of the knuckle pivot 204 such that it is trapped therebetween along the long axis of the strut barrel 205, and the shoulder screw 202 may also pass through an aperture in the pivot yoke 230A. In this way, the shoulder screw 202 may extend through one of the shoulders of the knuckle pivot 204, then the pivot yoke 230A, and then ultimately through the other shoulder of the knuckle pivot 204. The knuckle pivot 204 and the pivot yoke 230A may thereby be rotatably coupled to each other about an axis defined by the shoulder screw 202. The shoulder screw 202 may be prevented from sliding out of the apertures of the shoulders of the knuckle pivot 204 and the aperture of the pivot yoke 230A by a pin (not shown) that extends through the pivot yoke 230A and across at least a portion of the shoulder screw 202 within a groove or the like of the shoulder screw 202.

Figure 47:
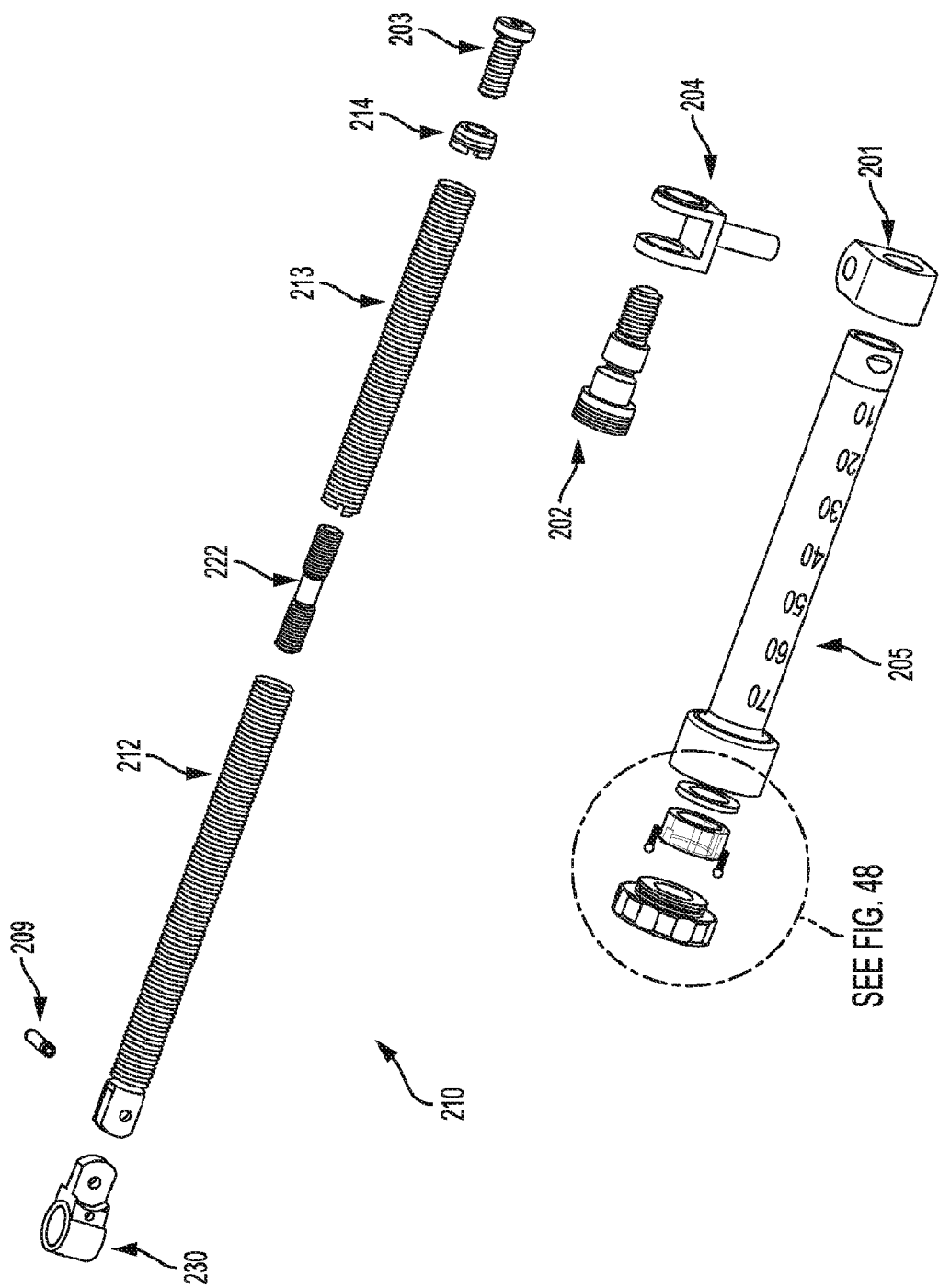
FIG. 47 is an exploded perspective view of an exemplary strut assembly of the external bone fixation system of FIG. 25.
Figure 48:
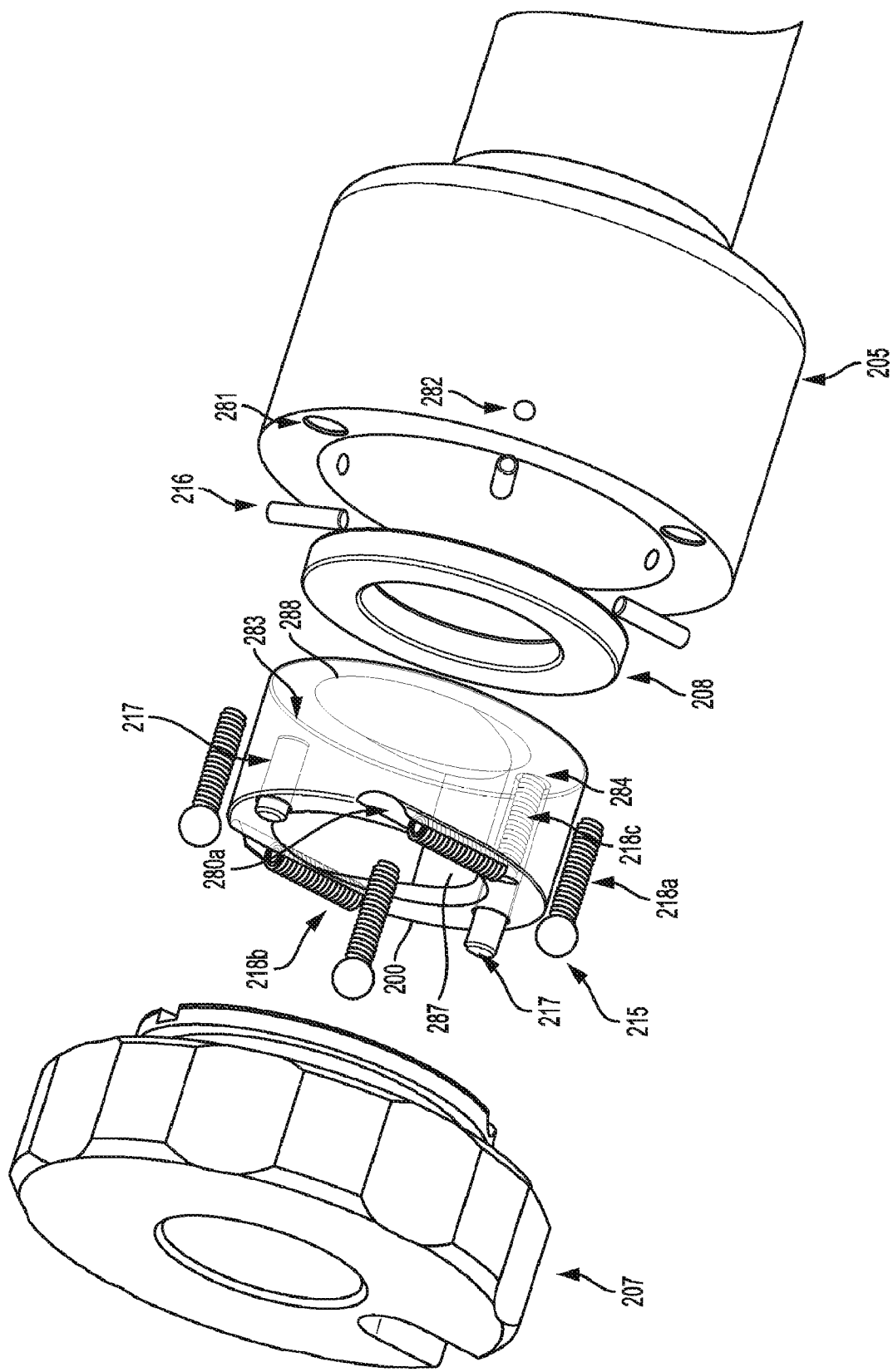
FIG. 48 is an exploded perspective view of an exemplary length adjustment mechanism of a strut assembly of the external bone fixation system of FIG. 25.
Figure 49:
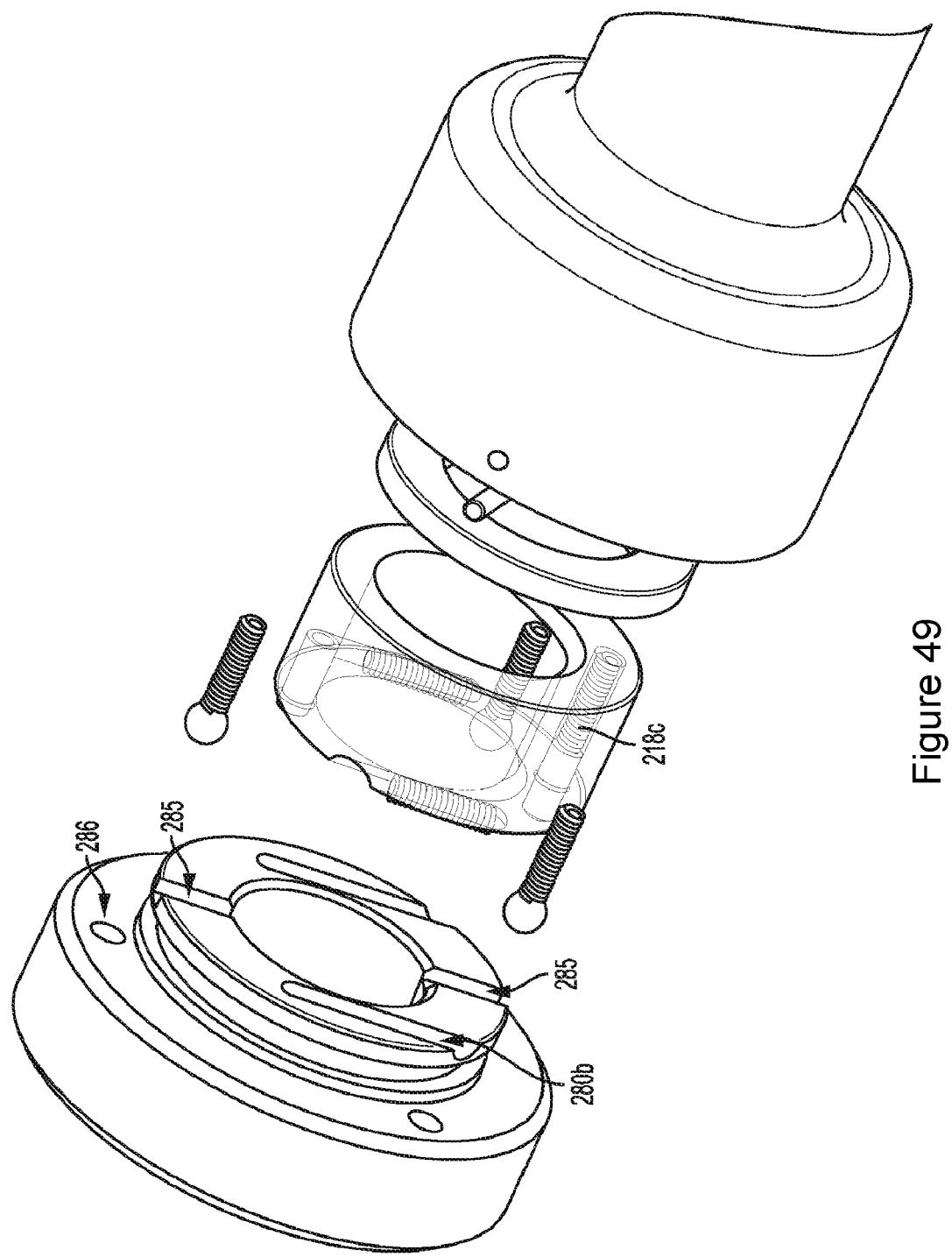
FIG. 49 is an exploded perspective view of an exemplary length adjustment mechanism of a strut assembly of the external bone fixation system of FIG. 25.
Figure 50:
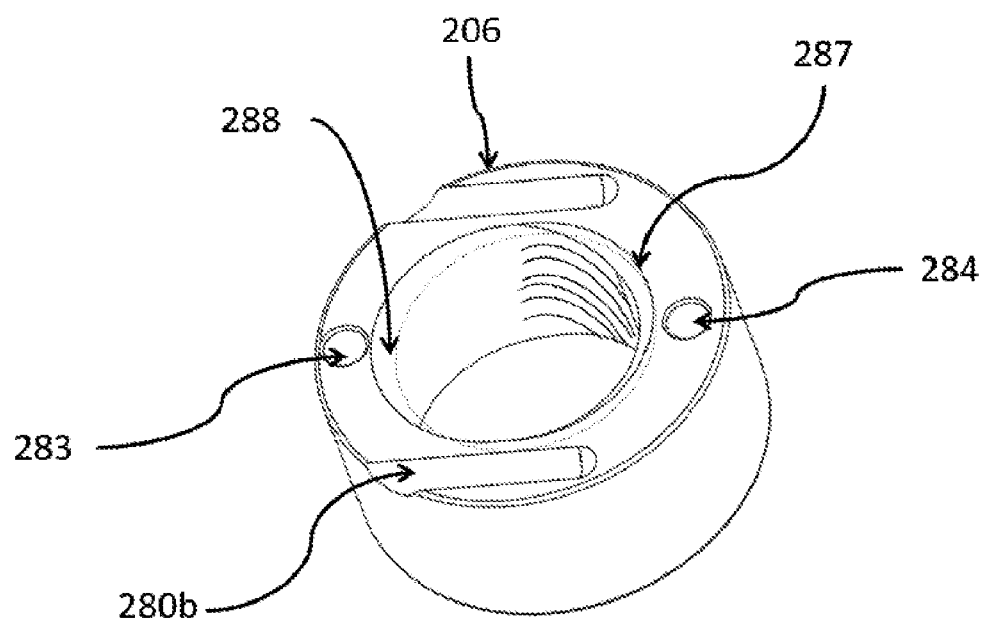
FIG. 50 is a perspective view of an exemplary partially-threaded nut of the length adjustment mechanism of FIG. 48.

As shown in FIGS. 45-49, for example, the movably joined or coupled ends of the pairs or adjacent strut assemblies 210 (as explained above) may be quickly and easily affixed or coupled to the first and second platforms 220, 230. In this way, the singular construct 215 of the six strut assemblies may be quickly and easily affixed or coupled to the first and second platforms 220, 230. With reference to FIGS. 45-49, for example, the shoulder screw 202 may include a threaded portion 275 that extends past the far shoulder of the knuckle pivot 204. In this way, in an unattached state, the threaded portion 275 of the shoulder screw 202 may form free ends. The threaded portion 275 of the shoulder screws 202 may thereby be aligned with a mating aperture or fixation point 270 in the first or second platforms 220, 230 and screwed therein to couple the movable joint between the pairs of strut assemblies 210 to the first or second platforms 220, 230, as shown in FIGS. 47 and 48, for example.

As shown in FIGS. 51-59, for example, the length adjustment mechanism of the strut assemblies 210 differs from the length adjustment mechanism of the strut assemblies 110. With reference to FIGS. 51-59, a washer 208 may be seated within the base of the cavity or housing of the strut barrel 205. As shown in FIGS. 51, 53, 56, 58 and 59, a nut 206 may also be positioned within the cavity or housing of the strut barrel 205 and over the washer 208. The nut 206 may be sized smaller than the cavity of the strut barrel 205 such that the nut 206 is able to move radially with respect to the long axis of the strut assembly 210 or strut barrel 205 (e.g., concentric or eccentric with the cavity and/or long axis). As shown in FIGS. 51, 53 and 56A-57B, the nut 206 may include an eccentric bore 288 and a concentric internal threaded portion 287 (or vice versa).

With reference to FIGS. 51, 53, 58 and 59, for example, the nut 206 may include radially or laterally extending grooves 280b formed in a top or upper surface thereof. The nut 206 may also include a first dowel hole or aperture 283 extending partially through the nut 206 along the long axis of the strut assembly 210 or strut barrel 205. The nut 206 may further include a second dowel hole or aperture 284 that extends at least partially through the nut 206 along the long axis of the strut assembly 210 or strut barrel 205. A spring 218c and a dowel or pin 217 may be positioned within the second dowel aperture 284 such that the dowel 217 is biased out of the second dowel aperture 284 and above a top surface of the nut 206. However, the spring 218c may include sufficient travel that the dowel 217 can be forced further into the second dowel aperture 284 as compared to its natural or neutral position.

With further reference to FIGS. 51, 53, 58 and 59, for example, an adjustment knob 207 may be positioned partially within the cavity or housing of the strut barrel 205 over the nut 206. The adjustment knob 207 may be rotatably coupled to the strut barrel 205 via a plurality of pins 216 that extend radially through the strut barrel 205 and into a concentric groove within the portion of the adjustment knob 207 positioned within the strut barrel 205. In such a manner, for example, the adjustment knob 207 may be manually rotatable about the long axis of the strut assembly 210 or strut barrel 205. To control and/or provide an indication of the relative angular position orientation of the adjustment knob 207 with respect to the strut barrel 205, a plurality of balls 215 may be biased by springs 218a extending in corresponding apertures 281 within the strut barrel 205. The balls 215 may be biased by the springs 218a into corresponding apertures or indentations 286 formed in a bottom surface of the adjustment knob 207 (see FIG. 52).

Figure 52:
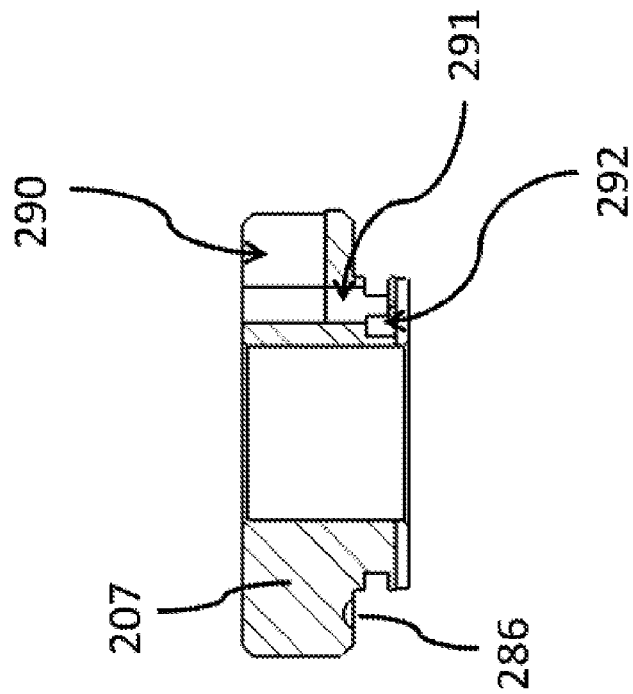
FIG. 52 is a cross-sectional view of the partially-threaded nut of FIG. 50.
Figure 51:
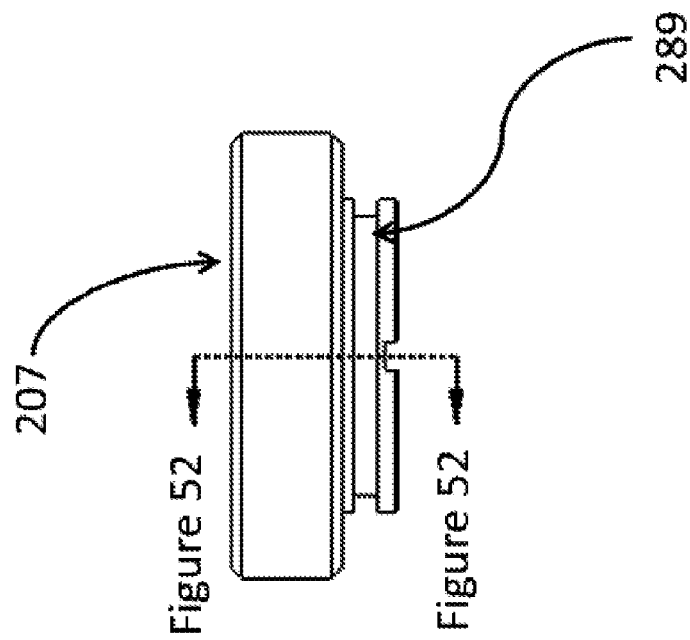
FIG. 51 is a side view of the partially-threaded nut of FIG. 50.
Figure 53:
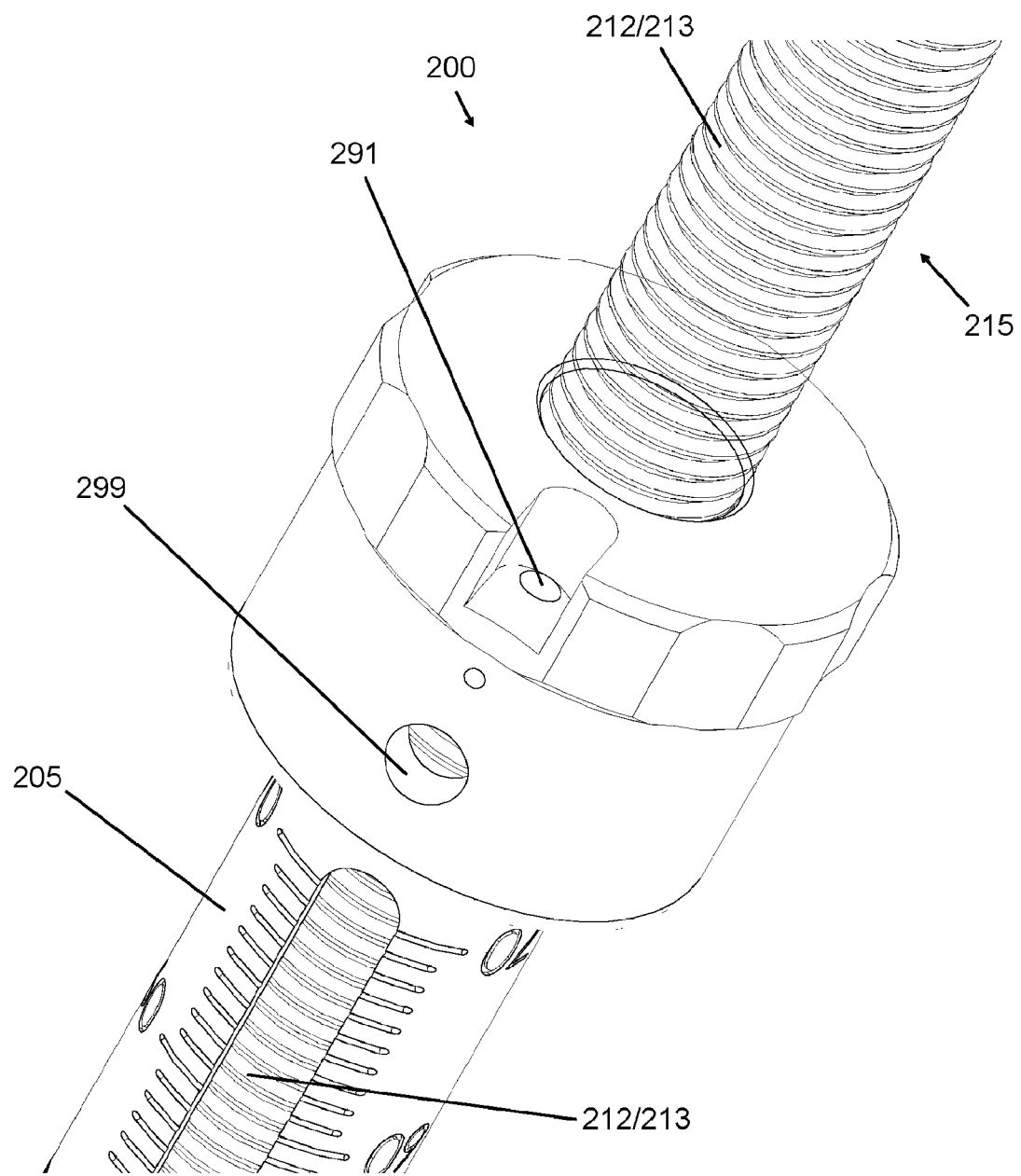
FIG. 53 is a perspective view of the exemplary length adjustment mechanism of FIG. 48.
Figure 55:
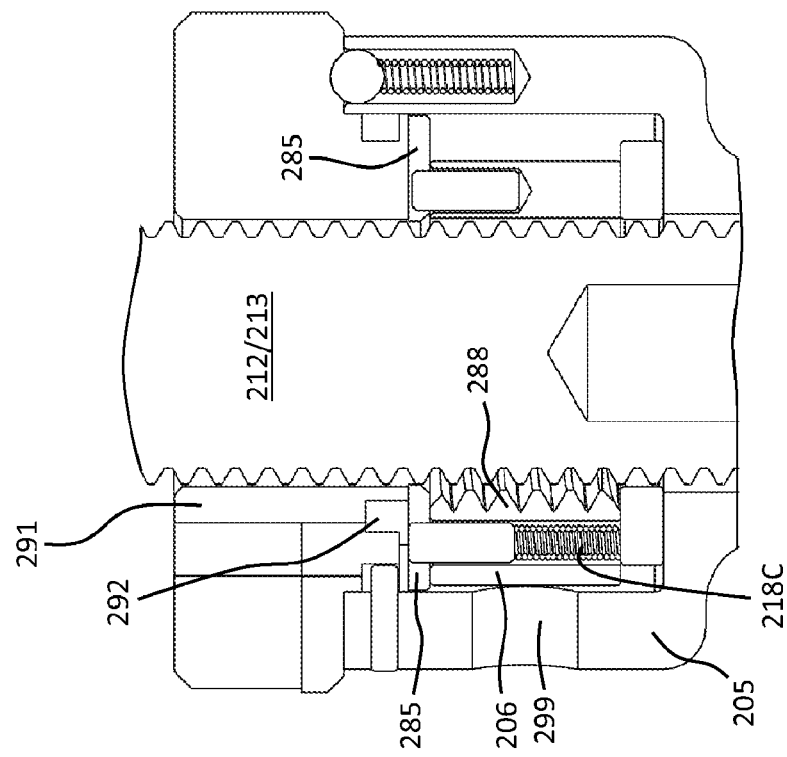
FIG. 55 is a cross-sectional side view of the exemplary length adjustment mechanism of FIG. 48 in a deactivated state.
Figure 54:
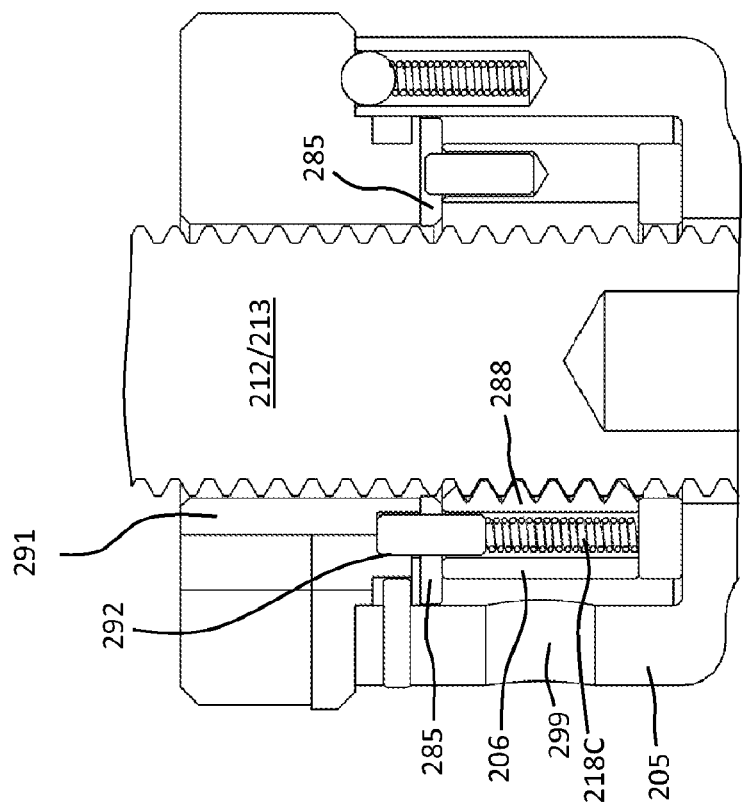
FIG. 54 is a cross-sectional side view of the exemplary length adjustment mechanism of FIG. 48 in an activated state.
Figure 59:
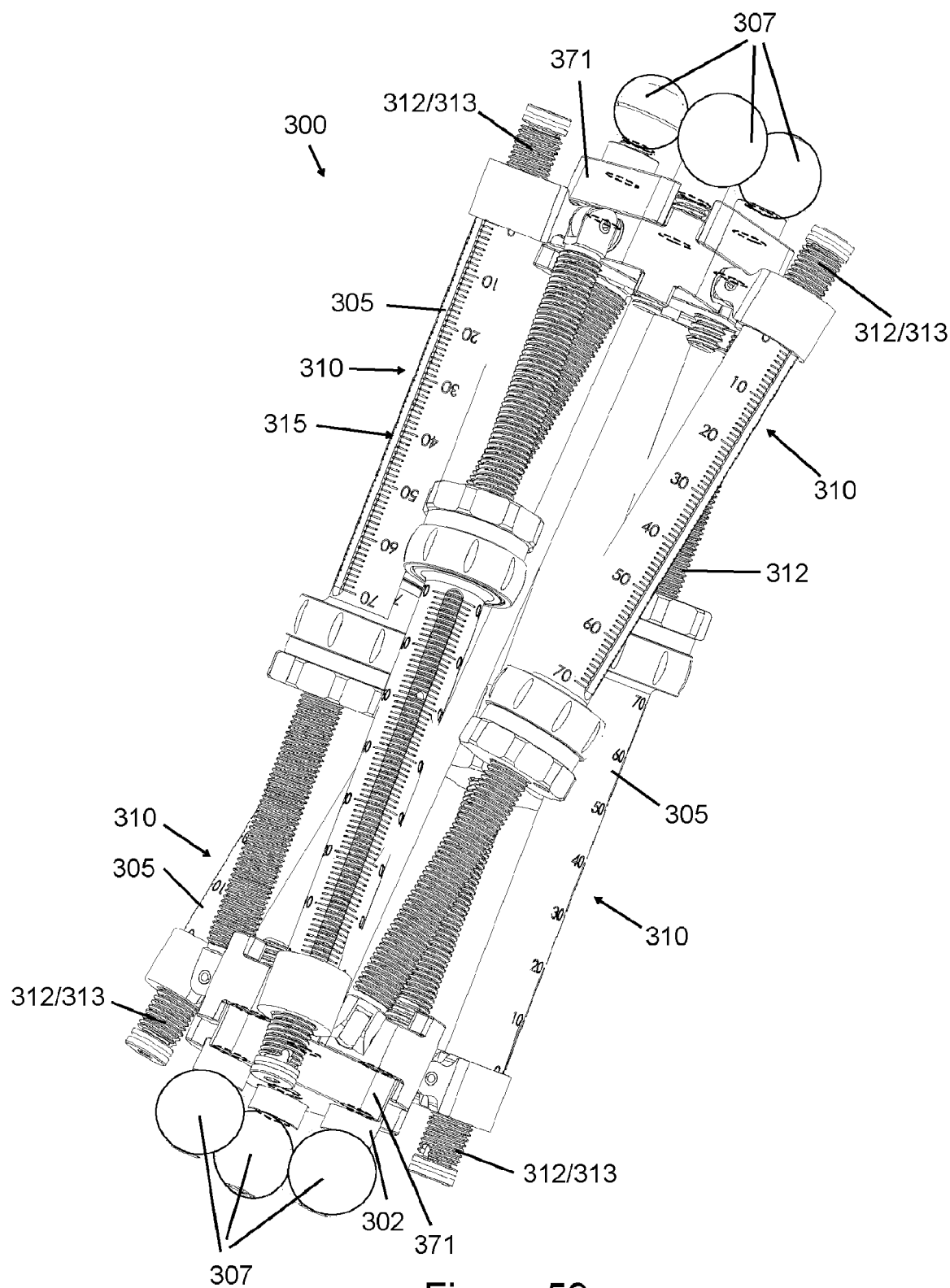
FIG. 59 is a perspective view of exemplary interconnected strut assemblies of another exemplary external bone fixation system according to the present disclosure.
Figure 60:
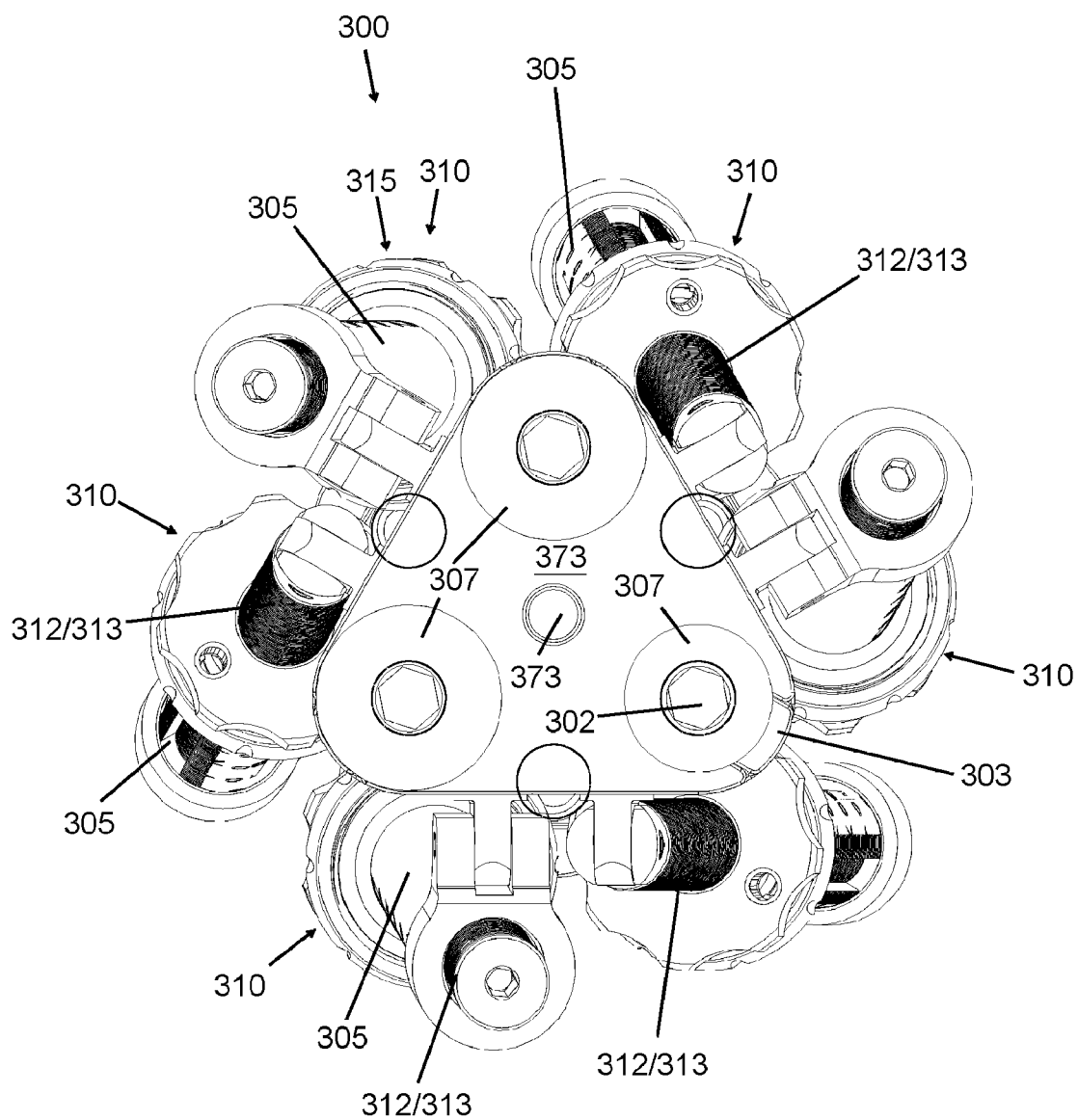
FIG. 60 is a top view of the interconnected strut assemblies of FIG. 59.
Figure 61:
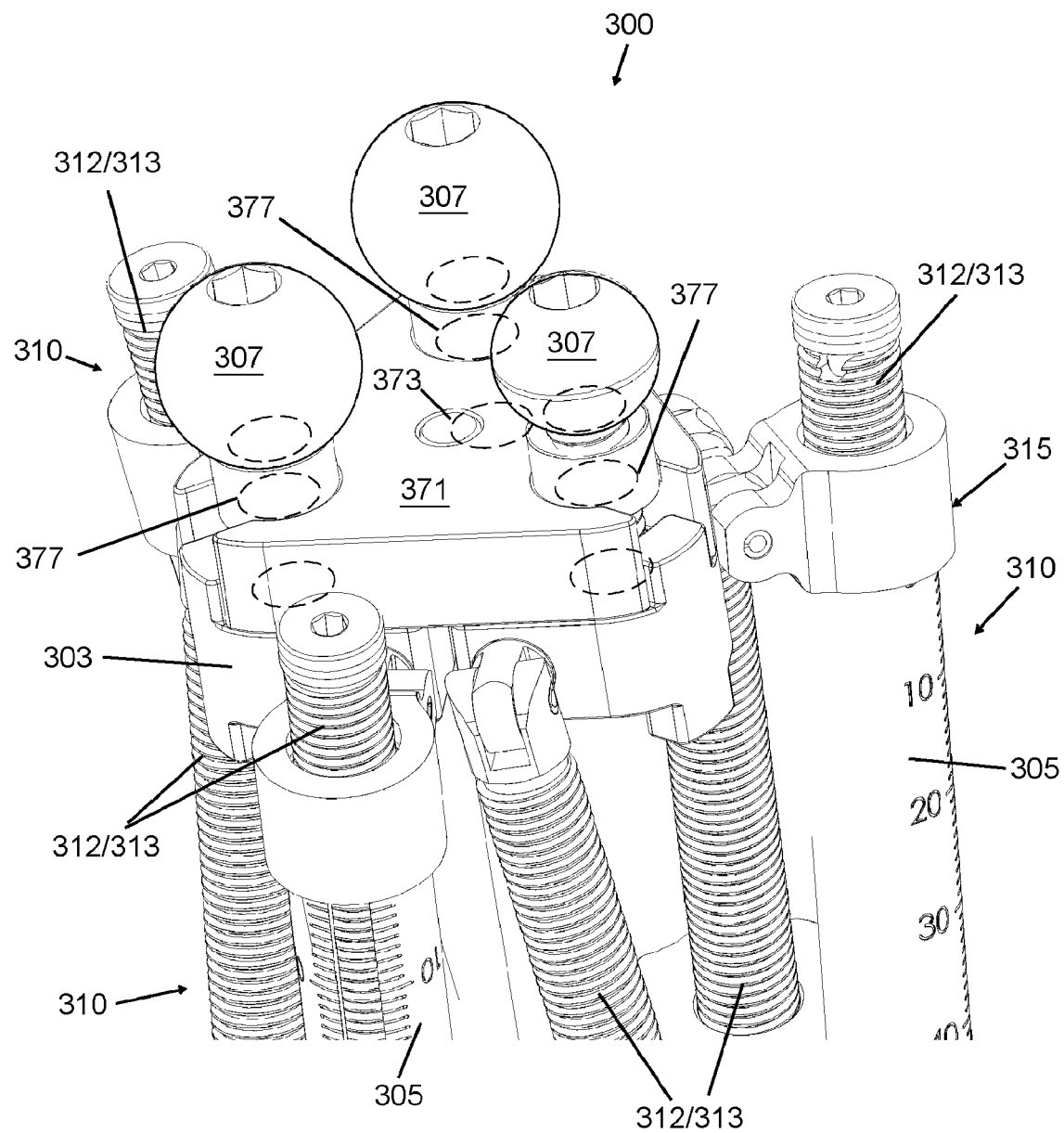
FIG. 61 is an elevational perspective view of the interconnected strut assemblies of FIG. 59.
Figure 62:
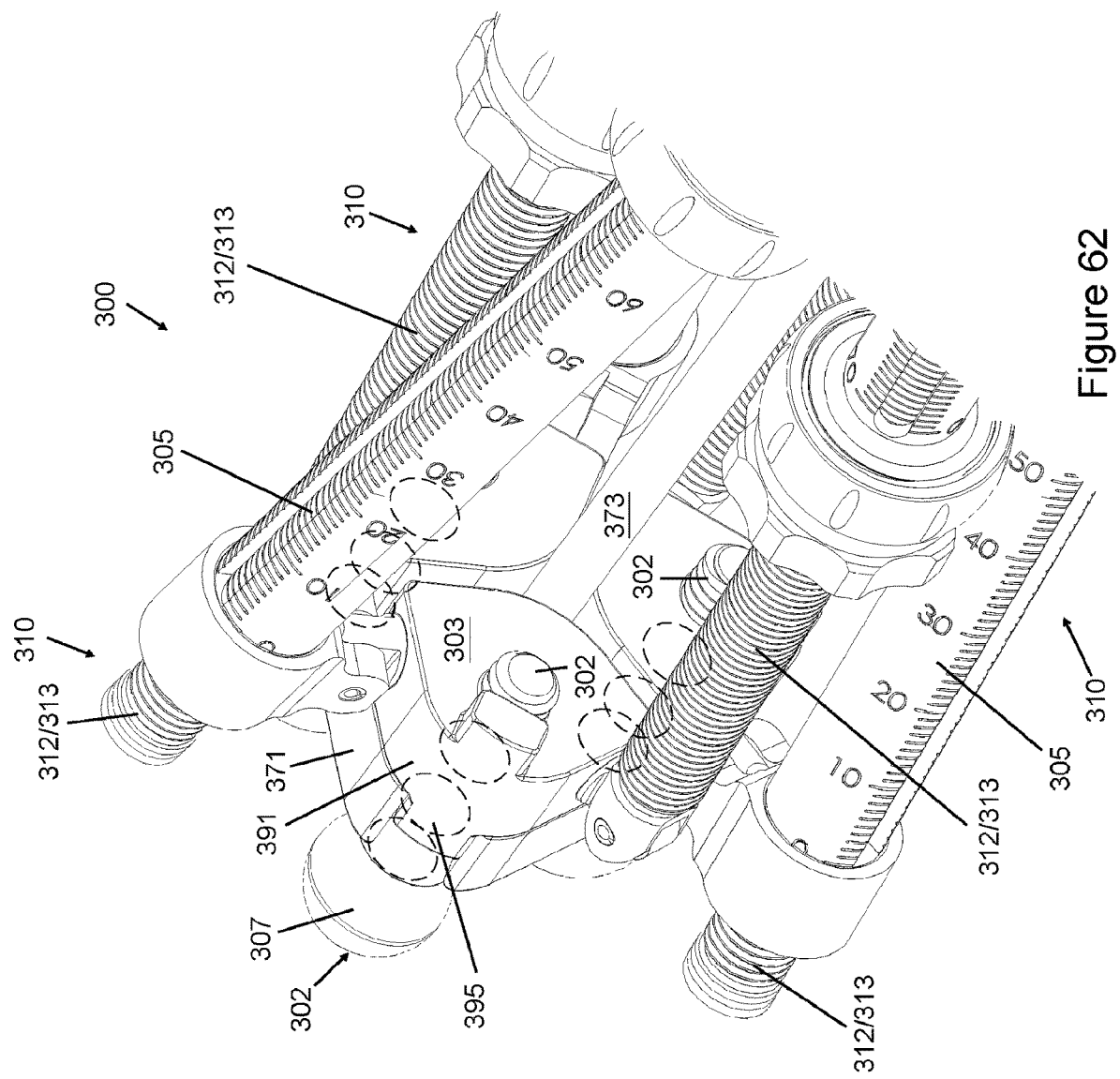
FIG. 62 is a bottom perspective view of the interconnected strut assemblies of FIG. 59.
Figure 63:
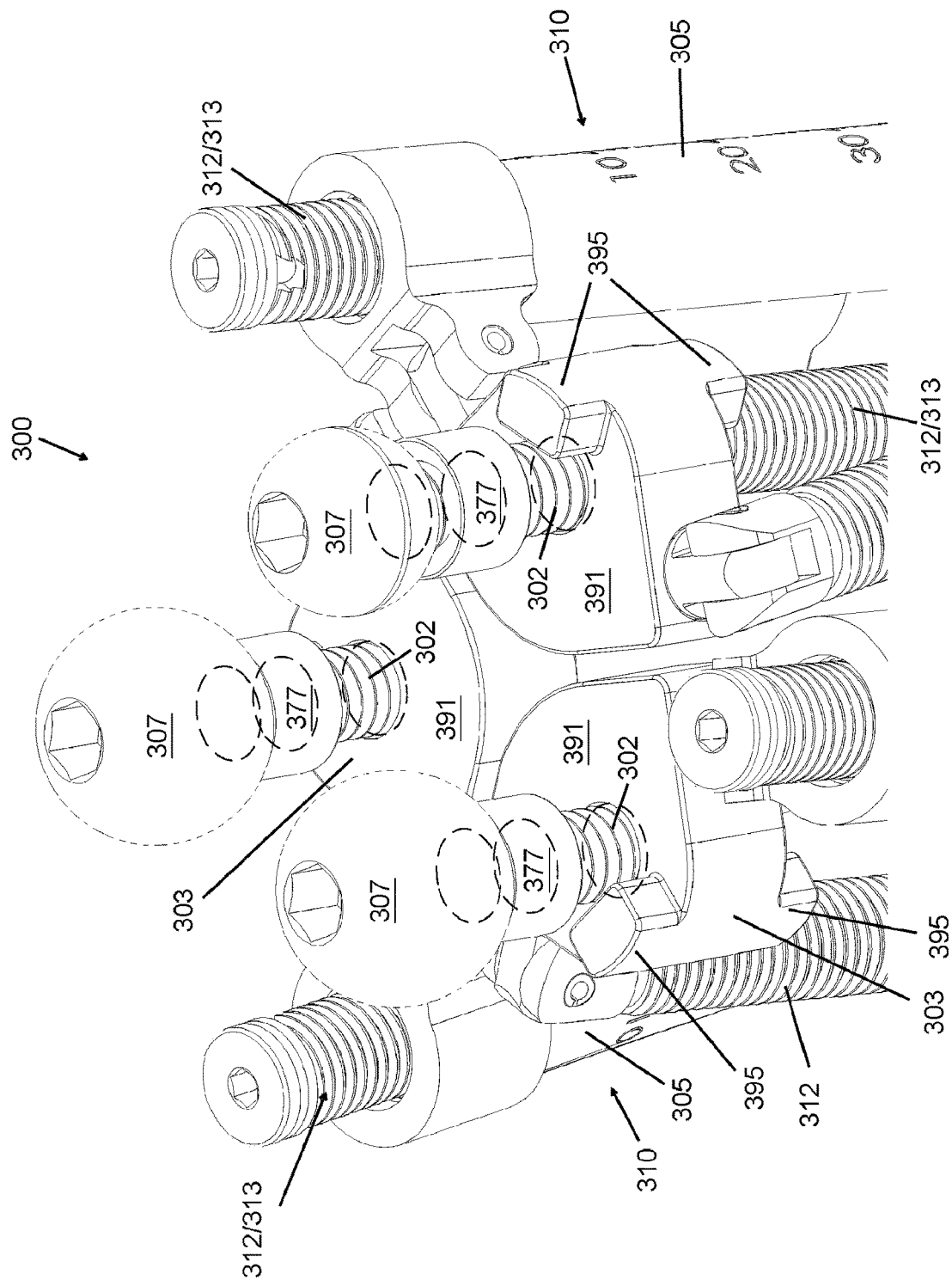
FIG. 63 is an elevational perspective view of the interconnected strut assemblies of FIG. 59.
Figure 64:
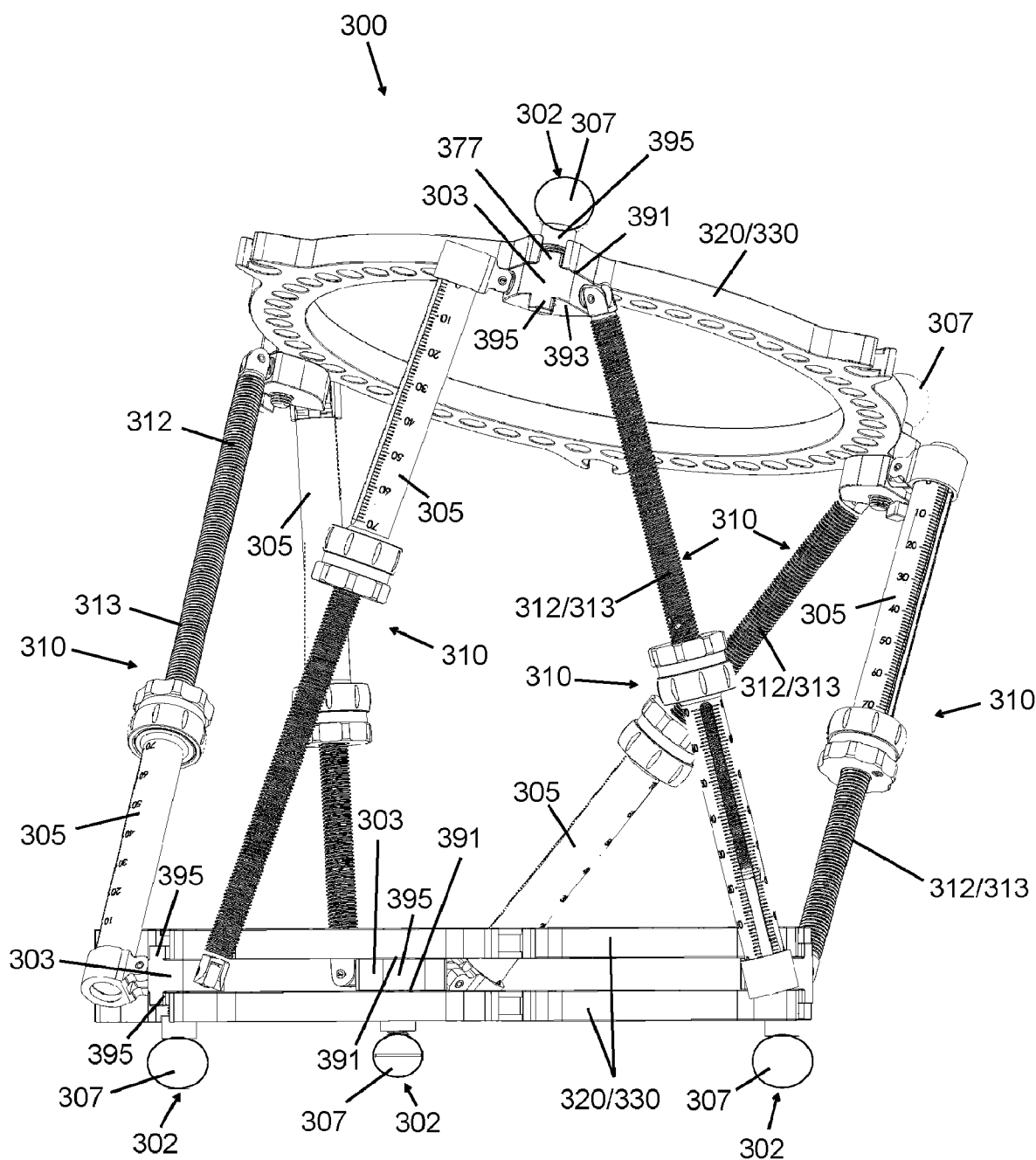
FIG. 64 is a side view of the external bone fixation system of FIG. 59 with the interconnected strut assemblies coupled to a plurality of platforms.
Figure 65:
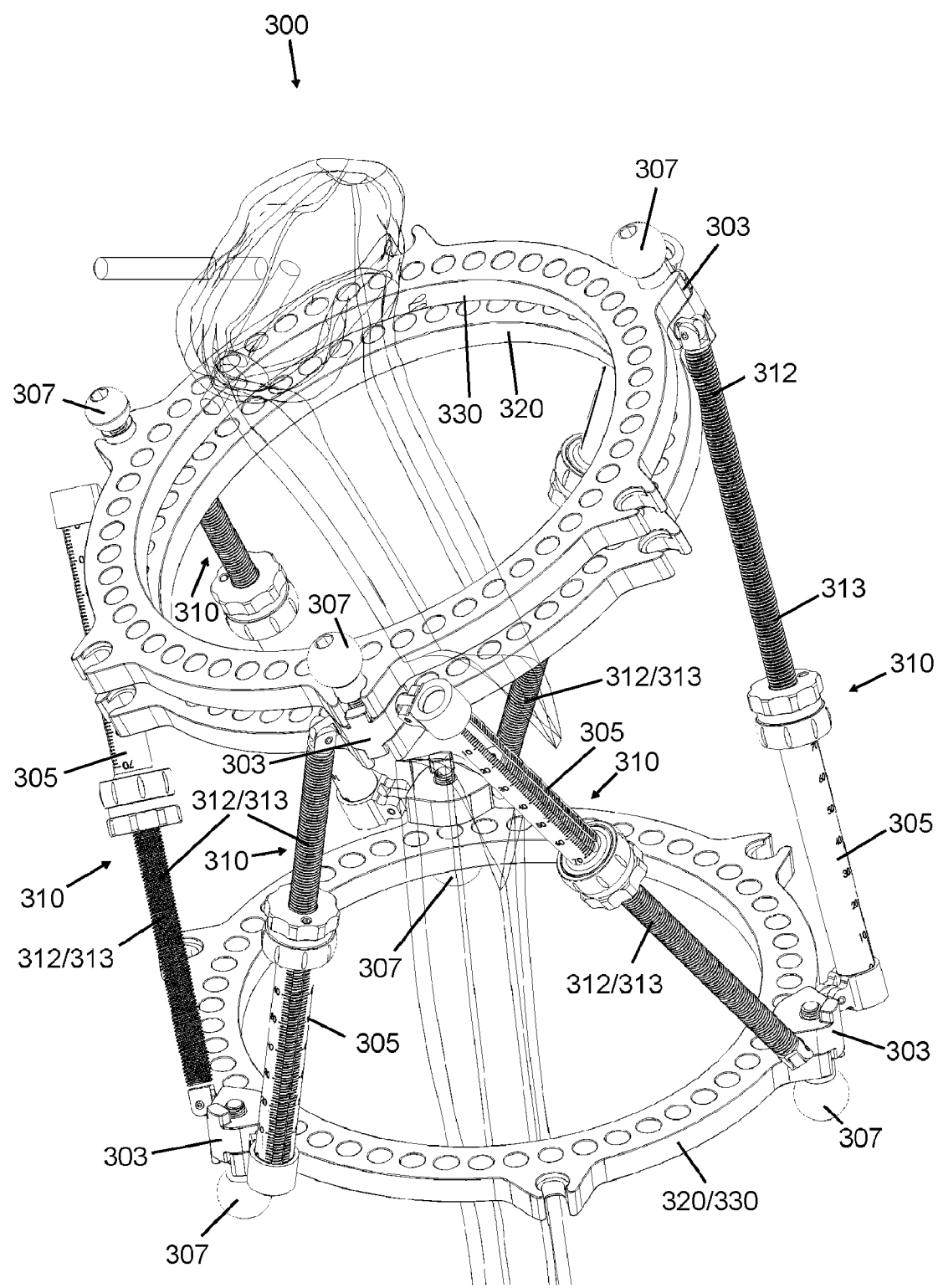
FIG. 65 is an elevational perspective view of the external bone fixation system of FIG. 59 with bone segments illustrated.
Figure 66:
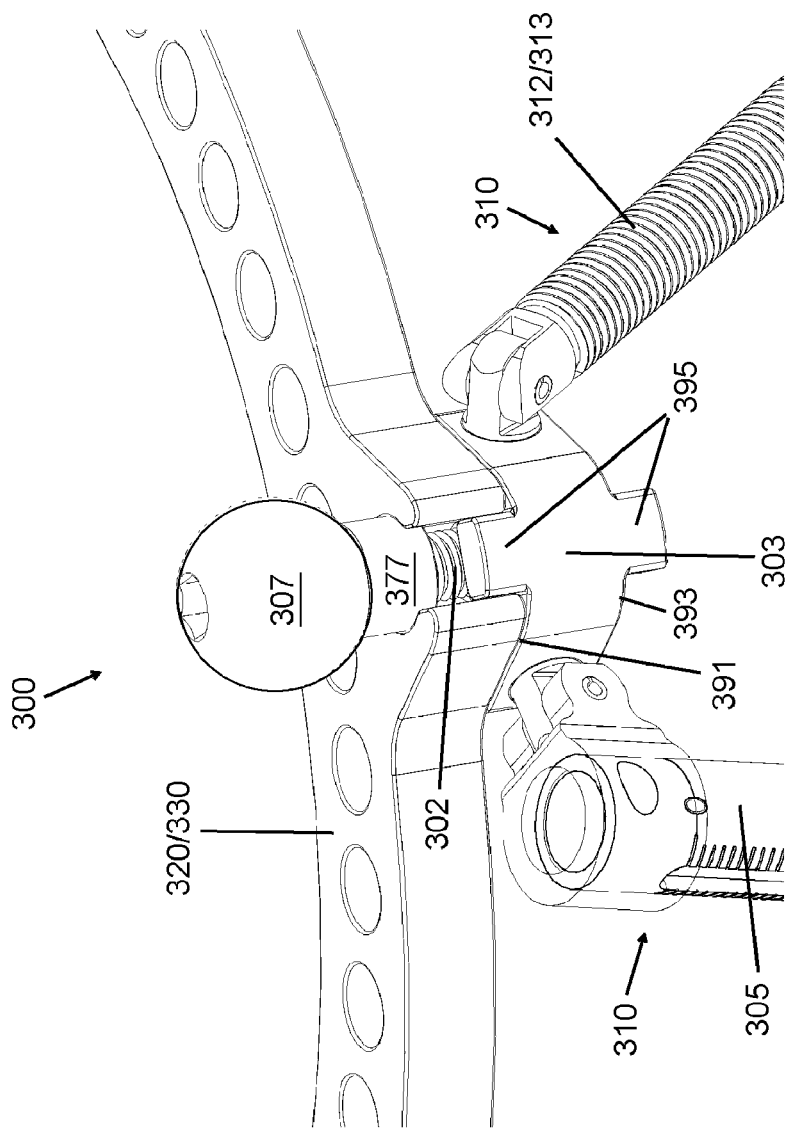
FIG. 66 is an elevational perspective view of the external bone fixation system of FIG. 59 illustrating a connection mechanism coupling a pair of strut assemblies to a platform.

As shown in FIG. 52, a bottom surface of the adjustment knob 207 may also include radially or laterally extending grooves 280b that correspond to the radially or laterally extending grooves 280b in a top surface of the nut 206. As shown in FIGS. 51, 52 and 59, compression springs 218b may be positioned between and partially within the corresponding radially or laterally extending grooves 280b, 280b of the nut 206 and the adjustment knob 207. The compression springs 218b and the radially or laterally extending grooves 280b, 280b of the nut 206 and the adjustment knob 207 may be configured such that the nut 206 is naturally or neutrally biased eccentric to the long axis of the strut assembly 210 or strut barrel 205 within the cavity of the strut barrel 205. The nut 206 may be naturally or neutrally biased such that the eccentric bore 288 of the nut is aligned (i.e., concentric) with the long axis of the strut assembly 210 or strut barrel 205 and the first or second strut screw 212, 213 extending through the nut 206, as shown in FIGS. 56B and 57B. In this way, the concentric threaded portion 287 of the nut 206 may be natural biased away or spaced from the first or second strut screw 212, 213 extending through the nut 206, as shown in FIGS. 56B and 57B.

Figure 57:
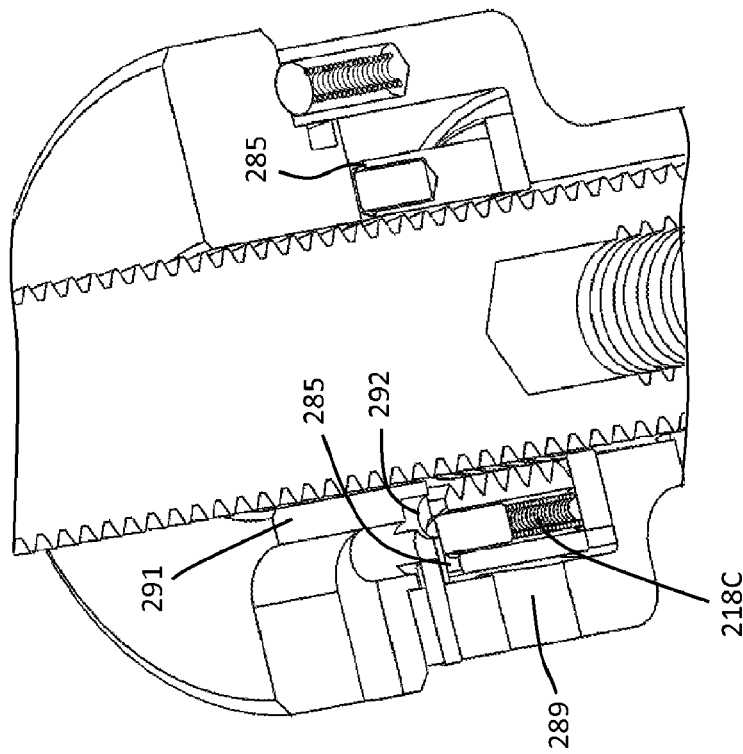
FIG. 57 is a cross-sectional perspective view of the exemplary length adjustment mechanism of FIG. 48 in a deactivated state.
Figure 56:
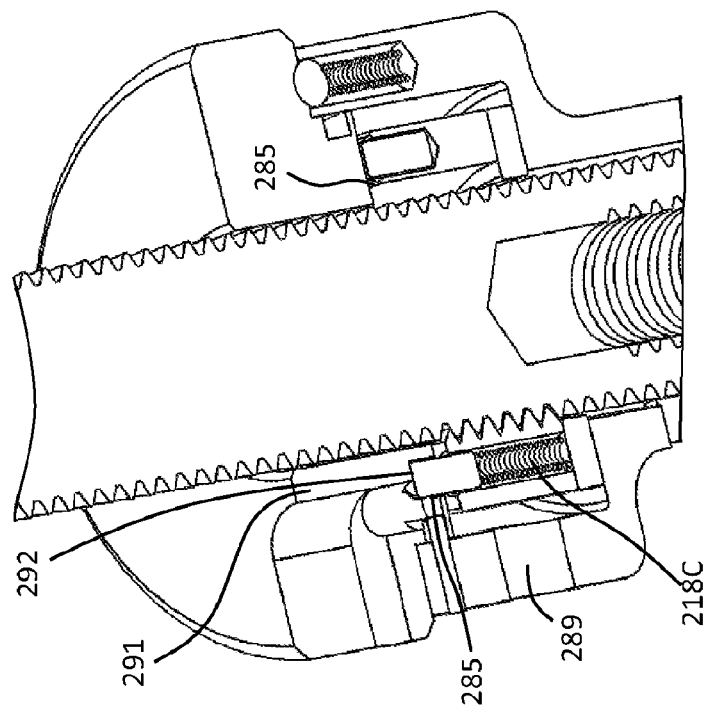
FIG. 56 is a cross-sectional perspective view of the exemplary length adjustment mechanism of FIG. 48 in an activated state.
Figure 58:
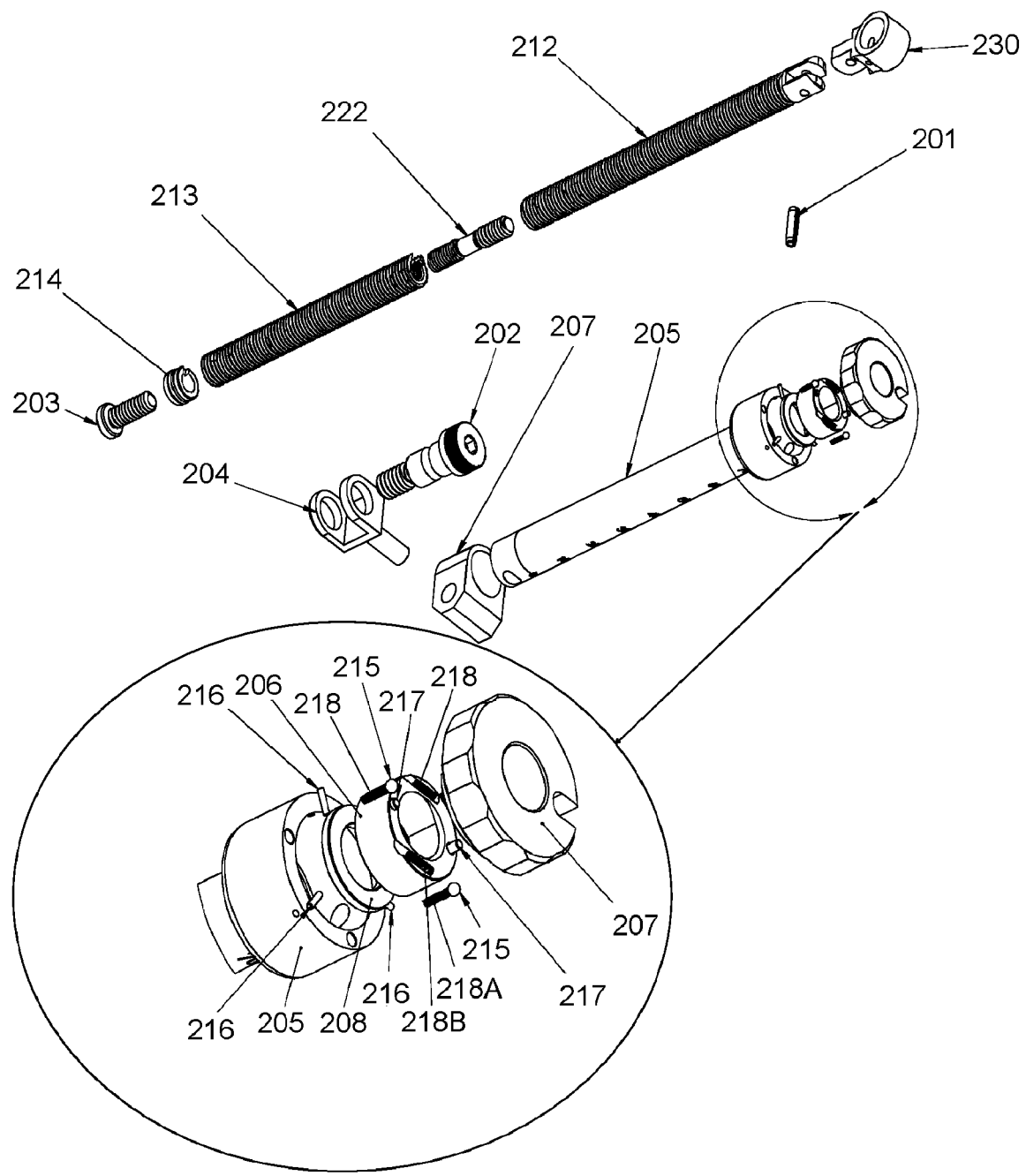
FIG. 58 is an exploded perspective view of the of exemplary length adjustment mechanism of FIG. 48.

To allow for lateral or radial re-positioning of the nut 206 away from its natural position such that the concentric threaded portion 287 of the nut 206 is concentric with and engages the first or second strut screw 212, 213 as shown in FIGS. 56A and 57A, the dowels 217, 217 may be engaged within lateral or radial grooves 285 in the underside of the adjustment knob 207 as shown in FIGS. 52 and 56A-57B. When threaded portion 287 of the nut 206 is concentric with and engages the first or second strut screw 212, 213 as shown in FIGS. 56A and 57A, rotation of the adjustment knob 207 may rotate the nut 206 such that the threaded portion 287 of the nut 206 rotates with respect to the first or second strut screw 212, 213 to translate the strut barrel 205 (and the components of the length adjustment mechanism) with respect thereto and lengthen or shorten the strut assembly 210.

As shown in FIGS. 54 and 56A-57B, the radial groove 285 of the adjustment knob 207 corresponding to the dowel 217 that is biased axially by the spring 218c may include an aperture or indentation 292 that accepts the corresponding dowel 217 therein. The mechanisms may be configured such that when the threaded portion 287 of the nut 206 is concentric with and engages the first or second strut screw 212, 213, the aperture or indentation 292 and the corresponding dowel 217 are aligned and the spring 218c naturally biases or positions the corresponding dowel 217 within the aperture or indentation 292. As shown in FIGS. 54, 55 and 56A-57B, the adjustment knob 207 may include an access aperture that allows access to the aperture or indentation 292 and, thereby, the corresponding dowel 217 to manually remove the corresponding dowel 217 from the aperture or indentation 292 and, thereby, allow the nut 206 to be naturally biased by the compression springs 218b eccentric with the first or second strut screw 212, 213 with the concentric thread portion 288 spaced from the first or second strut screw 212, 213 (i.e., disengaged).

The length adjustment mechanism may initially be provided in the natural state of the nut 206 such that it biased by the compression springs 218b eccentric with the first or second strut screw 212, 213 so that the concentric thread portion 288 is spaced from the first or second strut screw 212, 213 (i.e., disengaged) (and the eccentric bore 287 is concentric with the first or second strut screw 212, 213), as shown in FIGS. 56B and 57B. The strut barrel 205 may include an access aperture 299 extending radially therethrough to the exterior surface of the nut 206, as shown in FIGS. 55-57B and 59. The access aperture 299 may thereby allow a member (not shown) to be inserted through the access aperture 299 and radially or laterally translate or move the nut 206 within the cavity of the strut barrel 205 and with respect to the adjustment knob 207. It is noted that the lateral or radial grooves 285 in the underside of the adjustment knob 207 will allow the nut 206 and dowels 217 to radially or laterally translate or move with respect to the adjustment knob 207. The nut 206 may be radially or laterally translated (via the access aperture 299) until the dowel 217 that is biased by the spring 218c is aligned with the aperture or indentation 292 in the corresponding groove 285 of the adjustment knob 207 and thus biased therein as shown in FIGS. 56A and 56B. In this way, the eccentric threaded portion 288 of the nut 206 may be translated laterally or radially from out of engagement with the first or second strut screw 212, 213 (as shown in FIGS. 56B and 57B) and into engagement with the first or second strut screw 212, 213 (as shown in FIGS. 56A and 57A) and releasably fixed in such an arrangement. Rotation of the adjustment knob 207 may thereby rotate the nut 206 such that the threaded portion 287 of the nut 206 rotates with respect to the first or second strut screw 212, 213 to translate the strut barrel 205 (and the components of the length adjustment mechanism) with respect thereto to lengthen or shorten the strut assembly 210.

FIGS. 60-87 is illustrate another 6 DOF bone or tissue fixation systems and related fixation methods 300 include the desirable stability and mobility characteristics of a hexapod system without time consuming strut-length choices and assembly difficulties. The 6 DOF bone or tissue fixation systems and related fixation methods 300 of FIGS. 20-59 are similar to the 6 DOF bone or tissue fixation systems and related fixation methods 100 of FIGS. 1-19 and the 6 DOF bone or tissue fixation systems and related fixation methods 200 of FIGS. 20-59, and therefore like reference numerals preceded with "3" are used to indicate like aspects or functions, and the description above directed to aspects or functions thereof (and the alternative embodiments thereof) equally applies to the systems and methods 300.

As shown in FIGS. 60-68, the system 300 differs from the system 100 and the system 200 in the inclusion of fiducial markers or identifiers 307 as points of reference and/or measure. The fiducial markers 307 may be configured to assist in the identification and/or manipulation of the orientation of each strut-platform joint and the length of each strut. For example, a first platform 320 of the system 300 may be coupled to a first bone segment and a second platform 330 of the system 300 may be coupled to a second bone segment, and then the system 300 may be manipulated, that is, moved, such that the first bone segment and a second bone segment are aligned in a desired position. This alignment may be changed over time to complete the deformity correction process. One of the bone segments may be a reference segment. The other segment, the moving segment, may be moved to align with the reference segment. The fiducial markers 307 of the system 300 may provide identification (e.g. via clinical evaluation and/or imaging) of position and/or orientation of the strut assemblies 310 as shown in FIGS. 60-68, to facilitate a method or process of configuring a strut to achieve a needed or desired orientation of the bone segments. In some embodiments, the fiducial markers 307 of the system 300 may provide identification of the position and/or orientation of the coupling mechanisms that are provided at the end portions of pairs of struts 310 to couple the struts 310 to a respective platform 320, 330 as shown in FIGS. 60-68, and thereby the struts 310 themselves via extrapolation, to facilitate a method or process of configuring a strut to achieve a needed or desired orientation of the bone segments. In this way, the markers 307 may facilitate a method or process of configuring struts 307 of the system 300 to achieve a needed or desired orientation of the bone segments, such as a method or process disclosed in U.S. Pat. No. 8,419,732, which is expressly incorporated herein in its entirety. In some embodiments, the method or process may utilize the markers 307 to determine a "current" position and/or orientation of the struts 307 and a "corrected" position and/or orientation of the struts. In some embodiments, the method or process may determine the how the markers 307 (and thereby the corresponding struts 310 should be positioned and/or oriented in situ.

As shown in FIGS. 60-71 and 75-78, the markers 307 may be spherical knobs or heads of a shoulder screw 302 that couples an attachment base 303 that couples a pair of adjacent strut assemblies 310 to a respective platform 320, 330. In this way, the markers 307 may be utilized to torque the shoulder screw 302 to threadably removably couple the attachment base 303 (and thereby the strut assemblies 310 coupled thereto) to a respective platform 320, 330, as explained further below. The markers 307 may be positioned on the exterior of the system 300, such as past an outer end of a respective platform 320, 330. The markers 307 may be configured to visually appear when imaged, such as when x-rayed. The markers 307 may include at least one marker that is visually different in some than the other markers 307. For example, as shown in FIGS. 60-71 and 75-78 the markers 307 include a unique relatively smaller spherical marker at one end of the system 300 in a location or position on the respective platform 320, 330. The unique marker 307 may be used as a reference marker 307 to determine the orientation and position of the system 300 and the strut assemblies 310, such as by the method described above. Further, such a unique marker 307 may be utilized as a reference to effectuate the positions and/or orientations determined by the aforementioned method.

As shown in FIGS. 60-71 and 75-78, the markers 307 may be spherical knobs or heads of a shoulder screw 302 that removably fix an attachment base 303, to which a pair of adjacent strut assemblies 310 are movably coupled, to a respective platform 320, 330. The markers 307 may thereby be positioned on the exterior of the construct 315 and clearly visible in profile. Further, the markers 307 may be manually engageable to manually screw the shoulder screws 302 into their respective platform 320, 330.

The markers 307 may also initially be utilized to unpack or ready the system 300 by removing the shoulder screws 302 to separate the construct 315 from end plates 371 and a connecting rod 373 extending therebetween, as shown in FIGS. 60-64. Each end plate 371 may be coupled to three base plates 303 at an end of the construct 315 with each base plate 303 coupled to a pair of strut assemblies 310. As shown in FIGS. 60-64, the shoulder screws 302 may each threadably couple through a respective slot or aperture in an end plate 371 and into a respective base plate 303 to clamp the end plate 371 between a collar or shoulder 377 and/or the marker 307 of the shoulder screws 302 and the respective base plates 303. The connecting rod 373 may threadably couple to, and extend between, the base plates 371. The end plates 371 and the connecting rod 373 may thereby fix the base plate 303, and thereby the strut assemblies 310, together and prevent the strut assemblies 310 from extending and retracting.

Figure 67:
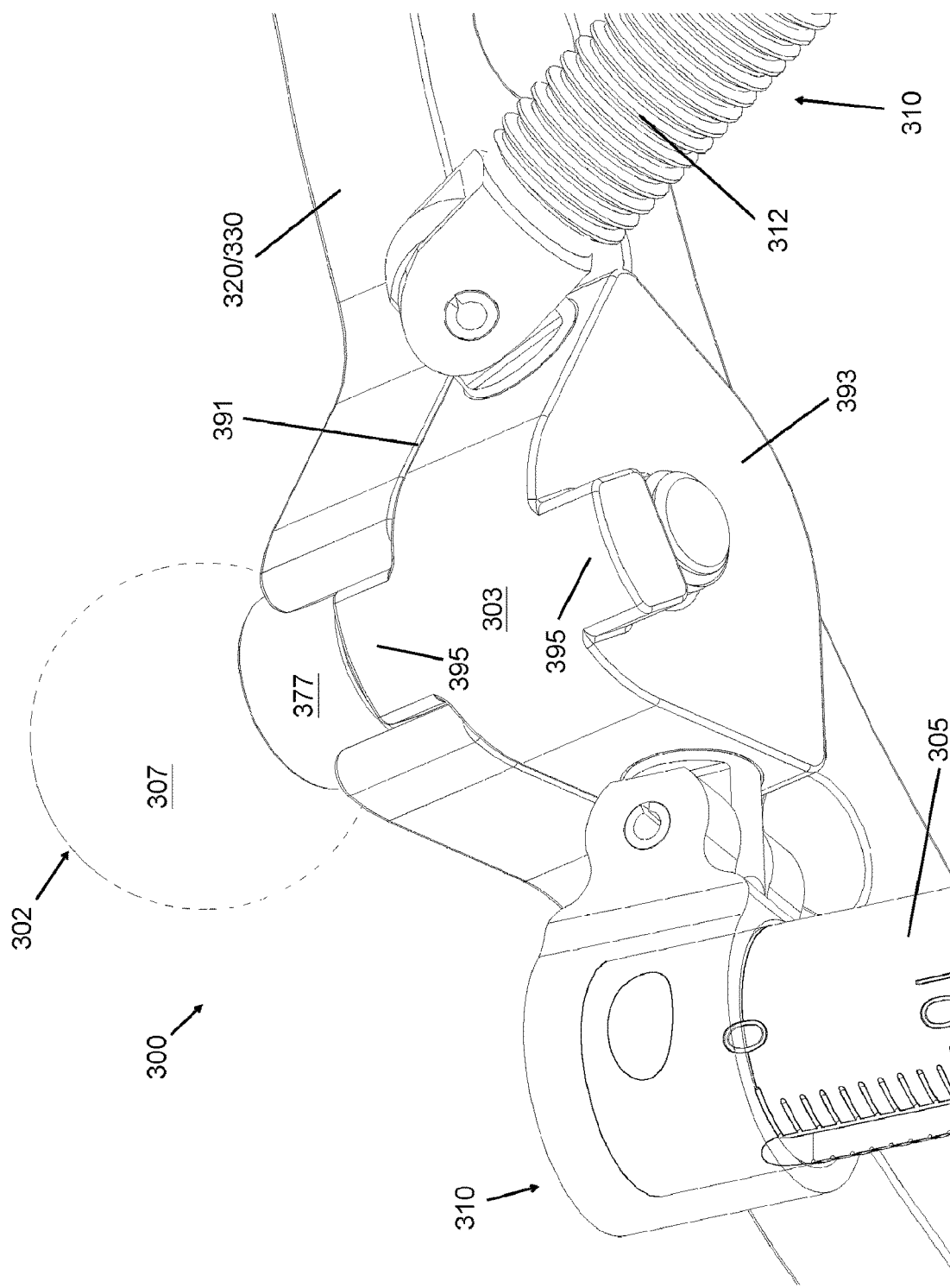
FIG. 67 is a bottom perspective view of the external bone fixation system of FIG. 59 illustrating a connection mechanism coupling a pair of strut assemblies to a platform.
Figure 68:
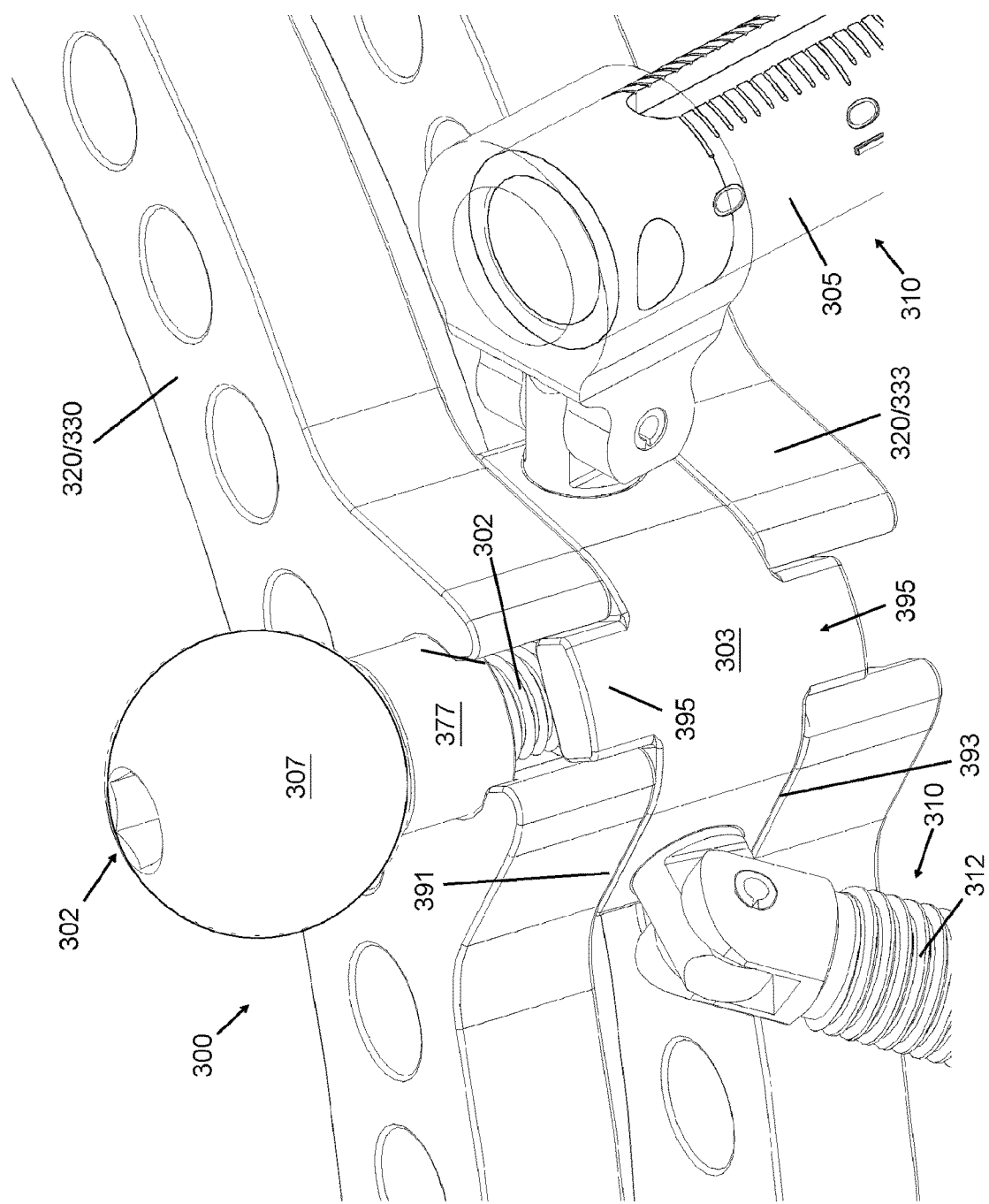
FIG. 68 is an elevational perspective view of the external bone fixation system of FIG. 59 illustrating a connection mechanism coupling a pair of strut assemblies to a pair of platforms.
Figure 69:
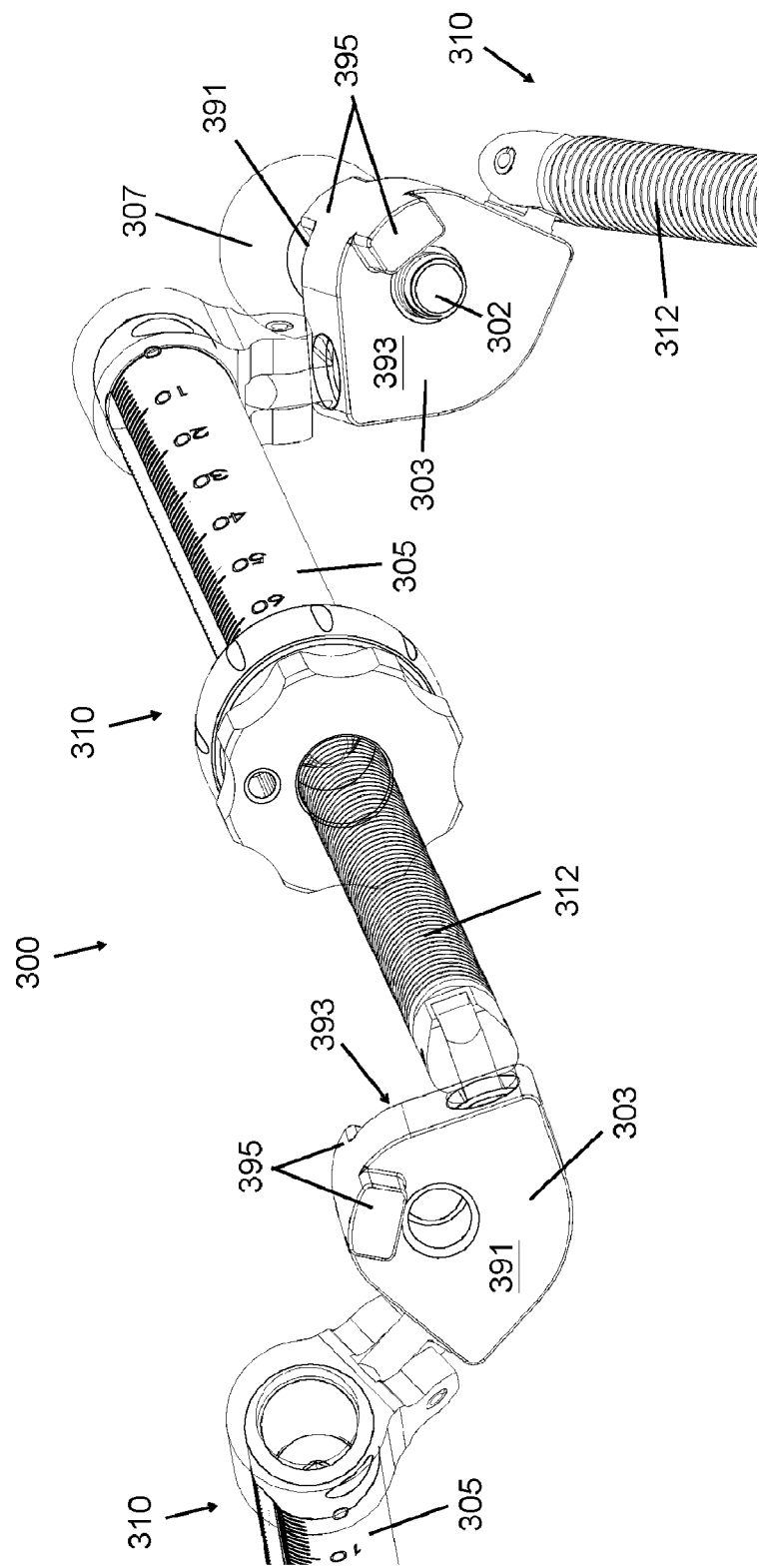
FIG. 69 is a perspective view of the external bone fixation system of FIG. 59 illustrating strut-platform connection mechanisms.
Figure 70:
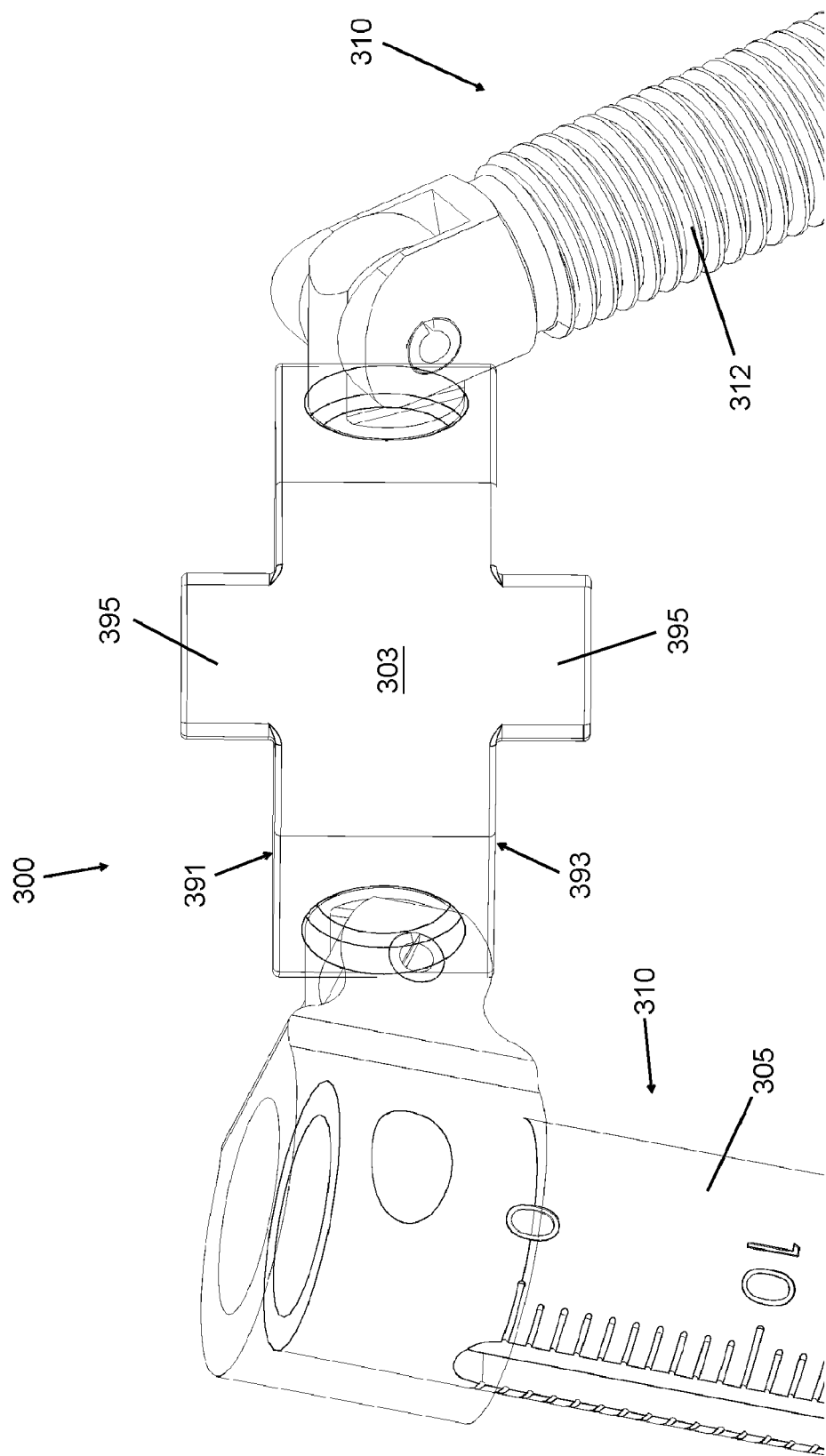
FIG. 70 is a side view of the external bone fixation system of FIG. 59 illustrating strut-platform connection mechanisms.
Figure 71:
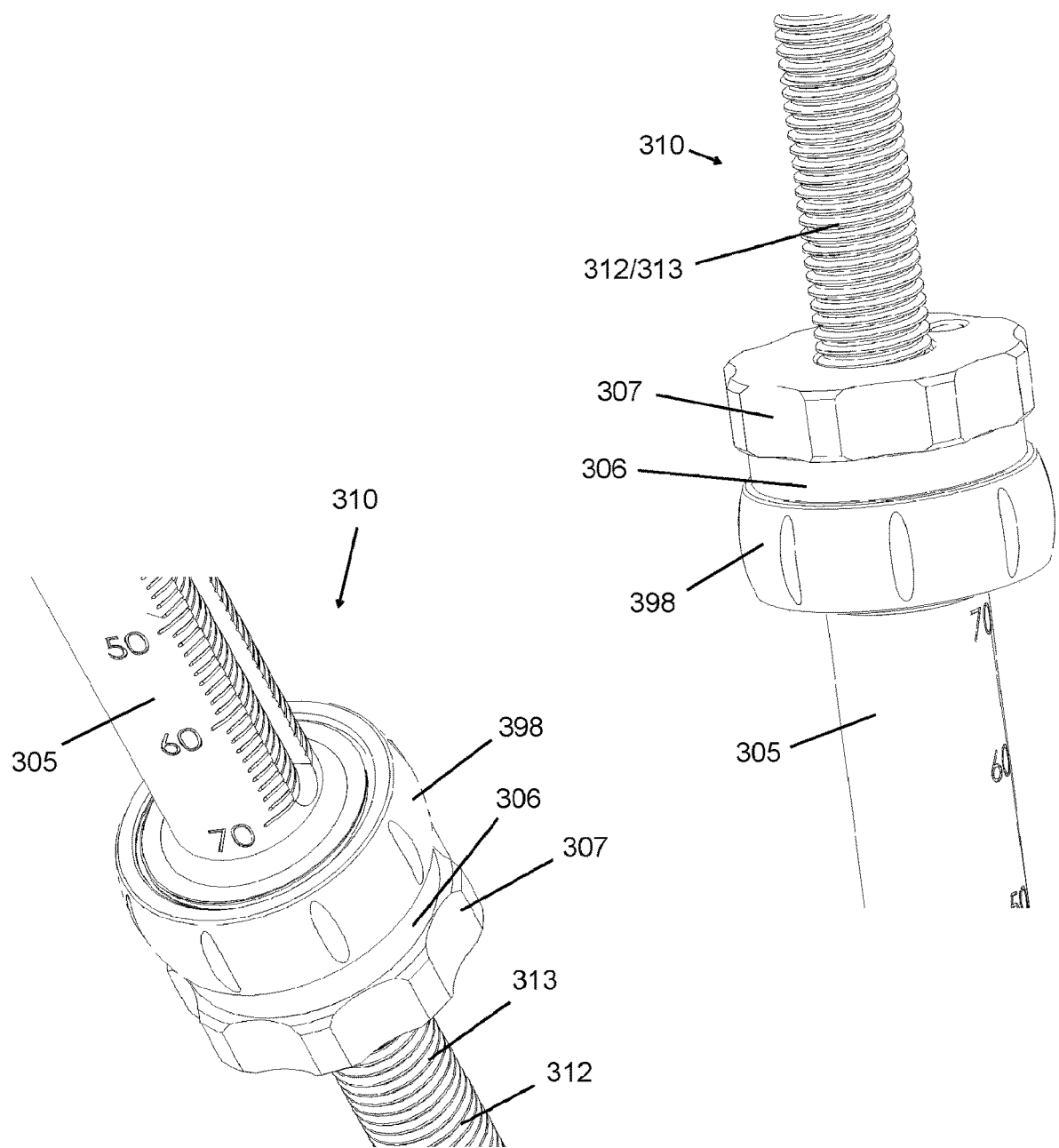
FIG. 71 is a perspective view of exemplary length adjustment mechanisms of strut assemblies of the external bone fixation system of FIG. 59.
Figure 72:
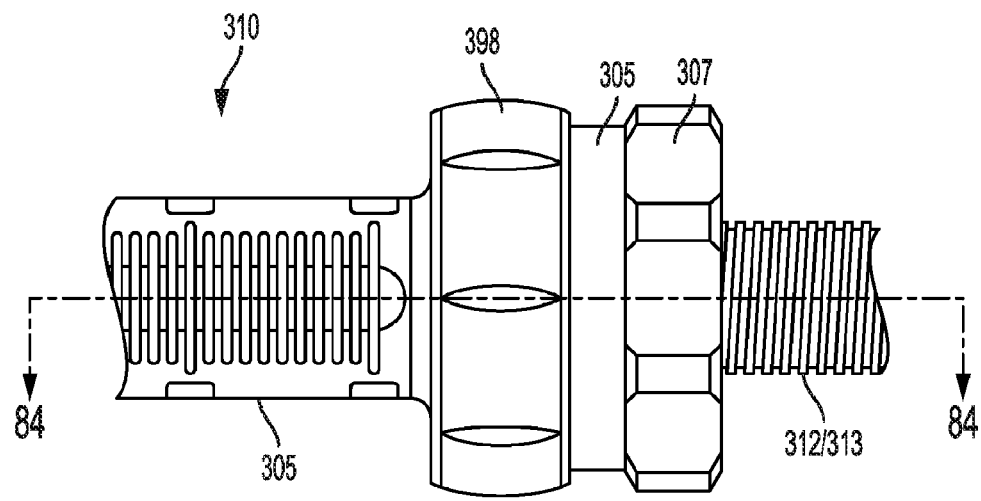
FIG. 72 is a side view of the length adjustment mechanisms of FIG. 71.
Figure 73:
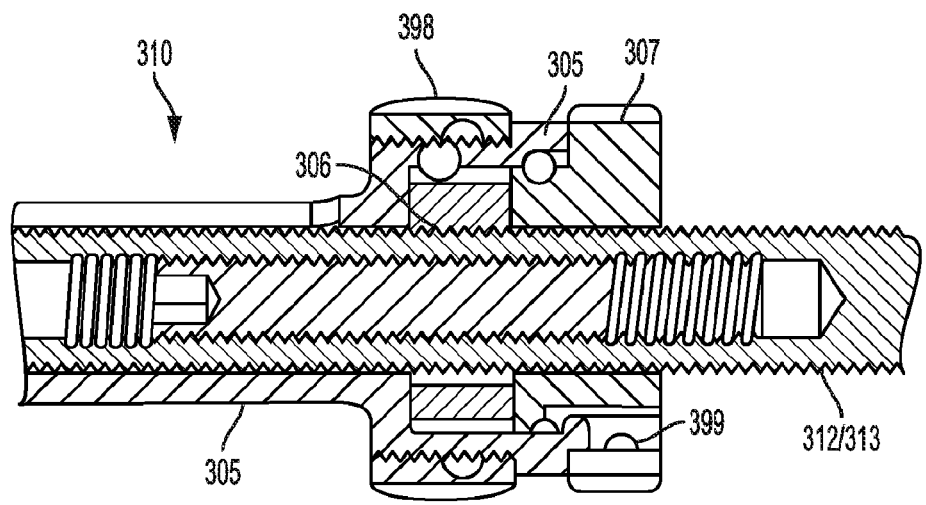
FIG. 73 is a cross-sectional view of the length adjustment mechanisms of FIG. 71.
Figure 74:
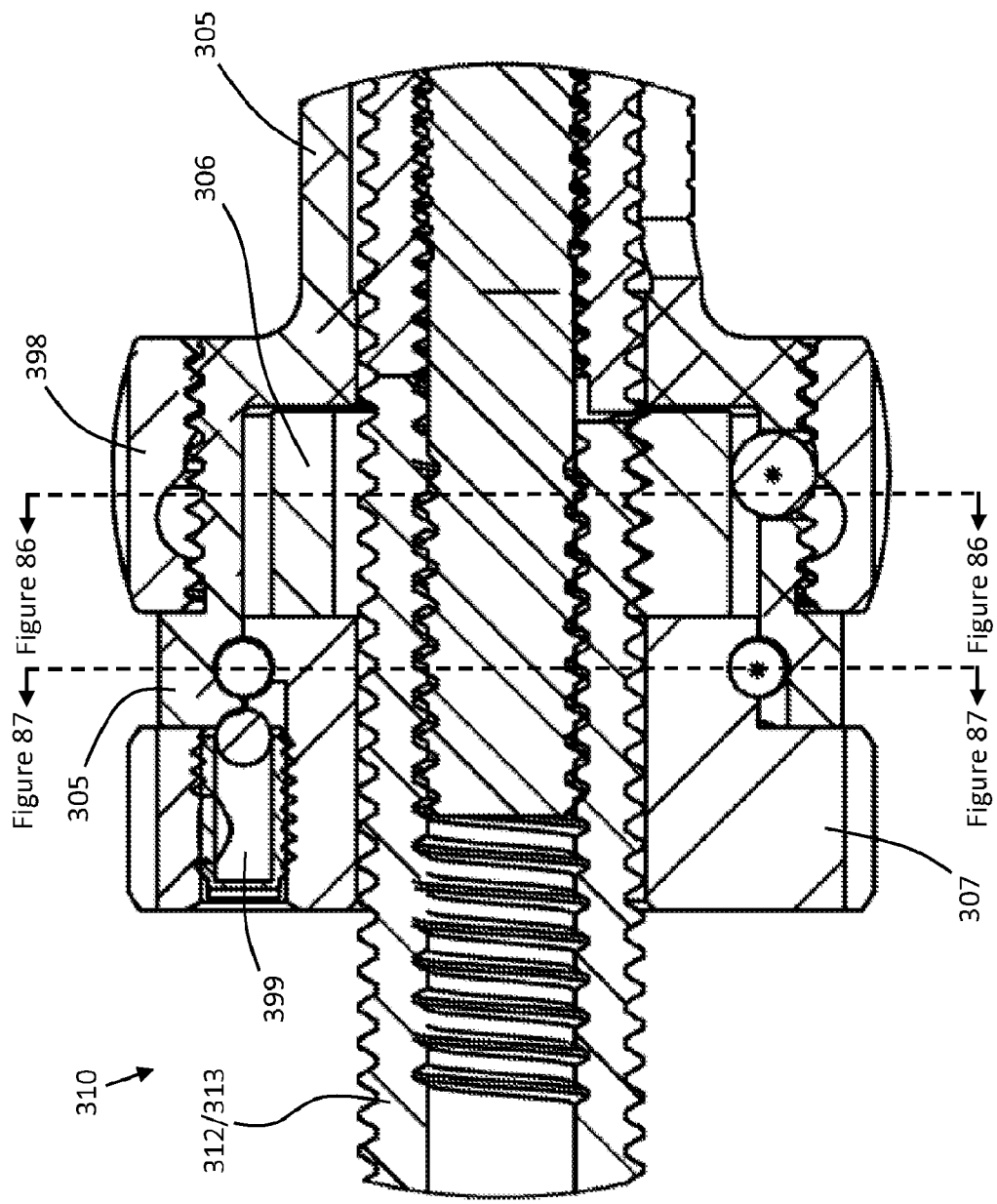
FIG. 74 is another cross-sectional view of the length adjustment mechanisms of FIG. 71.
Figure 75:
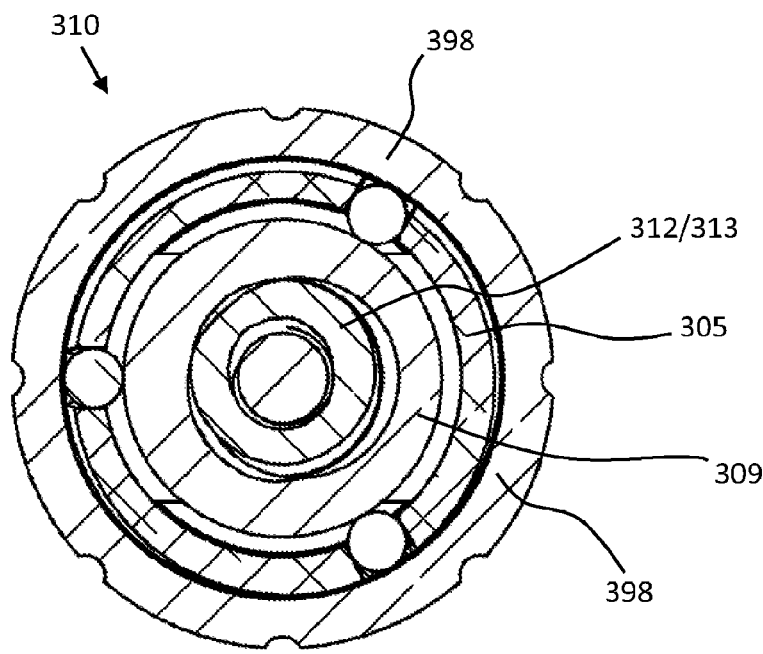
FIG. 75 is another cross-sectional view of the length adjustment mechanisms of FIG. 71.
Figure 76:
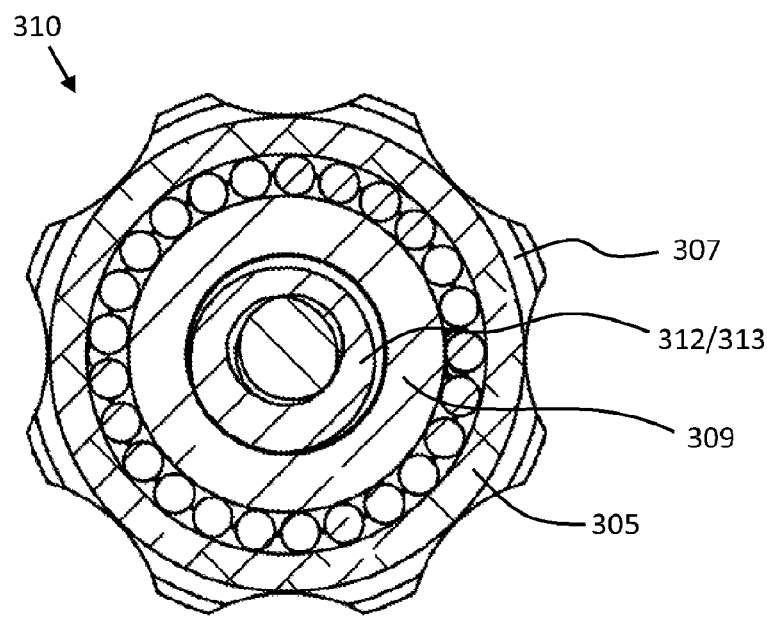
FIG. 76 is another cross-sectional view of the length adjustment mechanisms of FIG. 71.
Figure 77:
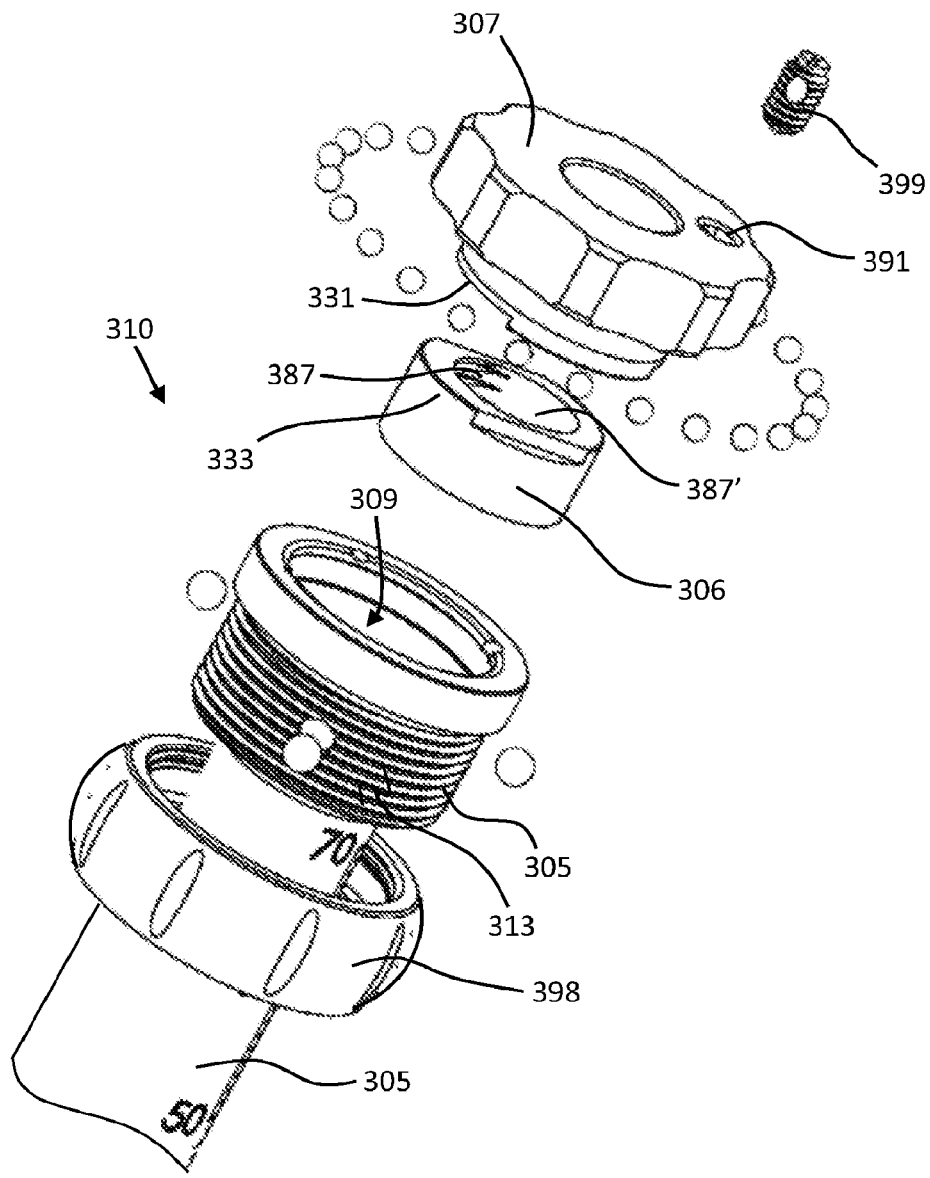
FIG. 77 is a perspective exploded view of the length adjustment mechanisms of FIG. 71.
Figure 78:
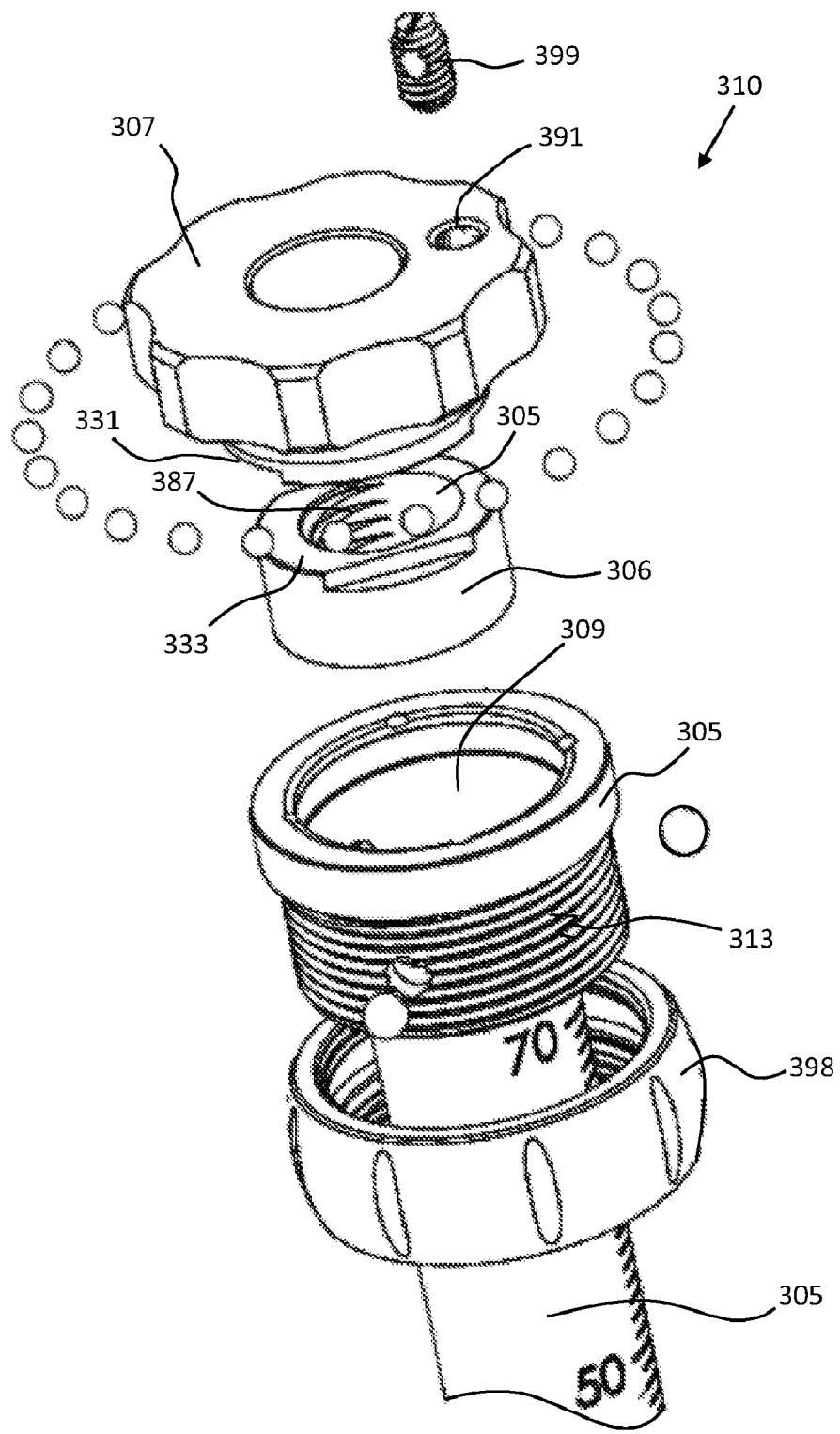
FIG. 78 is another perspective exploded view of the length adjustment mechanisms of FIG. 71.
Figure 79:
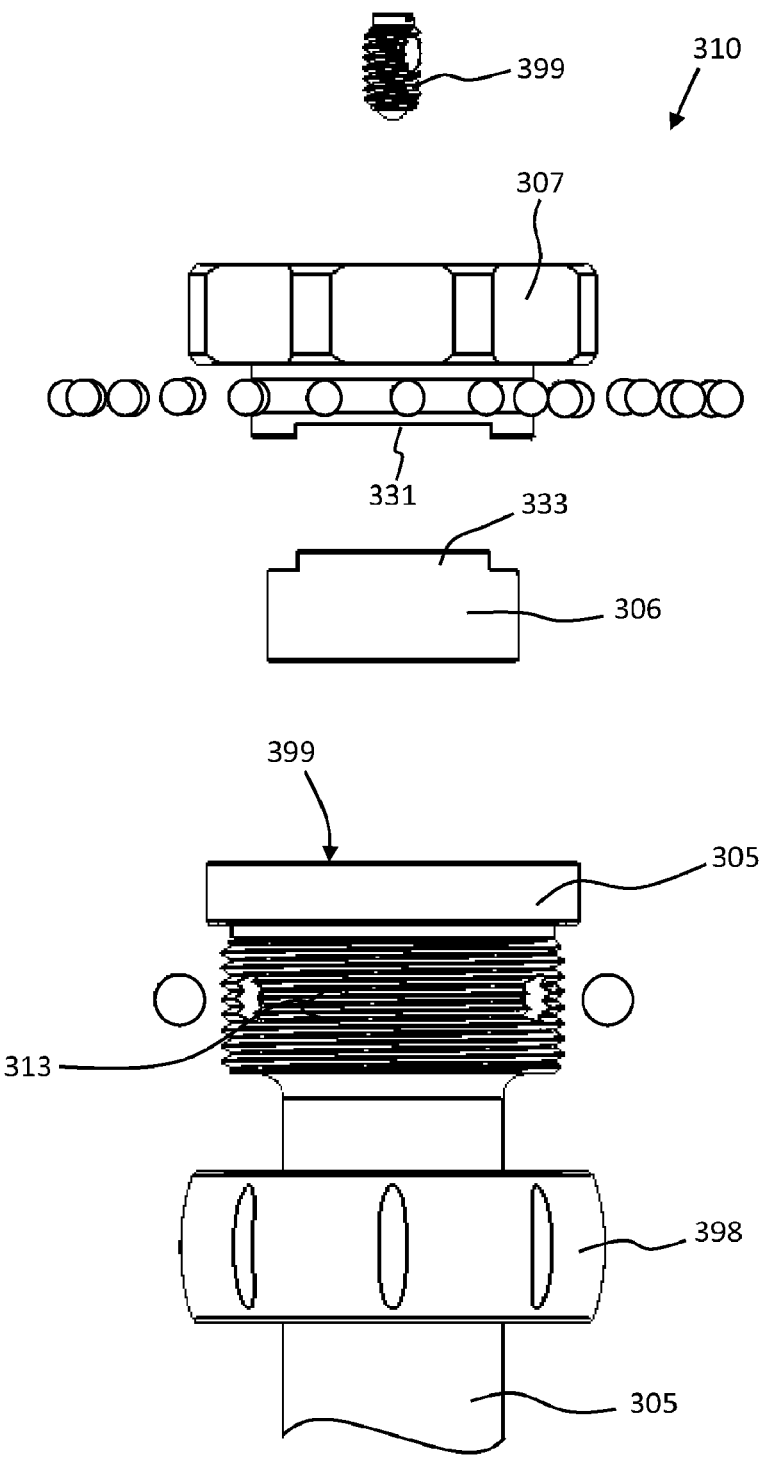
FIG. 79 is a side exploded view of the length adjustment mechanisms of FIG. 71.
Figure 80:
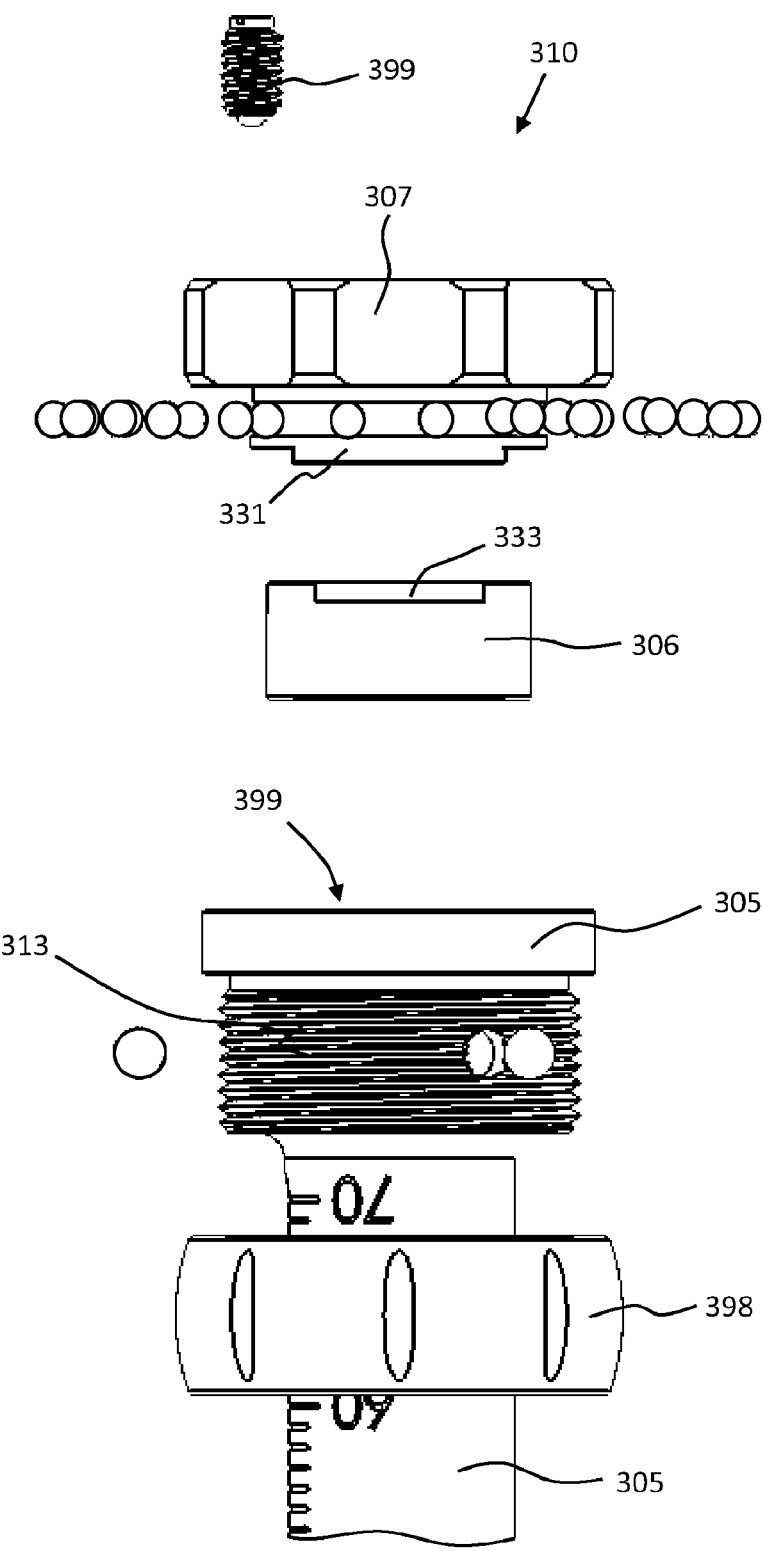
FIG. 80 is another side exploded view of the length adjustment mechanisms of FIG. 71.
Figure 81:
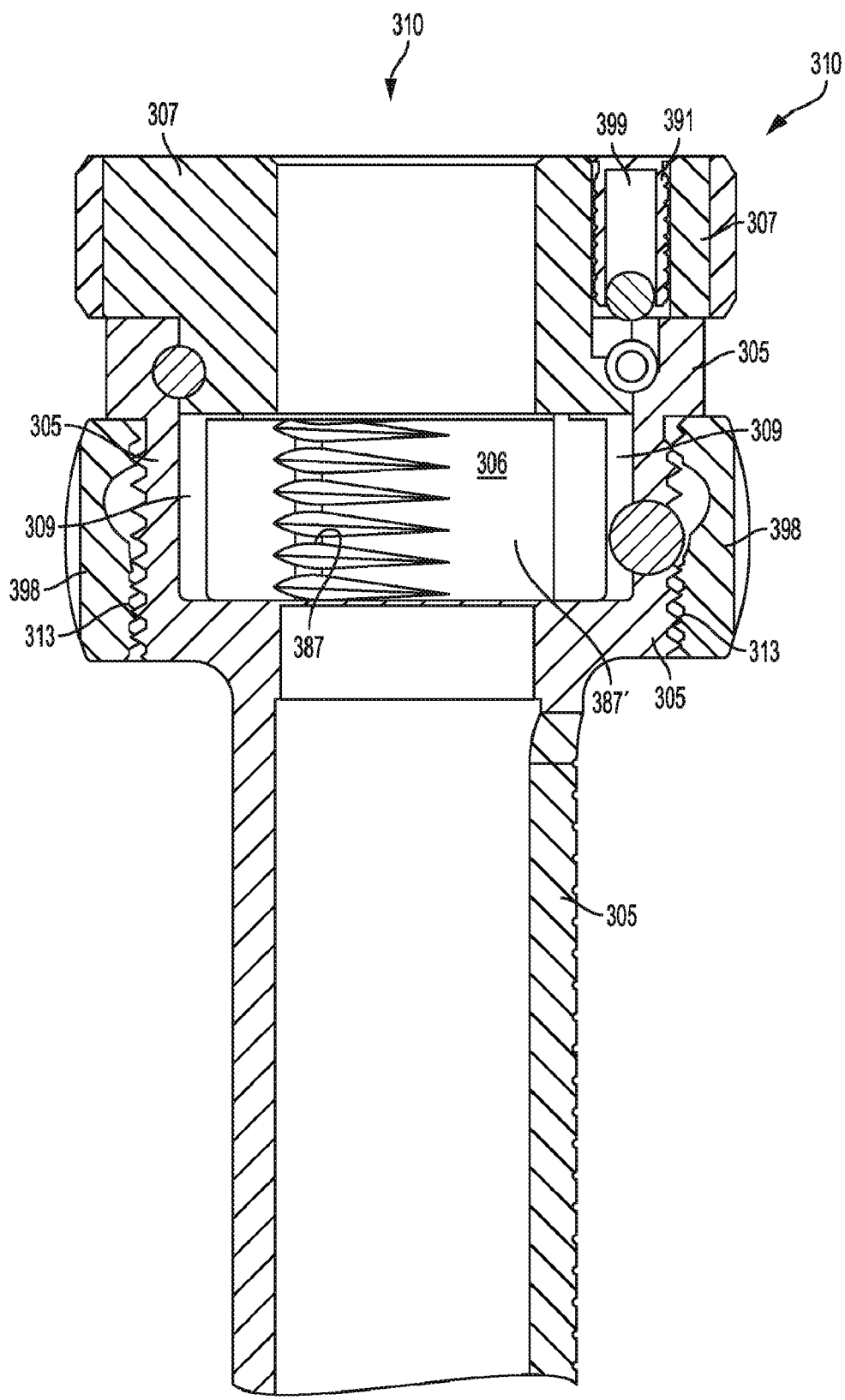
FIG. 81 is another cross-sectional view of the length adjustment mechanisms of FIG. 71.

As shown in FIGS. 66-81, opposing ends of a pair of adjacent strut assemblies 310 may be movably coupled to substantially opposing lateral sides of a corresponding base plate 303. Each strut assembly 310 may be rotatably coupled to a side of a corresponding base plate 303 such that the strut assembly 310 is rotatable about at least two axis, as shown in FIGS. 66-81. The base plate 303 may be triangular in shape with curved outer lateral surfaces. The base plate 303 may include an outer longitudinal engagement surface 391 and an inner longitudinal engagement surface 393, as shown in FIGS. 66-81. The outer longitudinal engagement surface 391 and/or an inner longitudinal engagement surface 393 may be planar and/or configured to mate with corresponding surfaces of studs 50 projecting radially from the platform 320, 330, as shown in FIGS. 67-76. The studs 50 may also inner and outer surfaces corresponding to the engagement surfaces 391, 393 of the base plates 303 so that the base plates 303 may be coupled to and abut either the inner or outer corresponding surfaces of the studs 50, as shown in FIGS. 67-76. Further, as shown in FIGS. 67, 68 and 76, the base plates 303 may be positioned between and coupled to a pair of platforms 320, 330 such that both the inner and outer engagement surfaces 391, 393 of the base plates 303 engages a corresponding portion of the studs 50 of the pair of platforms 320, 330.

As also shown in FIGS. 66-81, the base plates 303 may also include a projection 395 extending from the inner and/or outer engagement surfaces 391, 393. The projection 395 may be position on a laterally and/or radially outward portion of the engagement surfaces 391, 393. The projections 395 may be configured to mate within a corresponding aperture, slot, recess or the like in the studs 50 of the platforms 320, 330, as shown in FIGS. 67-76. The slot of the platforms 320, 330 may be open at the outer lateral and/or radial end of the studs 350 to allow the projection 395 to be translated or slid therein. In addition to the slot corresponding to the projections 395 of the base plates 303, the studs 350 of the platforms 320, 330 may also include and aperture or portion extending from the slot (or separated from) configured to allow a shoulder screw 302 to threadably engage and extend therethrough, as shown in FIGS. 66-81. The base plates 303 may also include and aperture configured to threadably engage with the shoulder screw 302. In this way, a projection 395 may be positioned within a corresponding slot of a stud 350, an engagement surface 391, 393 of the corresponding base plate 303 may engage or abut a corresponding surface of the stud 350, and shoulder screw 302 may threadably engage and extend into the stud 350 and the base plate 303 to rigidly removably couple the base plate 303 (and the strut assemblies 310 coupled thereto) and the corresponding platform(s) 320, 330, as shown FIGS. 67-76. In some embodiments, the aperture or slot of the studs 350 of the platforms 320, 330 that allow the shoulder screws 302 to pass therethrough may include a bevel or countersink extending thereabout into the inner and/or outer engagement surfaces 391, 393 to accept a corresponding collar or shoulder 377 of the shoulder screws 302 therein, as shown FIGS. 67-76. The countersink and the corresponding collar 377 may aid in fixedly or rigidly coupling the base plates 303 (and the strut assemblies 310 coupled thereto) and the corresponding platform(s) 320, 330.

As shown in FIGS. 82-92, the system 300 also differs from the system 100 and the system 200 in the configuration of the length adjustment mechanisms of the strut assemblies 310 that are configured to selectively vary the arrangement of the strut barrel 305 and first or second threaded rod 312, 313. As shown in FIGS. 82-92, the strut barrel 305 includes a head portion at the free end thereof that includes outer threads 313 and a cavity 309. The head portions of the strut barrel 305 also includes a plurality of the apertures extending from the outer threads 313 to the cavity 309. In some embodiments, at least three apertures are provided and may be radially extending and evenly circumferentially spaced. As also shown in FIGS. 82-92, a ball bearing or other member may be carried, housed or otherwise positioned at least partially within the apertures of the head portion of the strut barrel 305. In this way, the ball bearing or other members may be able to move at least partially into, or at least partially out of, the cavity 309 to differing degrees.

Figure 88:
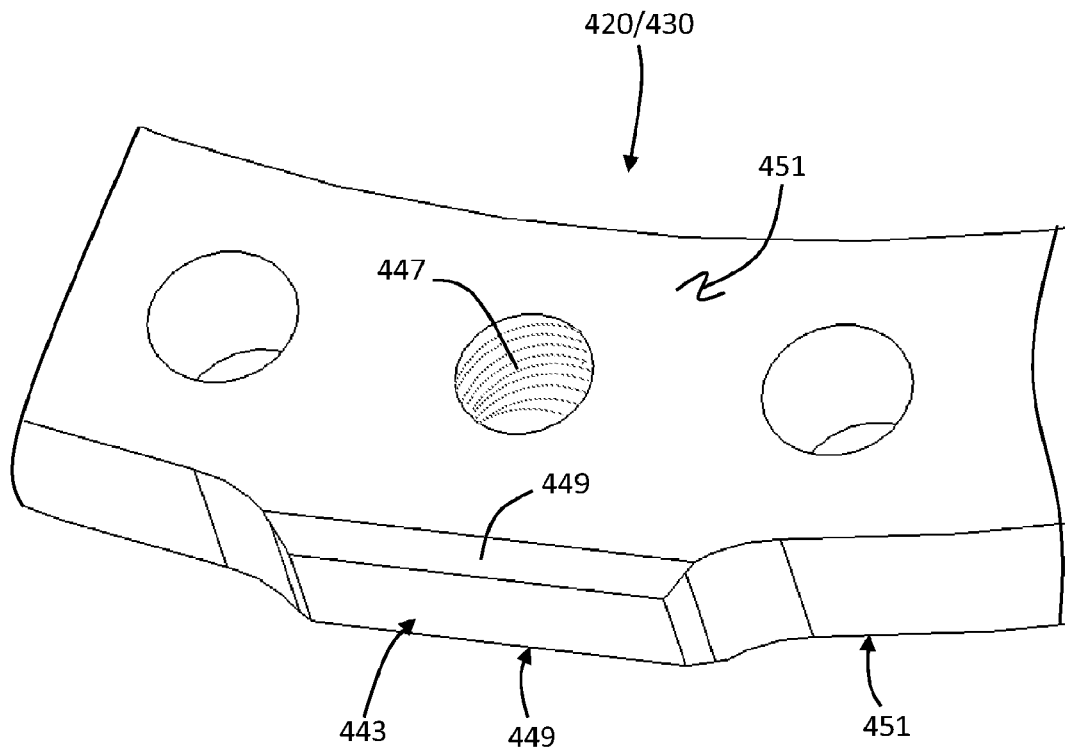
FIG. 88 is an enlarged elevational perspective view of the platform of FIG. 86.
Figure 89:
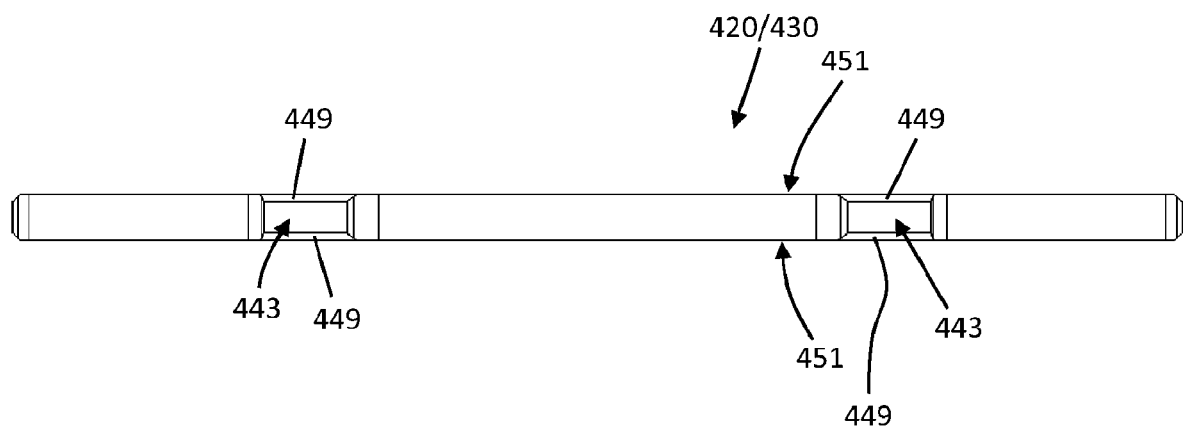
FIG. 89 is a side perspective view of the platform of FIG. 86.
Figure 92:
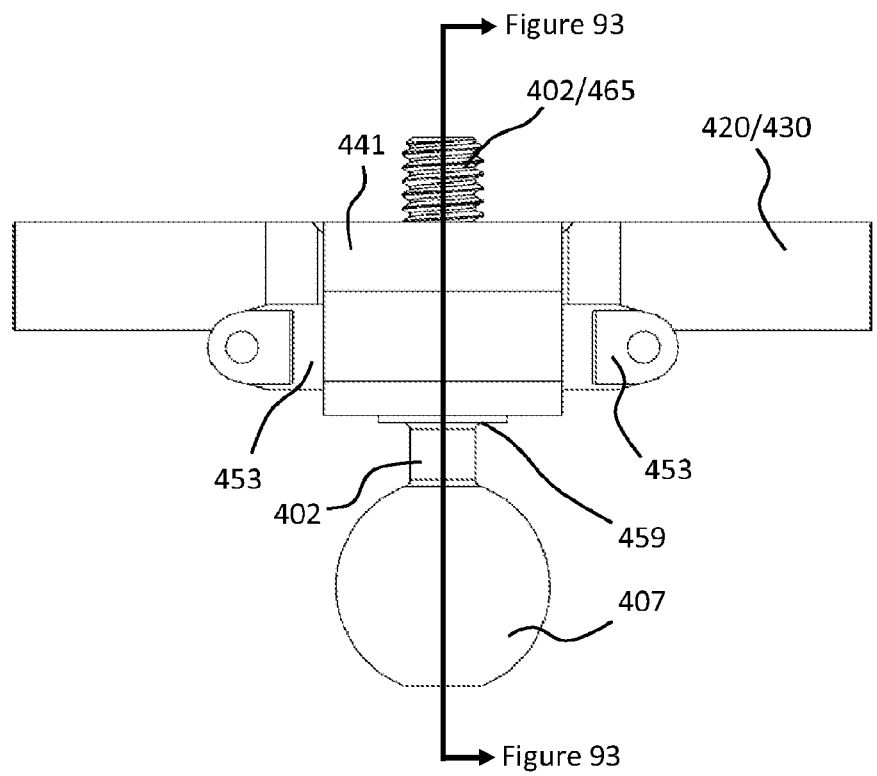
FIG. 92 is a side view of the strut-platform connection mechanism of FIG. 90.

The length adjustment mechanisms of the strut assemblies 310 may further include a adjust nut 306 with a bore that includes a threaded portion 387 and a non-threaded portion 387', as shown in FIGS. 88, 89 and 92. The adjust nut 306 and the cavity 309 may be configured such that the adjust nut 306 can be positioned or housed within the cavity 309 with additional space or a portion of the cavity 309, as shown in FIG. 92. Stated differently, the cavity 309 may be larger than the adjust nut 306 such that the adjust nut 306 may be able to translate within the cavity 309, as shown in FIG. 92. The length adjustment mechanisms of the strut assemblies 310 may also include a release nut 398 that is threadably engaged with the external threads 313 of the head portion of the strut barrel 305. The release nut 398 may include an inner threaded surface with a groove or recess therein, as shown in FIGS. 89 and 92.

The groove and threaded portions of the inner surface of the release nut 398 may thereby move the ball bearings or other members in/out of the cavity 309 of the head portion of the strut barrel 305, as shown in FIG. 92. In this way, the release nut 398 may be adjusted to either push the ball bearings or other members at least partially into the cavity 309 via the threaded portions as shown in FIG. 92, or to a positioned such that the inner groove is aligned with the ball bearings or other members to allow the ball bearings or other members to move therefrom and at least partially out of the cavity 309. The adjust nut 306 positioned within the cavity 309 may thereby be biased by the ball bearings or other members to a position concentric with the threaded rod 312, 313 extending through the strut barrel 305, or allow the adjust nut 306 move to a position eccentric with the threaded rod 312, 313. In the concentric arrangement of the adjust nut 306 and the threaded rod 312, 313, the threaded portion 387 of the adjust nut 306 may be engaged with the threads of the threaded rod 312, 313, and in the eccentric position of the adjust nut 306 the threaded portion 387 of the adjust nut 306 may be disengaged with the threads of the threaded rod 312, 313 and the non-threaded portion 387' may engaged with the threads of the threaded rod 312, 313. It is noted that when the release nut 398 is position to allow the adjust nut 306 to move within the laterally cavity 309, the force between the threads of the threaded portion 387 and the threaded rod 312, 313 may act to move the release nut 398 into the eccentric position. In such a state, the non-threaded portion 387' may engaged with the threads of the threaded rod 312, 313 (if any portion of the adjust nut 306 engages therewith) to allow the threaded rod 312, 313 to freely axially or longitudinally translate through the strut barrel 305.

As shown in FIGS. 82-92, the length adjustment mechanisms of the strut assemblies 310 may also include an adjustment knob 307 with lower neck region that is configured to be positioned within the cavity 309 above the adjust nut 306. The lower neck region of the adjustment knob 307 and an upper portion of the cavity 309 may include grooves, races or channels to capture a plurality of ball bearings or any other rotational providing members therebetween, as shown in FIGS. 88-92. The adjustment knob 307 may also include a threaded longitudinally extending aperture 391 that extends to the top or upper rim of the head portion of the strut barrel 305. As shown in FIGS. 88-92, the top or upper rim of the head portion of the strut barrel 305 may include circumferentially spaced indentations, and a spring plunger 399 or other member threadably engaged within the aperture 391 such that the plunger 399 engages the indentations when aligned therewith. The plunger 399 and the indentations may thereby provide a tactile indication of the rotational position of the adjustment knob 307 with respect to the strut barrel 305.

Figure 90:
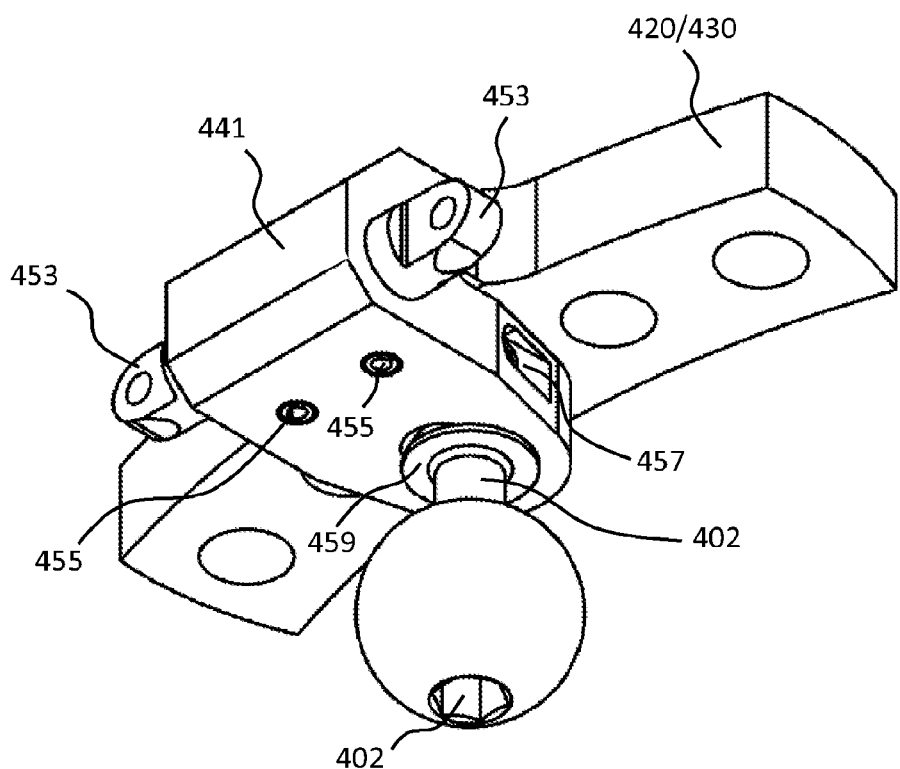
FIG. 90 is an exterior bottom perspective view of the strut-platform connection mechanism of FIG. 83 couple to the platform of FIG. 86.
Figure 91:
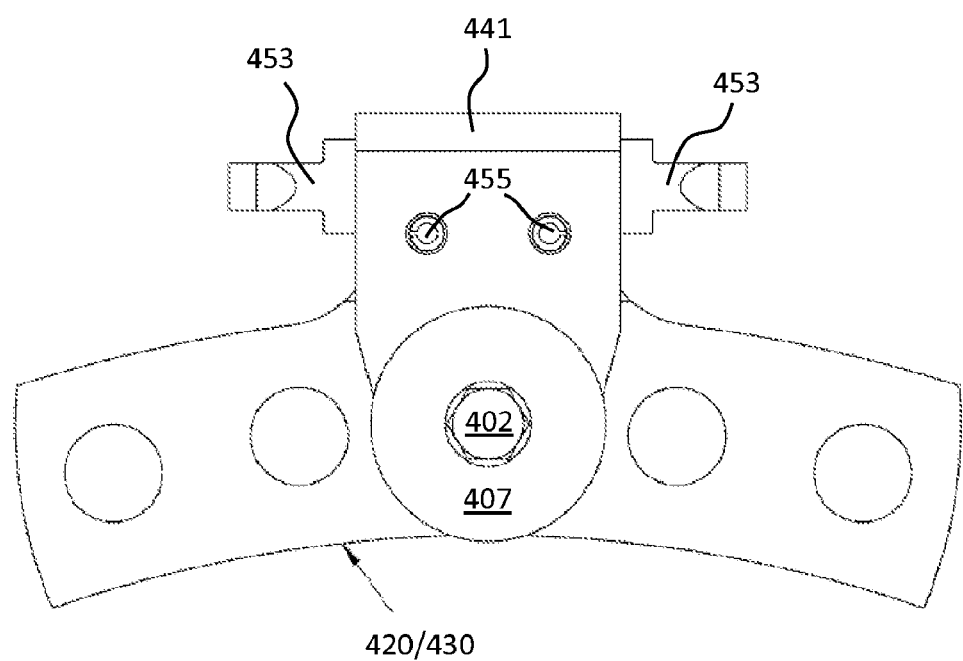
FIG. 91 is a top view of the strut-platform connection mechanism of FIG. 90.

The lower end or portion of the adjustment knob 307 may also include at least one slot 331 (or projection) extending at least partially across the cavity 309, as shown in FIG. 90. Similarly, the upper end or portion of the adjust nut 306 may include at least one projection 333 (or slot) extending at least partially across the cavity 309 and configured to mate with the slot 331 of the adjustment knob 307, as shown in FIG. 90. The slot 331 of the adjustment knob 307 and the projection 333 of the adjust nut 306 may thereby mate such that rotation of the adjustment knob 307 effectuates rotation of the adjust nut 306. In this way, a user may rotate the adjustment knob 307 to rotate the adjust nut 306 within the cavity 309 of the head portion of the of the strut barrel 305. As discussed above, the user may also rotate the release nut 398 to adjust its longitudinally or axial position to translate the ball bearings with respect to the cavity 309 to force the nut to be concentric with the threaded rod 312/313 to engage the threaded portion 287 therewith. In such an arrangement, the adjustment knob 307 can be rotated to rotate the nut 398 and force the threaded rod 312/313 through the strut barrel 305 to lengthen or shorten the strut assembly 310, depending upon the direction of rotation. The adjustment knob 307 may thereby be utilized for fine length adjustment of the strut assembly 310. For gross adjustment of the length of a strut assembly 310, the user may rotate the release nut 398 to adjust its longitudinally or axial position to align the groove with the ball bearings to allow the ball bearing to move away from the cavity 309 and, thereby, allow the adjust nut 306 to move eccentric with the threaded rod 312/313. As noted above, in the eccentric position of the adjust nut 306, the threaded portion is not in engagement with the threaded rod 312/313 to allow the threaded rod 312, 313 to freely axially or longitudinally translate through the strut barrel 305.

FIGS. 82-105 is illustrate additional 6 DOF bone or tissue external fixation systems and related fixation methods 400 that include the desirable stability and mobility characteristics of a hexapod system without time consuming strut-length choices and assembly difficulties. The external bone or tissue fixation systems and related fixation methods 400 of FIGS. 82-105 are similar to the external fixation systems and related fixation methods 100 of FIGS. 1-19, the external fixation systems and related fixation methods 200 of FIGS. 20-59, and the external fixation systems and related fixation methods 300 of FIGS. 20-59, and therefore like reference numerals preceded with "4" are used to indicate like aspects or functions, and the description above directed to aspects or functions thereof (and the alternative embodiments thereof) equally applies to the external fixation systems and methods 400.

As shown in FIGS. 82-105, the exemplary system 400 differs from the system 100, the system 200 and the system 300 in the rotatable coupling or connection mechanism between the strut assemblies 410 (e.g., pairs of oppositely oriented or extending strut assemblies) and the platforms or rings 420, 430. As shown in FIGS. 82-85 the system 400 utilizes strut mounts 441 that securely and removably couple and clamp to corresponding projections 443 of the platforms 420, 430 as shown in FIGS. 84 and 86-89. The mounts 441 may be configured to couple to the platforms 420, 430 by clamping onto the projections 443 via a threaded post portion 402 that threadably engages within a threaded aperture 447 positioned adjacent to the projections 443. In some embodiments, only the apertures 447 of the platforms 420, 430 that are positioned adjacent or immediate behind the projections 443 may be threaded (i.e., and other similar apertures of the platforms 420, 430 may be non-threaded).

Figure 84:
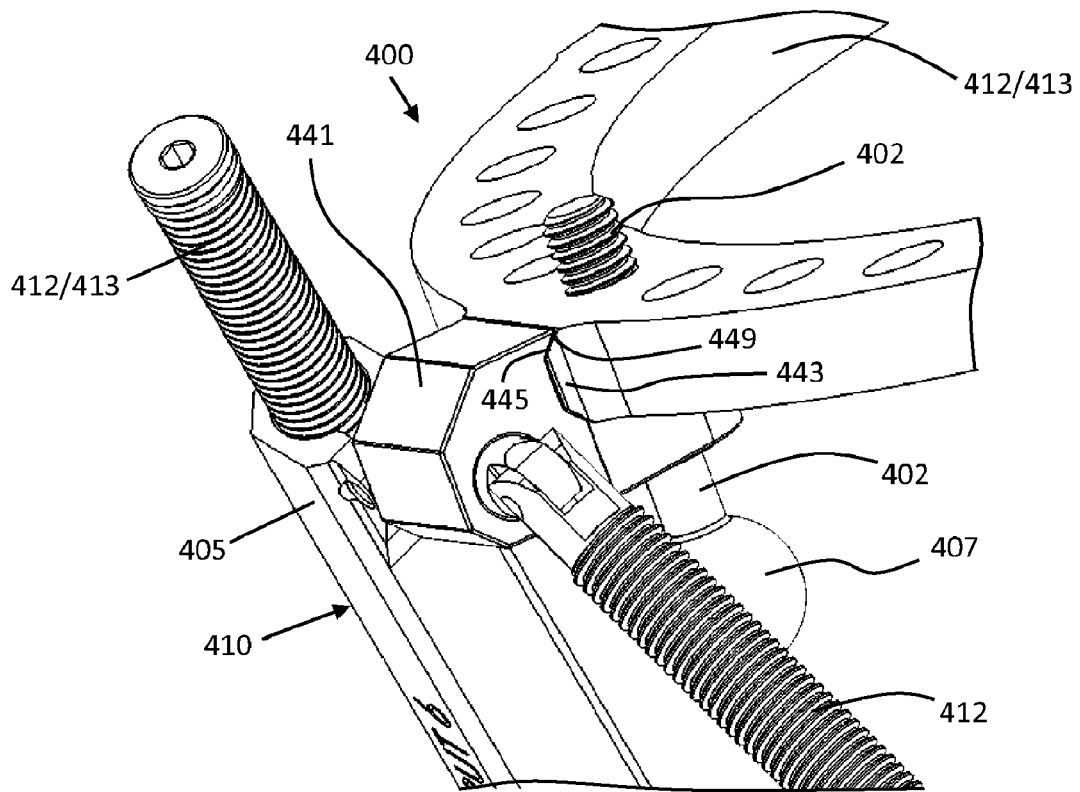
FIG. 84 is an exterior bottom perspective view of the strut-platform connection mechanism of FIG. 83.
Figure 85:
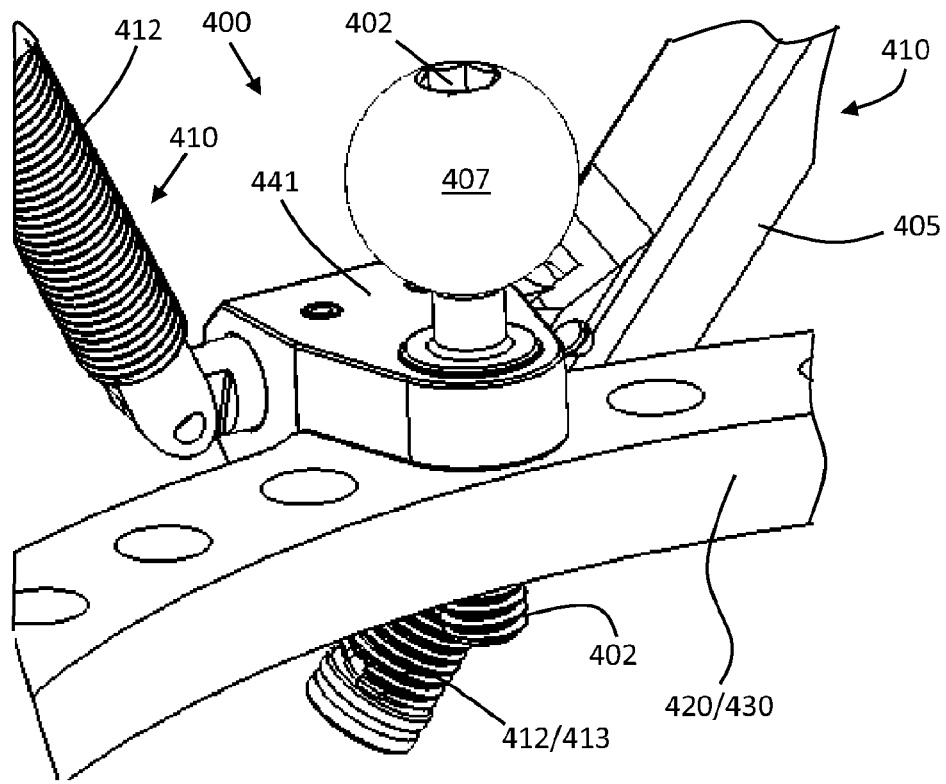
FIG. 85 is an interior elevational perspective view of the strut-platform connection mechanism of FIG. 83.
Figure 86:
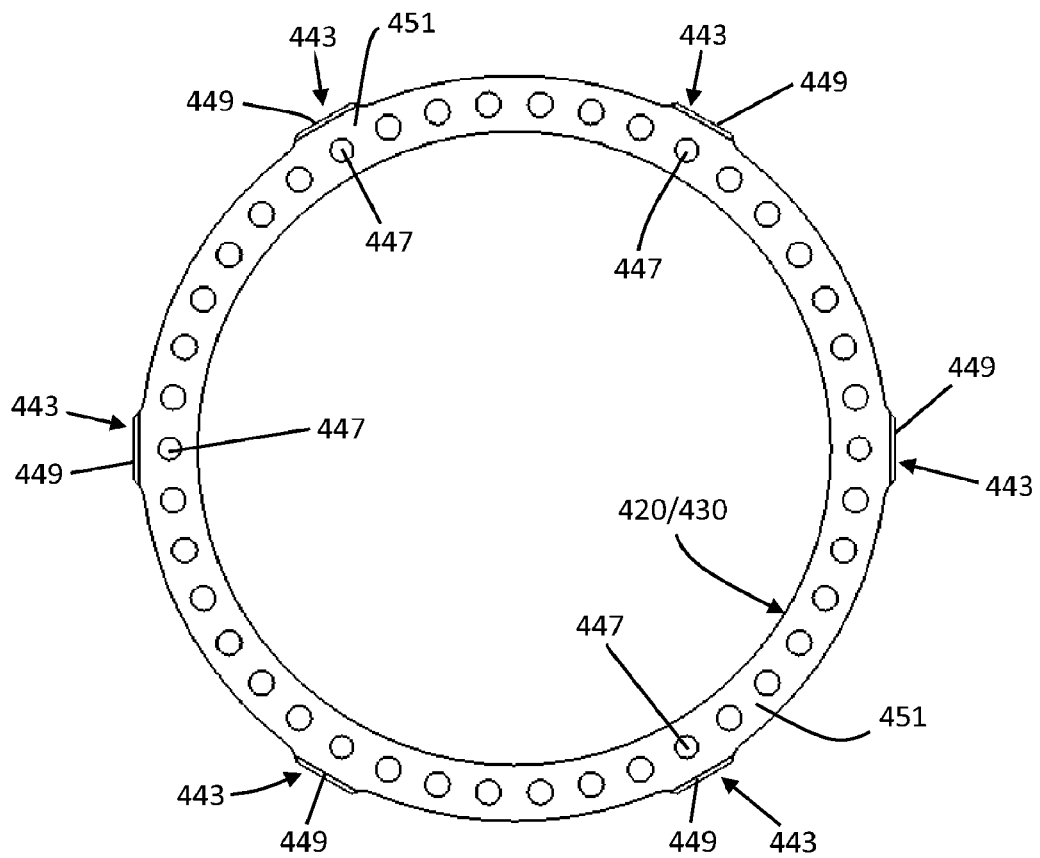
FIG. 86 is top view of a platform of the external bone fixation system of FIG. 82.
Figure 87:
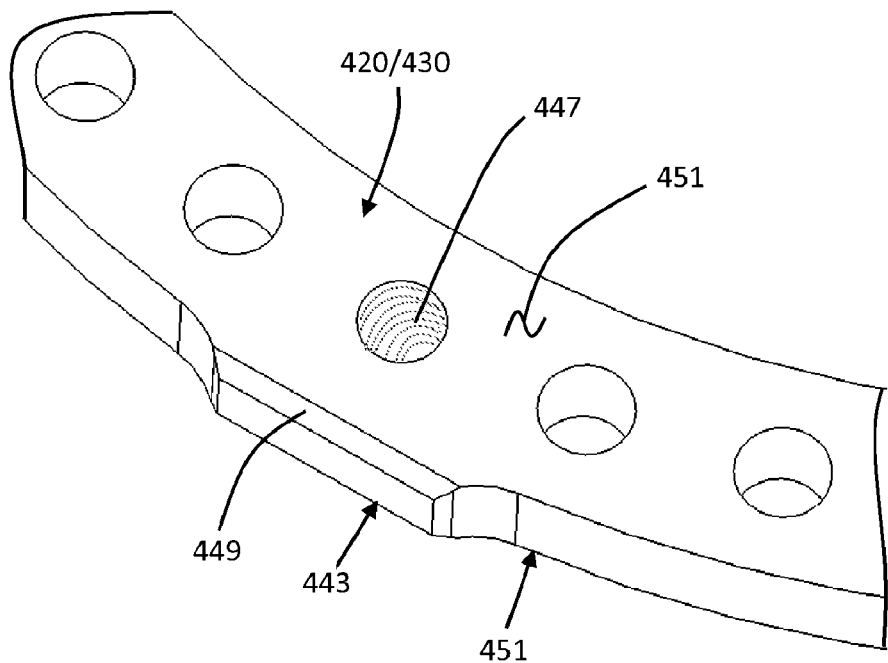
FIG. 87 is an elevational perspective view of the platform of FIG. 86.

The threaded post 402 may extend through the threaded aperture 447 of the platforms 420, 430 so that a portion of the post 402 extends outwardly past the platforms 420, 430 on an opposing side thereof as compared to the mount 441, as shown in FIGS. 84 and 85. In some embodiments, this extended portion of the threaded post 402 may be utilized to couple other mechanisms to the platforms 420, 430. The threaded posts 402 may be manually threadably engaged to the threaded apertures 447 of the platforms 420, 430 via the fiducial markers 407 positioned at, or extending from, an end of the post portion 402. For example, the fiducial markers 407 may be manually engaged by a surgeon or other user and utilized to rotate the threaded posts 402 such that the threaded posts 402 threadably engage and tighten down into the threaded apertures 447. Similarly, the fiducial markers 407 may be utilized to rotate the threaded posts 402 out from threaded aperture 447. In some embodiments, the fiducial markers 407 may include an aperture or indentation configured to allow a tool to apply a torque to the fiducial markers 407 to effectuate rotation of the threaded posts 402 relative to the threaded apertures 447.

Figure 82:
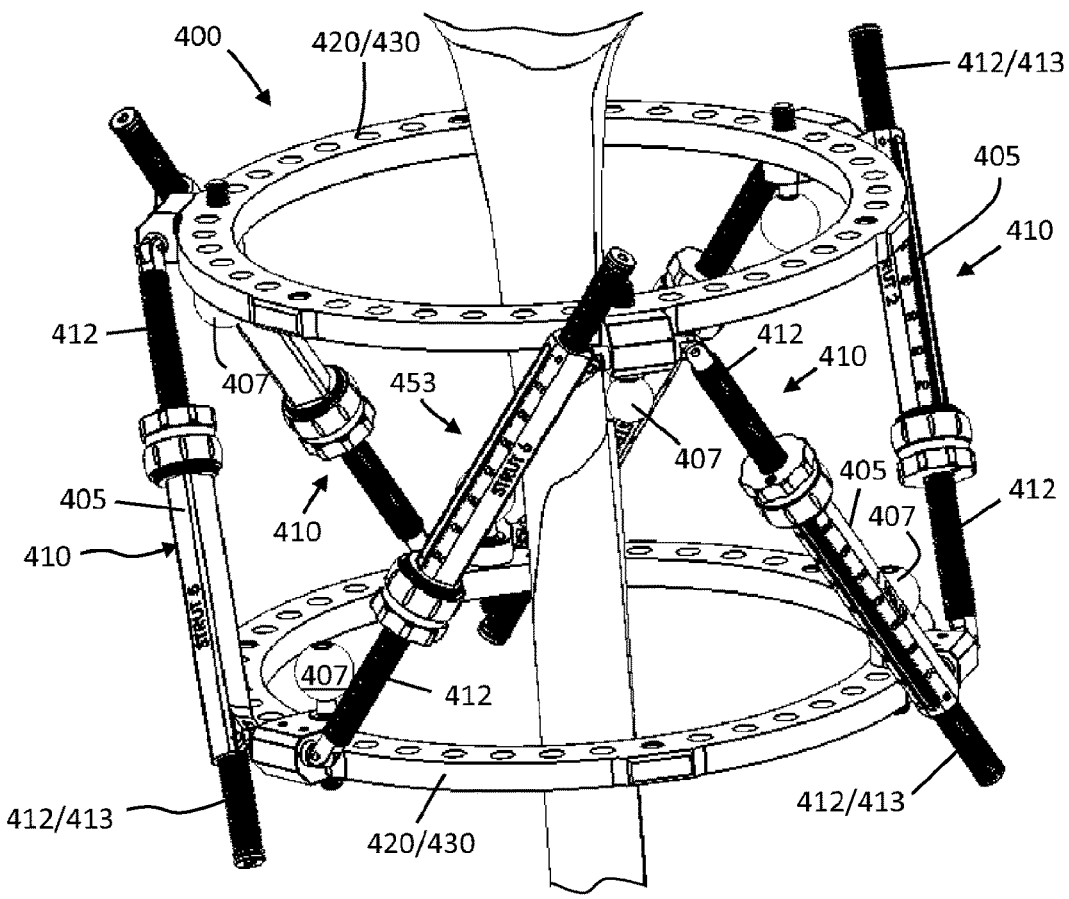
FIG. 82 is a perspective view of another exemplary external bone fixation system according to the present disclosure.

As shown in FIG. 82, the mount 441 may be configured such that the fiducial markers 407 are positioned interiorly of the platforms 420, 430 such that the posts 402 extend through the threaded apertures 447 from an interior side thereof to an exterior side thereof at least generally along the longitudinal axis of the strut assemblies 410. In this way, the fiducial markers 407 may be spaced from the ends of the strut assemblies 410 and not interfere with the extended nature of the threaded rod portion 412, 413 of the strut assemblies 410 extending out from the strut barrels 405. The outer portions of the platforms 420, 430, particularly adjacent to the projections 443, may thereby be open and void of any structure that may interfere with the threaded rod portion 412, 413 of the strut assemblies 410 extending out from the strut barrels 405 past the platforms 420, 430.

As shown in FIGS. 86-89, each of the platforms 420, 430 may include at least three projections 443 (to couple to a pair of strut assemblies 410, such as three pairs of strut assemblies 410 in a hexapod configuration) that extend radially outward from the platforms 420, 430. Each projection 443 may include a substantially flat or planar outer-most face in the radial direction, as shown in FIGS. 86-89. As also shown in FIGS. 86-89, each projection 443 may include may include angled support surface 449 that extend from the planar outer face and the inner and outer surfaces 451 of the platforms 420, 430. The planar outer faces of the projections 443 may thereby be thinner than the main portions of the platforms 420, 430 as measured between the inner and outer surfaces 451. The planar outer face of the projections 443 may be oriented substantially perpendicular to the inner and outer surfaces 451 of the platforms 420, 430. The angled support surfaces 449 of the projections 443 may thereby face or be angled radially outward and either outwardly or inwardly (e.g., the support surface 449 extending between the outer face of the projection 443 and the outer surface 451 of the platforms 420, 430 may face radially outward and upward, and the support surface 449 extending between the outer face of the projection 443 and the inner surface 451 of the platforms 420, 430 may face radially outward and inward). As the mounts 441 may be positioned on the inward faces surfaces 451 of the platforms 420, 430, as shown in FIG. 82, the mounts 441 may engage the inwardly-facing support surfaces 449 of the projection 443 and the inward faces surfaces 451 of the platforms 420, 430 to securely clamp to the platforms 420, 430, as explained further below.

Figure 83:
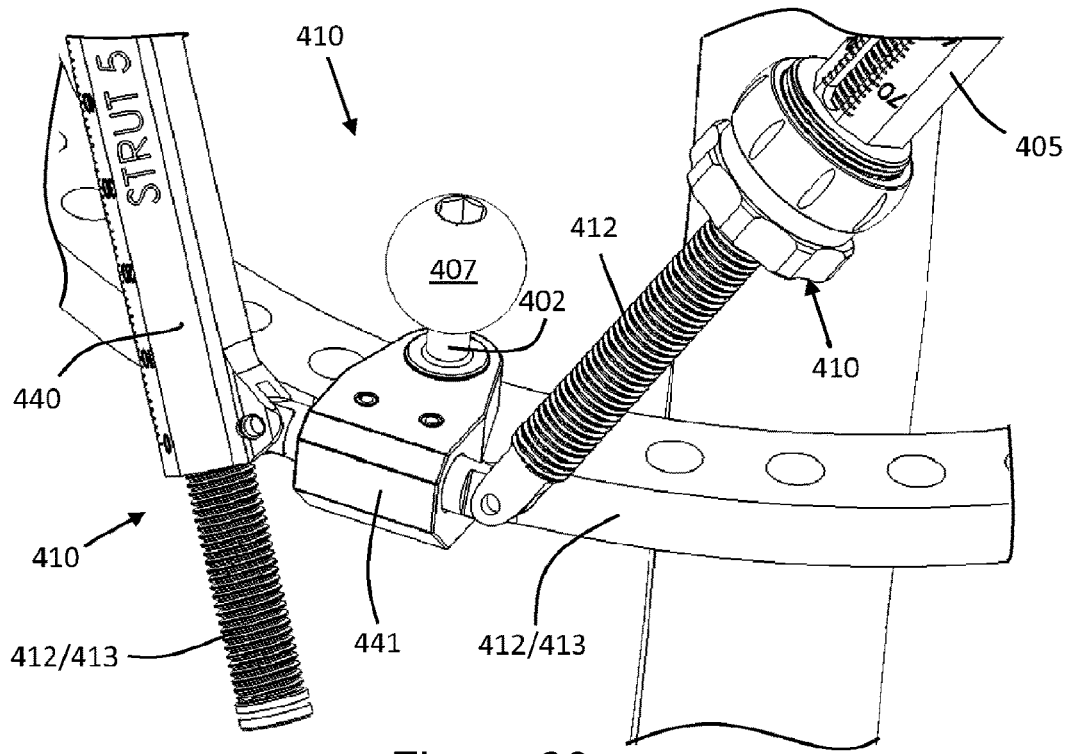
FIG. 83 is an exterior elevational perspective view of a strut-platform connection mechanism of the external bone fixation system of FIG. 82 coupling a pair of strut assemblies to a platform.

As shown in FIGS. 90-83, the mounts 441 may clamp or couple to the platforms 420, 430 (e.g., via the projections 443 and threaded apertures 447) such that a back portion of the mounts 441 extends radially outward past the outer face of the projections 443 and the outward surface of the platforms 420, 430. This back portion of the mounts 441 may include a pair of trunnions 453 rotatably coupled within apertures or a channel of the mounts 441, as shown in FIGS. 90-98. The trunnions 453 may extend outwardly from a respective mount 441 to allow one end portion of the first threaded rod 412 or a strut barrel 405 to be rotatably coupled thereto, as shown in FIGS. 82-85. For example, a first threaded rod 412 and a strut barrel 405 may be rotatably coupled to the exposed portions of a pair of trunnions 453 of a mount 441, such as via a pin connection. The connection between the trunnions 453 and the pair of strut assemblies 410 of each mount 441 may provide relative rotation of the strut assemblies 110 about an orthogonal axis.

Figure 97:
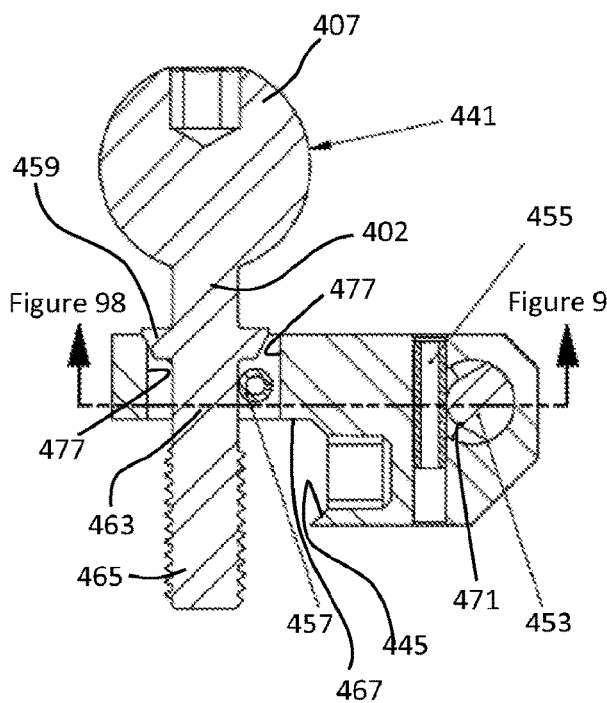
FIG. 97 is a cross-sectional view of the strut-platform connection mechanism of FIG. 94.
Figure 98:
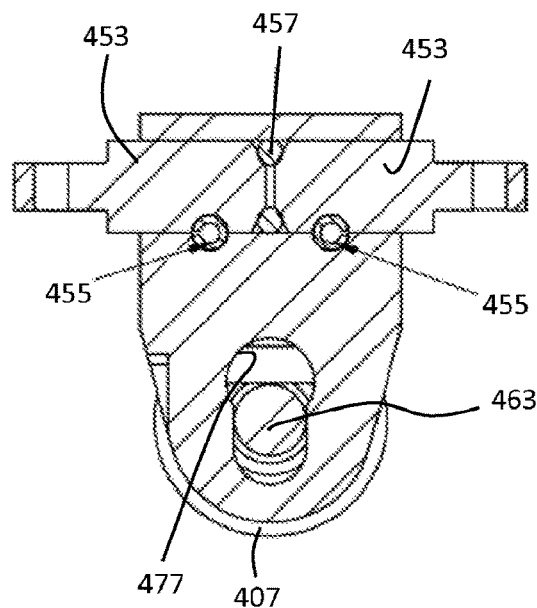
FIG. 98 is another cross-sectional view of the strut-platform connection mechanism of FIG. 94.
Figure 99:
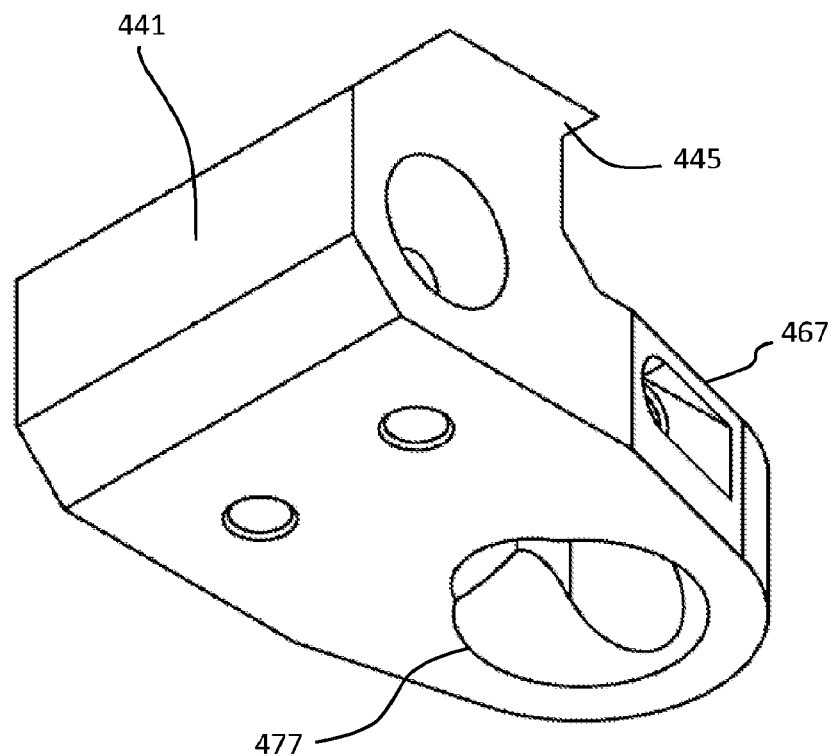
FIG. 99 is a perspective view of a connection mechanism mount of the strut-platform connection mechanism of FIG. 83.
Figure 100:
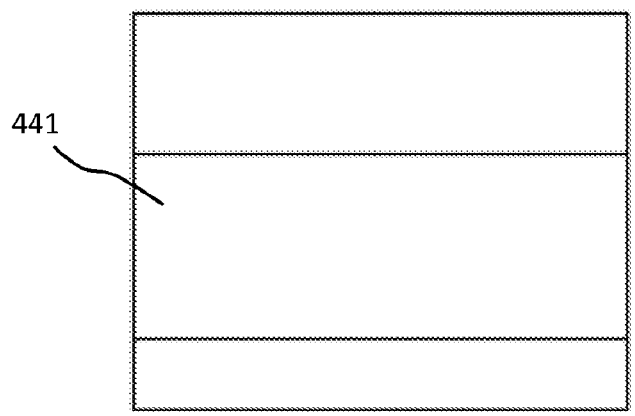
FIG. 100 is a front view of the connection mechanism mount of FIG. 99.
Figure 101:
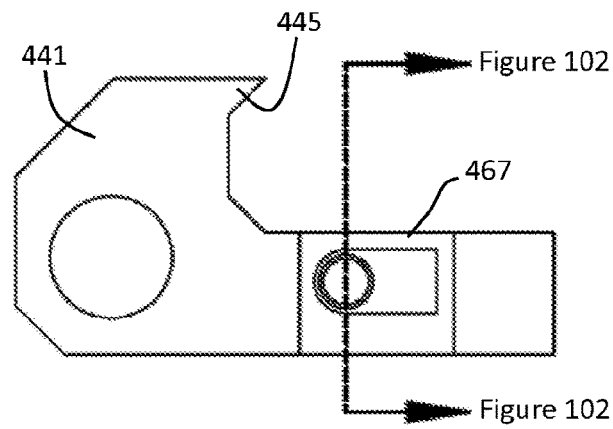
FIG. 101 is a side view of the connection mechanism mount of FIG. 99.
Figure 102:
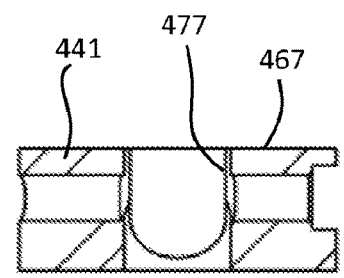
FIG. 102 is a cross-sectional view of the connection mechanism mount of FIG. 99.
Figure 103:
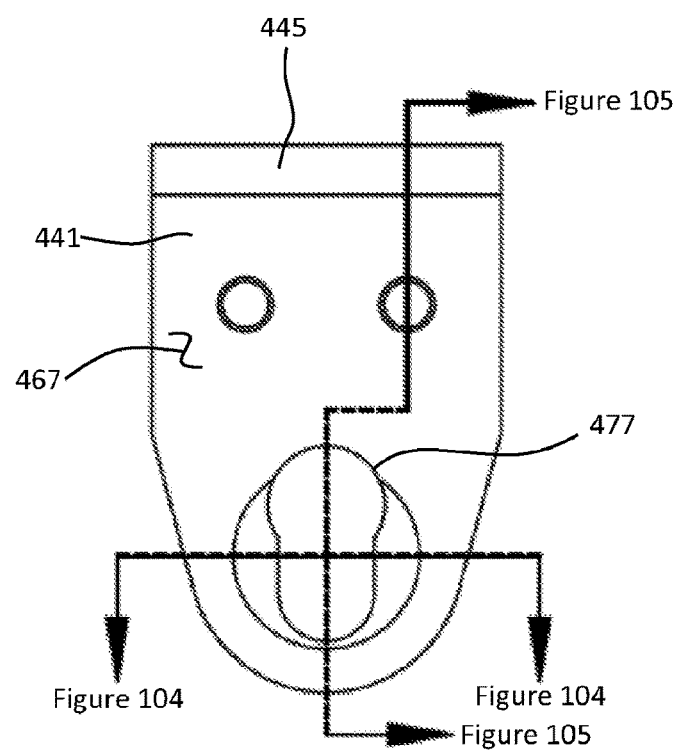
FIG. 103 is a top view of the connection mechanism mount of FIG. 99.
Figure 104:
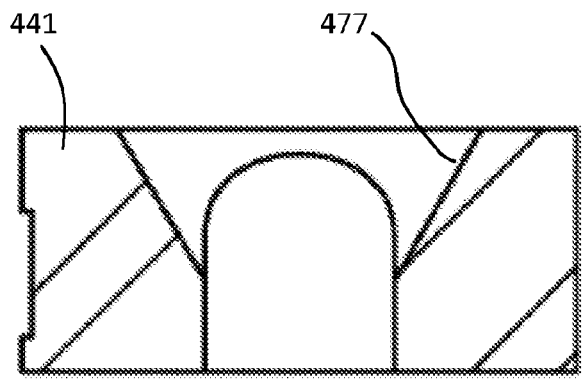
FIG. 104 is another cross-sectional view of the connection mechanism mount of FIG. 99.
Figure 105:
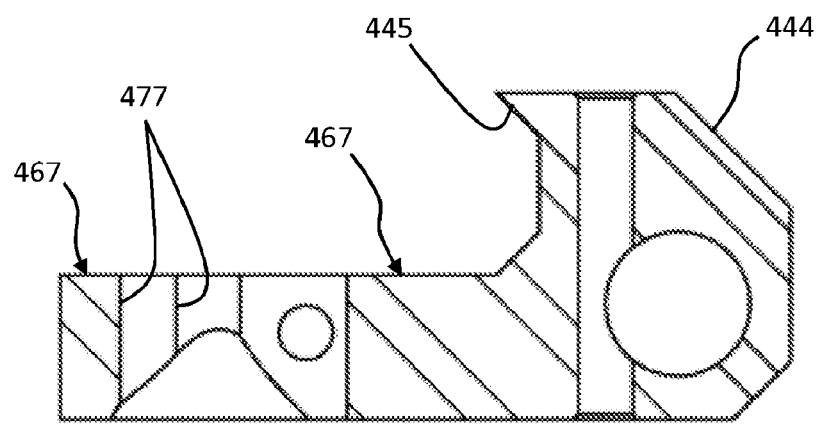
FIG. 105 is another cross-sectional view of the connection mechanism mount of FIG. 99.

The trunnions 453 themselves may also provide relative rotation of the strut assemblies 110 about an orthogonal axis. For example, the trunnions 453 may be able to rotate within the aperture(s) or channel(s) of the mount 441. In some embodiments, the mount 441 may be configured to provide a limited amount of rotation of the trunnions 453 with respect to the mount 441 (e.g., such as about 300 degrees or 270 degrees). In some embodiments, the trunnions 453 may be cylindrical members contained within a cylindrical bore or aperture of the mount 441, as shown in FIGS. 90-98, 101 and 105. As shown in FIGS. 97 and 98, the portion of the trunnions 453 positioned within the mount 441 may include a groove that partially encircles or extends about the outer surface thereof. As shown in FIGS. 90, 91, 93, 94 and 96-98, the mount 441 may include trunnion pins or other mechanism, such as spring pins, that extend through respective apertures such that the pins mate within the grooves of the trunnions 453 (see FIGS. 97 and 98). The trunnion pins thereby prevent the trunnions 453 from disengaging from the mounts 441 and allow limited rotation of the trunnions 453 within the mount 441. In some other embodiments, the grooves may encircle the trunnions 453 such that they are able to fully or completely rotate within the mounts 441. To allow free and smooth rotation of the trunnions 453 within the mount 441, the mount 441 may include an o-ring, washer or other similar member 457 positioned between the pair of trunnions 453, as shown in FIG. 98.

Figure 93:
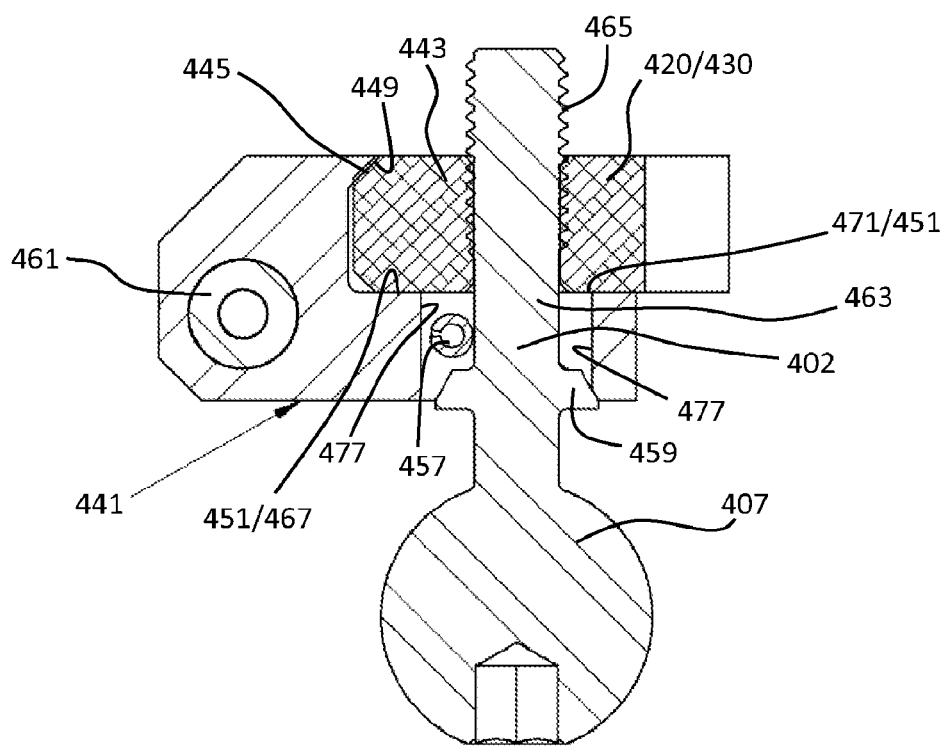
FIG. 93 is a cross-sectional view of the strut-platform connection mechanism of FIG. 90.
Figure 94:
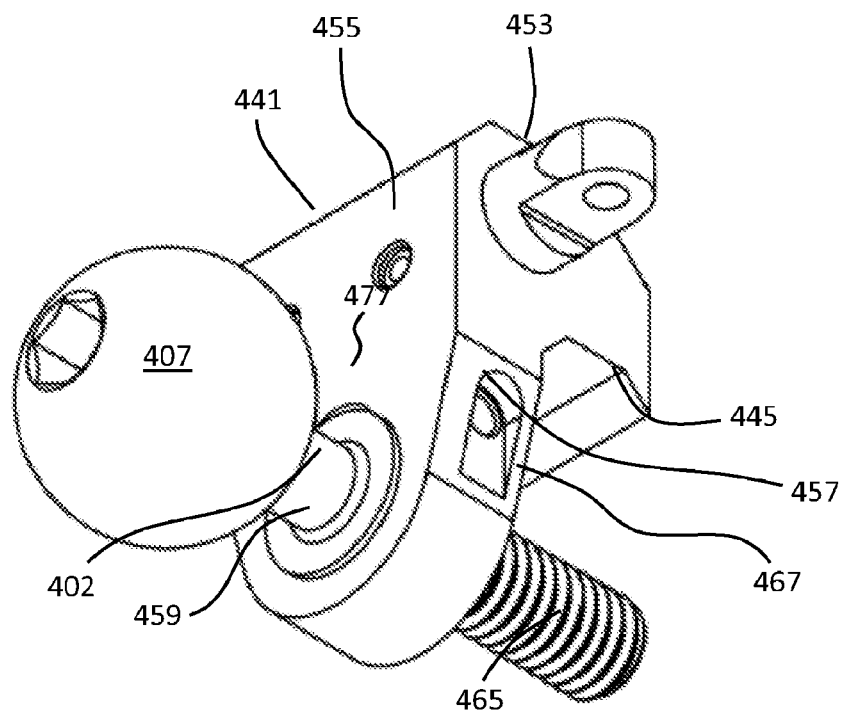
FIG. 94 is a perspective view of the strut-platform connection mechanism of FIG. 83.
Figure 95:
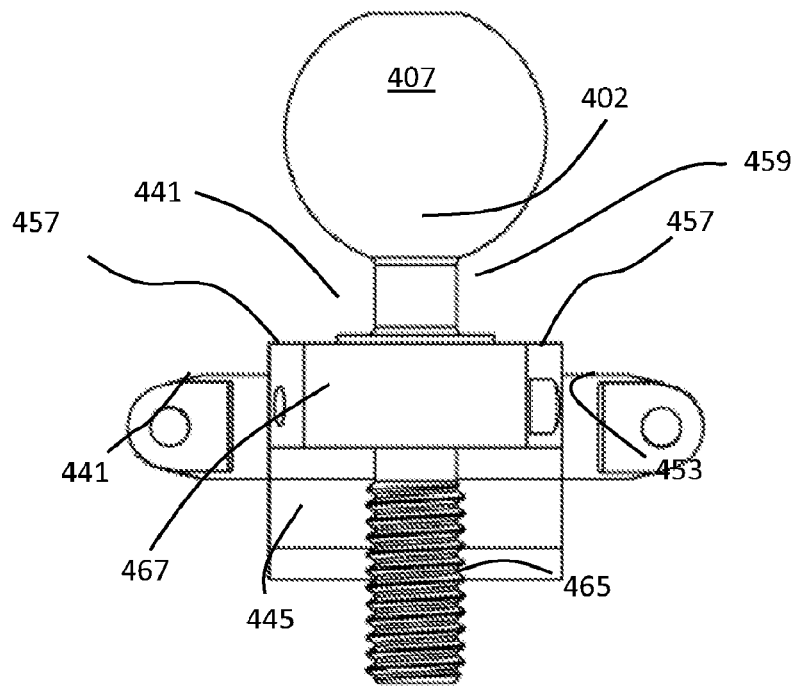
FIG. 95 is a side view of the strut-platform connection mechanism of FIG. 94.
Figure 96:
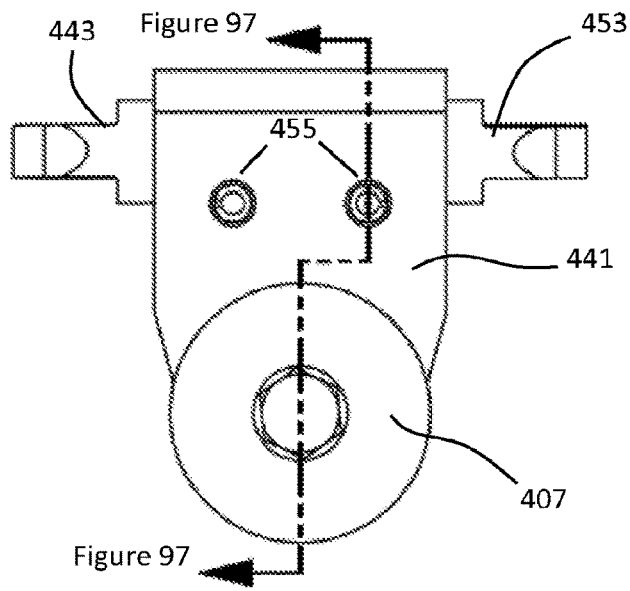
FIG. 96 is a top view of the strut-platform connection mechanism of FIG. 94.

The threaded post 402 may be movably retained or captured within a keyhole aperture 477 of the mount 441 via a post pin or other member 457, such as a spring pin, as shown in FIGS. 90, 93-103. As shown in FIGS. 93, 97, 98 and 103, the mount 441 may include a keyhole or other irregular-shaped aperture 477 extending therethrough between an exterior surface and an engagement surface 467. The engagement surface 467 of the mount 441 may engage the interior surface of the platforms 420, 430 during use, as shown in FIG. 93. As shown in FIGS. 93 and 97, the post 402 may include a threaded portion 465, a conical or beveled flange 459, and a non-threaded portion 463 extending between the threaded portion 465 and the beveled flange 459. The non-threaded portion 463 of the post 402 may define a smaller diameter or width than the threaded portion 465 and the beveled flange 459. The irregular-shaped aperture 477 may include a first portion that is sized to allow the threaded portion 465 to pass therethrough, and a second portion that is sized to prevent the threaded portion 465 to pass therethrough but allow the non-threaded portion 463 to pass therethrough or be seated therein, as shown in FIG. 98. To capture the post 402 within the irregular-shaped aperture 477 and movably couple the post 402 to the mount 441, the post pin 457 may pass at least partially through the first portion of irregular-shaped aperture 477 with the non-threaded portion 463 positioned thereon to at least partially block off the first portion. As the second portion of the irregular-shaped aperture 477 is too small for the threaded portion 465 and the beveled flange 459 to pass through, the post 402 is effectively captured within the irregular-shaped aperture 477. The mount 441 may thereby include an aperture or channel configured to position the post pin 457 at least partially through the first portion of irregular-shaped aperture 477. In use, the mounts 443 may pre-assembled with the posts 402 captured within the mounts 443 via the post pins 457.

The outer surface of the mount 441 that opposes the engagement surface 467 may include a bevel or countersink about a portion of the irregular-shaped aperture 477 corresponding to the conical or beveled flange 459, as shown in FIGS. 93, 97, 99, 102 and 103. The countersink of the irregular-shaped aperture 477 may be positioned at least partially within or about the second smaller portion of the irregular-shaped aperture 477. In this way, when the threaded portion 465 of the post 402 is torqued down into the threaded aperture 447 of the platform 420, 430, the engagement surface 467 abuts and engages the inner surface 451 of the platform 420, 430 and the beveled flange 459 self-seats or centers itself into the countersink portion of the irregular-shaped aperture 477, as shown in FIGS. 90, 92-95, 97 and 98.

The countersink of the irregular-shaped aperture 477 may also be configured to pull or translate the mount 441 radially inwardly such that a lip or arm portion 445 of the mount 441 engages the inner angled support surface 449 of the projection 443 of the platform 420, 430, as shown in FIGS. 84, 93 and 97. As shown in FIGS. 84, 93, 94, 95, 97, 99, 101 and 105, the lip or arm portion 445 of the mounts 443 may extend axially inwardly from the engagement surface 467 and radially inwardly toward the interior or center of the platform 420, 430. The lip portion 445 of the mounts 443 may thereby extend along or about the planar outer face of the projection 443 and the inward angled support face 449, as shown in FIGS. 84 and 93. Further, the mount 441 and projection 443 may be configured such that when the threaded portion 465 of the post 402 is torqued down into the threaded aperture 447 of the platform 420, 430, and the engagement surface 467 abuts and engages the inner surface 451 of the platform 420, 430 and the beveled flange 459 seats itself into the countersink portion of the irregular-shaped aperture 477 thereby translating the mount 441 radially inwardly, the lip portion 445 engages the inner angled support surface 449 of the projection 443 of the platform 420, 430. In this way, the mount 441 may be clamped to the inner surface 451 and the inner angled support surface 449 of a platform 420, 430 to securely couple thereto. It is noted that the other portions of the lip portion 445 may be spaced slightly from the planar outer surface and the outer angled support surface 449 of the projections 443 when the mount 441 is clamped to the platforms 420, 430, as shown in FIG. 93.

In use, the threaded portion 465 of the post 402 may threaded into the threaded aperture 447 associated with one of the projections 443 of one of the platforms 420, 430. The non-threaded portion 463 of the post 402 may be positioned within the second larger portion of the irregular-shaped aperture 477 to allow the lip portion 445 to extend past the outer surface and angles support surfaces 449 of the projection 443. As the post is torqued and tightened into the threaded aperture 447, the beveled flange portion 459 may engage the countersink of the irregular-shaped aperture 477 and seat itself thereon by translating the mount 441 radially inwardly (and the non-threaded portion 463 translate toward or partially into the first smaller portion of the irregular-shaped aperture 477). The engagement surface 467 of the mount 441 may thereby be forced against and engage and abut the inward support or engagement surface 451 of the platform 420, 430. Such radially inward motion or translation of the mount 441 may thereby the lip portion 445 of the mount 441 against and into engagement or abutment with the inner angled support surface 449 of the projection 443. In this way, the mount 441 (and thereby the strut assemblies coupled thereto) may be clamped to the angled support surface 449 of the projection 443, the inward support or engagement surface 451 of the platform 420, 430 and the threaded aperture 447 of the platform 420, 430.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An external bone fixation system, comprising:
   a first platform defining an opening and configured to couple to a first bone segment;
   a second platform defining an opening and configured to couple to a second bone segment; and
   at least six length-adjustable strut assemblies each including an externally threaded rod portion translatably coupled through an internally threaded strut body portion, the rod portion of each strut assembly being coupled to one of the first and second platforms via a respective joint and the strut body portion of each strut assembly being coupled to the other of the first and second platforms via a respective joint,
   wherein the strut assemblies are coupled to the first and second platforms in pairs of strut assemblies spaced about the first and second platforms,
   wherein the pairs of strut assemblies each include a first strut assembly coupled to the respective platform via the joint of the threaded rod portion thereof and a second strut assembly coupled to the respective platform via the joint of the strut body portion thereof, and further comprising at least one add-on externally threaded rod portion attachable to the externally threaded rod portion of one of the strut assemblies while the rod portion of the one strut assembly remains coupled to the first or second platforms, the strut body portion of the one strut assembly remains coupled to the other of the first or second platforms, and the rod portion of the one strut assembly and the strut body portion of the one strut assembly remain translatably coupled together.

2. The system of claim 1, wherein the at least six length-adjustable strut assemblies are coupled to each other and form a singular construct prior to coupling to the first and second platforms.

3. The system of claim 1, wherein the length of the strut assemblies can be adjusted by rotation of a nut threadably engaged within the threaded rod portion and axially fixed to the strut body portion within a cavity thereof.

4. The system of claim 3, wherein the nut is partially threaded, and wherein the threaded portion of the nut is biased into engagement with the threaded rod portion via a release nut threaded engaged with external threads of the strut body portion.

5. The system of claim 4, wherein translation of the release nut along the strut body portion in a first direction forces members into the cavity to force the nut concentric with the threaded rod portion and into threaded engagement therewith.

6. The system of claim 5, wherein translation of the release nut along the strut body portion in a second direction allow the members to detract from the cavity to allow the release nut to translate eccentric to the threaded rod portion and disengage therewith.

7. The system of claim 1, wherein the pair of strut assemblies are coupled to the first and second platforms via respective mounts, and wherein the mounts are fixed to the first and second platforms via projections and threaded apertures of the first and second platforms.

8. The system of claim 7, wherein each mount includes a threaded post that threadably engages a threaded aperture of a respective first or second platform.

9. The system of claim 8, wherein a fiducial marker is positioned at an end of each threaded post, and wherein one of the fiducial marker is unique from the other fiducial markers.

10. The system of claim 8, wherein each projection includes an angled support surface and inner support surface, and wherein each mount includes an engagement surface that engages the inner support surface and a lip portion that engages the angled support surface to clamp the mount to a respective first or second platform.

11. The system of claim 10, wherein each threaded post passes through an irregular aperture through a respective mount, and wherein a portion of the irregular aperture includes a countersink.

12. The system of claim 11, wherein each threaded post includes a beveled flange configured to mate with the countersink of the associated irregular aperture, and wherein the beveled flange acts to translate the mount with respect to the respective first or second platform so that the lip portion that engages the angled support surface.

13. The system of claim 1, wherein the add-on externally threaded rod portion is attachable to one of the externally threaded rod portions via a connecting member that includes a first externally threaded portion of a first pitch, a non-threaded portion, and a second externally threaded portion of a second pitch that is greater than the first pitch.

14. The system of claim 13, wherein the add-on externally threaded rod portion includes a first internally threaded portion with internal threads of the first thread pitch, and the externally threaded rod portions includes a second internally threaded portion with internal threads of the second thread pitch.

15. The system of claim 14, wherein the add-on externally threaded rod portion is hollow such that an end of the connecting member is accessible through the add-on externally threaded rod portion when the first externally threaded portion is threadably coupled within the first internally threaded portion.

16. The system of claim 14, wherein the non-threaded portion defines a maximum diameter that is smaller than a maximum diameter of the first externally threaded portion and a maximum diameter of the second externally threaded portion.

17. The system of claim 16, wherein the non-threaded portion is positioned within the first internally threaded portion and the second internally threaded portion when the add-on externally threaded rod portion is fully attached to one of the externally threaded rod portions via the connecting member.

18. The system of claim 13, wherein the non-threaded portion defines a maximum diameter that is smaller than a maximum diameter of the first externally threaded portion and a maximum diameter of the second externally threaded portion.

19. The system of claim 13, wherein the at least one add-on externally threaded rod portion and the externally threaded rod portions are configured such that when the at least one add-on externally threaded rod portion is attached to the externally threaded rod portion of one of the strut assemblies via the connector member, the externally threaded rod portion and the strut assembly cooperatively form a clocked continuous external thread profile.

20. The system of claim 1, wherein the at least one add-on externally threaded rod portion and the externally threaded rod portions are configured such that when the at least one add-on externally threaded rod portion is attached to the externally threaded rod portion of one of the strut assemblies, the externally threaded rod portion and the strut assembly cooperatively form a clocked consistent external thread profile.

* * * * *